(12) United States Patent
Yamamoto et al.

(10) Patent No.: US 8,592,452 B2
(45) Date of Patent: Nov. 26, 2013

(54) CYCLIC AMINE COMPOUND

(75) Inventors: Satoshi Yamamoto, Osaka (JP); Atsushi Hasuoka, Osaka (JP)

(73) Assignee: Takeda Pharmaceutical Company Limited, Osaka-shi (JP)

( * ) Notice: Subject to any disclaimer, the term of this patent is extended or adjusted under 35 U.S.C. 154(b) by 582 days.

(21) Appl. No.: 11/989,825

(22) PCT Filed: Aug. 1, 2006

(86) PCT No.: PCT/JP2006/315559
§ 371 (c)(1),
(2), (4) Date: Jan. 31, 2008

(87) PCT Pub. No.: WO2007/015567
PCT Pub. Date: Feb. 8, 2007

(65) Prior Publication Data
US 2010/0152236 A1    Jun. 17, 2010

(30) Foreign Application Priority Data
Aug. 1, 2005  (JP) .................................. 2005-223462

(51) Int. Cl.
*A61K 31/445*    (2006.01)
*A61K 31/40*    (2006.01)

(52) U.S. Cl.
USPC ......................................... 514/317; 514/423

(58) Field of Classification Search
USPC ................................................. 514/317, 423
See application file for complete search history.

(56) References Cited

U.S. PATENT DOCUMENTS

| | | |
|---|---|---|
| 3,103,542 A | 9/1963 | Fielden |
| 3,639,411 A | 2/1972 | Albertson et al. |
| 5,049,577 A | 9/1991 | Varma et al. |
| 6,437,167 B1 | 8/2002 | Sunjic et al. |
| 2002/0058290 A1 | 5/2002 | Ostrowski et al. |
| 2002/0173445 A1 | 11/2002 | Salvati et al. |
| 2003/0040531 A1 | 2/2003 | Fujishima et al. |
| 2003/0114420 A1 | 6/2003 | Salvati et al. |
| 2004/0077605 A1 | 4/2004 | Salvati et al. |
| 2004/0077606 A1 | 4/2004 | Salvati et al. |
| 2004/0083559 A1 | 5/2004 | Sabelle et al. |
| 2004/0176324 A1 | 9/2004 | Salvati et al. |
| 2005/0101657 A1 | 5/2005 | Furuya et al. |
| 2005/0119228 A1 | 6/2005 | Salvati et al. |
| 2005/0192253 A1 | 9/2005 | Salvati et al. |
| 2005/0256048 A1 | 11/2005 | Salvati et al. |
| 2005/0272799 A1 | 12/2005 | Salvati et al. |
| 2005/0282813 A1 | 12/2005 | Salvati et al. |
| 2006/0106067 A1 | 5/2006 | Shiraishi et al. |
| 2007/0254875 A1* | 11/2007 | Zhi et al. ................... 514/230.5 |

FOREIGN PATENT DOCUMENTS

| | | |
|---|---|---|
| EP | 1553074 A1 | 7/2005 |
| JP | 09-084596 | 3/1997 |
| JP | 2002-088073 | 3/2002 |
| WO | 02-45669 A1 | 6/2002 |
| WO | WO-2005/090282 | 9/2005 |
| WO | WO-2005/108351 | 11/2005 |
| WO | WO 2006/076317 | * 7/2006 |
| WO | WO 2006/124447 | * 11/2006 |

OTHER PUBLICATIONS

Chiralty, 2003, 15, pp. 550-557; Enantioseparation of Racemic 4-Aryl-3,4-dihydro-2(1H)-pyrimidones on Chiral Stationary Phases Based on 3,5-Dimethylanilides of N-(4-Alkylamino-3,5-dinitro)benzoyl L-α-Amino Acids.

(Continued)

*Primary Examiner* — San-Ming Hui
(74) *Attorney, Agent, or Firm* — Edwards Wildman Palmer LLP; David G. Conlin; Edmund J. Koundakjian

(57) ABSTRACT

A compound represented by the formula (I)

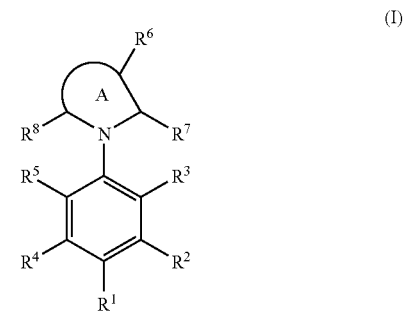

(I)

wherein ring A is a 5- to 8-membered ring optionally having further substituent(s) other than $R^6$, $R^7$ and $R^8$,
$R^1$ is an electron-withdrawing group,
$R^2$, $R^3$, $R^4$ and $R^5$ are each independently a hydrogen atom, a halogen atom, a group bonded via a carbon atom, a group bonded via a nitrogen atom, a group bonded via an oxygen atom or a group bonded via a sulfur atom,
$R^6$ is a halogen atom, a group bonded via a carbon atom, a group bonded via a nitrogen atom, a group bonded via an oxygen atom or a group bonded via a sulfur atom,
$R^7$ is a cyano group, a nitro group, an acyl group optionally having substituent(s), an optionally esterified or amidated carboxyl group or a hydrocarbon group optionally having substituent(s), or $R^6$ and $R^7$ optionally form, together with the carbon atom bonded thereto, a ring optionally having substituent(s), and
$R^8$ is a hydrogen atom, a halogen atom, a group bonded via a carbon atom, a group bonded via a nitrogen atom, a group bonded via an oxygen atom or a group bonded via a sulfur atom, or a salt thereof has a superior action as an androgen receptor modulator, and is useful for the prophylaxis or treatment of hypogonadism, male climacteric disorder, frailty, cachexia, osteoporosis and the like.

4 Claims, No Drawings

(56) References Cited

OTHER PUBLICATIONS

Tetrahedron, 2002, 58, pp. 8793-8798; A diversity oriented synthesis of highly functionalized unsymmetrical biaryls through carbanion induced ring transformation of 2H-pyran-2-ones.
Tetrahedron Letters, 2001, 42, pp. 7127-7129; Carbanion-induced base-catalyzed synthesis of unsymmetrical biaryls from suitably functionalized 2H-pyran-2-ones through ring-transformation reactions.
Nihon Kagaku Kaishi 1976, 1, pp. 200-202.
Tetrahedron, 1967, 23, pp. 1845-1855; 1,3,5-Trichlor-2,4,6-Tricyan-Benzol UND 1,3,5-Trifluor-2,4,6-Tricyan-Benzol.
Organic Letters, 2005, 7(13), pp. 2575-2578; Palladium-Catalyzed Tandem N-Arylation/Carboamination Reactions for the Stereoselective Synthesis of N-Aryl-2-benzyl Pyrrolidines.
Journal of Medicinal Chemistry, 1972, 15, pp. 827-836; Folate Antagonists. 3. 2,4-Diamino-6-(heterocyclic)quinazolines, a Novel Class of Antimetabolites with Potent Antimalarial and Antibacterial Activity.
J. Org. Chem., 1994, 59, pp. 3175-3185; Expeditious Synthesis of Azasugars by the Double Reductive Amination of Dicarbonyl Sugars.
Journal of Chemical Society, 1961, pp. 189-201; Clark-Lewis and Mortimer; The 4-Hydroxypipecolic Acid from *Acacia* species, and it's Stereoisomers.
Journal of American Chemical Society, 1964, 86, pp. 5293-5299; 3-Pyrrolidinones by Intramolecular Condensation.
J. Chem. Research (S), 1998, 2, pp. 82-83; Stereoisomeric Styryl-substituted Pyrrolidines, 3,7-Diazobicyclo[3.3.0] octanes and 2-Styrylpyrroles from Cinnamaldehyde Iminium-N-methanide 1,3-Dipoles.
Acta Crystallagraphica Section C, 1996, C52, pp. 207-210; Two cis Ring-Fused exo N-Aryl Hetero-cycles: 1-Phenyl-2-(2,4,6-trimethylpheny1)-decahydroquinolin-4-one and 1-(4-Trifluoromethylphenyl)-2-phenyldecahydro-quinolin-4-one.
Tetrahedron, 1998, 54, pp. 875-894; A Novel Hetero-Diels-Alder Approach Towards Perhydro Quinolinones Bearing an Angular Methyl Group.
J. Liq. Chrom. & Rel. Technol., 2000, 23(8), pp. 1203-1215; Preparation and Evaluation of the Chiral Stationary Phases Based on N-4-(2,5,6-Trichloro-1,3-Dicyano)-Pheyl Derivatives of L-α-Amino Acids.
Justus Liebigs Annalen der Chemie, 1976, 10, pp. 1739-1752; Neue Bishydrazyle mit Aminsubstituenten.
Liebigs Ann. Chem., 1968, 716, pp. 47-60; Nucleophile Substitution an Chlorierten Mono- and Dicyan-benzolen.
Khimiya Geterotsiklicheskikh Siedinenii, 1979, 5, pp. 616-619.
Chirality, 2000, 12, pp. 73-70.
McIntire et al., "1-Fluoro-2, 4-dinitrobenzene as a Quantitative Reagent for Primary and Secondary Amines," Analytical Chemistry, vol. 25, No. 11 (1953) pp. 1757-1758.
Supplementary Extended European Search Report of European Patent Application No. 06782403.7, 2010.

\* cited by examiner

CYCLIC AMINE COMPOUND

The present application is a US National Stage application of PCT/JP2006/315559, filed Aug. 1, 2006, which in turn claimed the benefit of Japanese application number JP 223462/2005, filed Aug. 1, 2005, each of which is incorporated herein by reference in its entirety.

TECHNICAL FIELD

The present invention relates to a cyclic amine compound useful as an androgen receptor modulator and the like.

BACKGROUND ART

Androgen is synthesized in the testis and adrenal cortex, bound to an androgen receptor in a target organ, and shows various physiological activities. Chemically, any natural androgen belongs to C19 steroid. The major androgen is testosterone mainly synthesized in the testis, which shows strong uptake in a target cell and strong physiological activity. In female, adrenal cortex is a major androgen supply source.

Androgen is involved in the growth and function maintenance of genital organ (prostate, vesicular gland, epididymis, vas deferens and the like), sex differentiation in the embryonic stage, spermatozoon formation, expression of secondary sexual characteristics (induction of masculinization in, for example, muscle-skeleton, voice, fat distribution etc., and the like), promotion of protein elaboration in muscle and the like, bone metabolism and the like. Therefore, shortage of androgen due to testis dysfunction, castration and the like results in insufficient actions mentioned above, thus leading to various diseases and degraded QOL (quality of life). To deal with the situation, a treatment method to supplement androgen is generally employed. Besides testosterone, synthetic androgen showing different balance of androgen action has been studied and put to practical use in clinical situations.

On the other hand, when androgen is involved in the progression of pathology, a treatment to decrease androgen is employed. For example, in androgen dependent prostate cancer, castration and administration of GnRH agonist decrease testosterone and increase a treatment effect.

For supplementing androgen, testosterone and synthetic androgen are generally used. However, they have a steroid skeleton, which places much burden on the liver or shows other steroid hormone action. Therefore, an androgen receptor modulator (particularly agonist) having a non-steroidal skeleton is considered to be useful for the improvement of pathology caused by insufficient androgen action (hypogonadism, male climacteric disorder and the like) and pathology expected to show improvement by the action of androgen (osteoporosis and the like).

It is known that a naphthalene derivative having a pyrrolidine ring has a superior androgen receptor modulator action (patent reference 1). However, this reference does not disclose a pyrrolidinobenzene derivative having a substituent at the 3-position of pyrrolidine ring.

In addition, a benzene derivative having a pyrrolidine ring is known (patent references 2 and 3, non-patent references 1 to 5). However, a compound having a substituent at the 3-position of pyrrolidine ring is not disclosed.

Furthermore, a benzene derivative having a substituent at the 3-position of pyrrolidine ring is known (patent references 4 and 5, non-patent references 6 to 8). However, a description relating to an androgen receptor modulator action is not found.

[patent reference 1] WO 2004/16576
[patent reference 2] JP-A-2002-88073
[patent reference 3] WO 2000/00464
[patent reference 4] US 2004/0083559 B
[patent reference 5] WO 01/54726
[non-patent reference 1] Tetrahedron, 2002, vol. 58, No. 43, p. 8793-8798
[non-patent reference 2] Tetrahedron Letters, 2001, vol. 42, No. 40, p. 7127-7129
[non-patent reference 3] Chirality, 2000, vol. 12, No. 2, p. 63-70
[non-patent reference 4] Journal of Liquid Chromatography & Related Technologies, 2000, vol. 23, No. 8, p. 1203-1215
[non-patent reference 5] Justus Liebigs Annalen der Chemie, 1968, vol. 716, p. 47-60
[non-patent reference 6] Organic Letters, 2005, vol. 7, No. 13, p. 2575-2578
[non-patent reference 7] Journal of Medicinal Chemistry, 1972, vol. 15, p. 827
[non-patent reference 8] Journal of Chemical Society, 1961, p. 189

DISCLOSURE OF THE INVENTION

The present invention aims at providing a compound having a further superior androgen receptor regulating action.

The present inventors have conducted intensive studies in view of the aforementioned problems and found that a cyclic aminobenzene compound represented by the formula (I) unexpectedly has a superior androgen receptor regulating action, which resulted in the completion of the present invention.

Accordingly, the present invention relates to

[1] a compound represented by the formula (I)

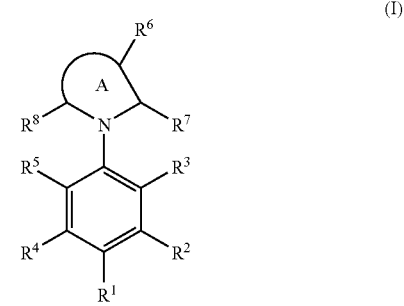

wherein ring A is a 5- to 8-membered ring optionally having further substituent(s) other than $R^6$, $R^7$ and $R^8$,
$R^1$ is an electron-withdrawing group,
$R^2$, $R^3$, $R^4$ and $R^5$ are each independently a hydrogen atom, a halogen atom, a group bonded via a carbon atom, a group bonded via a nitrogen atom, a group bonded via an oxygen atom or a group bonded via a sulfur atom,
$R^6$ is a halogen atom, a group bonded via a carbon atom, a group bonded via a nitrogen atom, a group bonded via an oxygen atom or a group bonded via a sulfur atom,
$R^7$ is a cyano group, a nitro group, an acyl group optionally having substituent(s), an optionally esterified or amidated carboxyl group or a hydrocarbon group optionally having substituent(s), or $R^6$ and $R^7$ optionally form, together with the carbon atom bonded thereto, a ring optionally having substituent(s), and $R^8$ is a hydrogen atom, a halogen atom, a group bonded via a carbon atom, a group bonded via a nitrogen atom, a group bonded via an oxygen atom or a group bonded via a sulfur atom, or a salt thereof;

[2] the compound of the above-mentioned [1], which is represented by the formula (I)

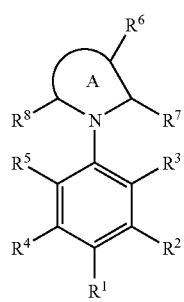

(I)

wherein ring A is a 5- or 6-membered ring optionally having further substituent(s) other than $R^6$, $R^7$ and $R^8$, $R^1$ is an electron-withdrawing group, $R^2$, $R^3$, $R^4$ and $R^5$ are each independently a hydrogen atom, a halogen atom, a group bonded via a carbon atom, a group bonded via a nitrogen atom, a group bonded via an oxygen atom or a group bonded via a sulfur atom, $R^6$ is a halogen atom, a group bonded via a carbon atom, a group bonded via a nitrogen atom, a group bonded via an oxygen atom or a group bonded via a sulfur atom, $R^7$ is an alkyl group optionally having substituent(s), or $R^6$ and $R^7$ optionally form, together with the carbon atom bonded thereto, a ring optionally having substituent(s), and $R^8$ is a hydrogen atom or an alkyl group optionally having substituent(s), provided that (i) 4-[(2S,3S)-2-benzyl-3-phenylpyrrolidin-1-yl]benzonitrile, (ii) tert-butyl 4-[(2S,3S)-2-(4-tert-butylbenzyl)-3-phenylpyrrolidin-1-yl]benzoate, (iii) 4-[(2S,3R)-2-(4-tert-butylbenzyl)-3-methylpyrrolidin-1-yl]benzonitrile, (iv) tert-butyl 4-[(2S,3R)-2-benzyl-3-methylpyrrolidin-1-yl]benzoate, (v) (2R,3S)-2-(hydroxymethyl)-1-(4-nitrophenyl)pyrrolidine-3-ol, (vi) 5-(2-methyl-3-phenylpyrrolidin-1-yl)-2-nitrobenzonitrile, (vii) a compound wherein when ring A is a 5-membered ring, then $R^1$ and $R^3$ should be nitro groups, and (viii) a compound wherein when ring A is a 6-membered ring, then $R^1$ should be an ethoxycarbonyl group, a carboxyl group or an N-monosubstituted carbamoyl group which has benzenesulfonamido as a substituent or nitro group, are excluded;

[3] the compound of the above-mentioned [1], which is represented by the formula (I″)

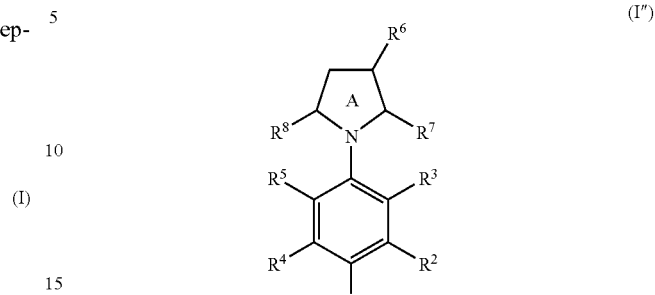

(I″)

wherein ring A is a 5-membered ring optionally having further substituent(s) other than $R^6$, $R^7$ and $R^8$, $R^1$ is an electron-withdrawing group, $R^2$, $R^3$, $R^4$ and $R^5$ are each independently a hydrogen atom, a halogen atom, a group bonded via a carbon atom, a group bonded via a nitrogen atom, a group bonded via an oxygen atom or a group bonded via a sulfur atom, $R^6$ is a halogen atom, a group bonded via a carbon atom, a group bonded via a nitrogen atom, a group bonded via an oxygen atom or a group bonded via a sulfur atom, $R^7$ is an alkyl group optionally having substituent(s), and $R^8$ is a hydrogen atom or an alkyl group optionally having substituent(s), is provided that (i) 4-[(2S,3S)-2-benzyl-3-phenylpyrrolidin-1-yl]benzonitrile, (ii) tert-butyl 4-[(2S,3S)-2-(4-tert-butylbenzyl)-3-phenylpyrrolidin-1-yl]benzoate, (iii) 4-[(2S,3R)-2-(4-tert-butylbenzyl)-3-methylpyrrolidin-1-yl]benzonitrile, (iv) tert-butyl 4-[(2S,3R)-2-benzyl-3-methylpyrrolidin-1-yl]benzoate, (v) (2R,3S)-2-(hydroxymethyl)-1-(4-nitrophenyl)pyrrolidine-3-ol, (vi) 5-(2-methyl-3-phenylpyrrolidin-1-yl)-2-nitrobenzonitrile, and (vii) a compound wherein $R^1$ and $R^3$ are nitro groups are excluded;

[4] the compound of the above-mentioned [I], wherein $R^6$ is a hydroxy group or a group having hydroxy group(s);

[5] the compound of the above-mentioned [1], which is represented by the formula (II)

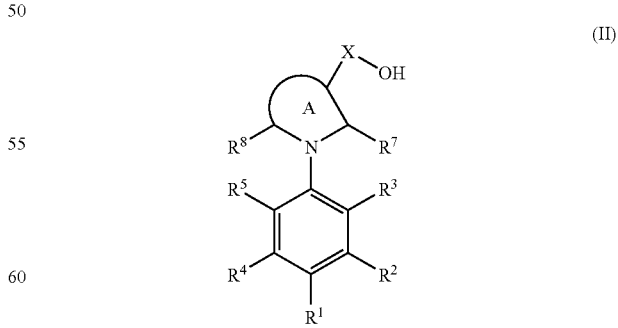

(II)

wherein X is a bond or a linker and other symbols are as defined in the above-mentioned [1];

[6] the compound of the above-mentioned [1], wherein at least two of $R^2$, $R^3$, $R^4$ and $R^5$ are each a halogen atom, a group bonded via a carbon atom, a group bonded via a nitrogen atom, a group bonded via an oxygen atom or a group bonded via a sulfur atom;

[7] the compound of the above-mentioned [5], wherein the linker is $CR^9R^{10}$ ($R^9$ and $R^{10}$ are each independently a hydrogen atom or an alkyl group optionally having substituent(s));

[8] the compound of the above-mentioned [5], wherein $R^1$ is a cyano group, a nitro group, a halogen atom, an acyl group optionally having substituent(s), an optionally esterified or amidated carboxyl group or a $C_{1-6}$ alkyl group substituted with 1 to 5 halogen atoms, $R^2$ is a hydrogen atom, a cyano group, a nitro group, a halogen atom, an acyl group optionally having substituent(s), an optionally esterified or amidated carboxyl group, a $C_{1-6}$ alkyl group optionally substituted with 1 to 5 halogen atoms, a hydroxy group optionally substituted with a $C_{1-6}$ alkyl group or a $C_{1-6}$ alkyl group optionally substituted with hydroxy group(s) optionally having a substituent, $R^3$, $R^4$ and $R^5$ are each a hydrogen atom, a cyano group, a nitro group, a halogen atom, an acyl group optionally having substituent(s), an optionally esterified or amidated carboxyl group, a $C_{1-6}$ alkyl group optionally substituted with 1 to 5 halogen atoms, a hydroxy group optionally substituted with a $C_{1-6}$ alkyl group or a $C_{1-6}$ alkyl group optionally substituted with hydroxy group(s) optionally having a substituent, $R^7$ is a $C_{1-6}$ alkyl group, $R^8$ is a hydrogen atom or a $C_{1-6}$ alkyl group, and X is a bond or a linker represented by $CR^9R^{10}$ wherein $R^9$ is a $C_{1-6}$ alkyl group and $R^{10}$ is a $C_{1-6}$ alkyl group;

[9] the compound of the above-mentioned [5], wherein $R^1$ is a cyano group, $R^2$ is a hydrogen atom, a cyano group, a halogen atom, a $C_{1-6}$ alkyl group substituted with 1 to 5 halogen atoms or a $C_{1-6}$ alkoxy group, $R^3$ is a hydrogen atom, a cyano group, a halogen atom, a $C_{1-6}$ alkyl group substituted with 1 to 5 halogen atoms, a $C_{1-6}$ alkoxy group, a $C_{1-6}$ alkyl group or a $C_{1-6}$ alkyl group substituted with hydroxy group(s), $R^4$ is a hydrogen atom, a halogen atom or a cyano group, $R^5$ is a hydrogen atom, a halogen atom or a $C_{1-6}$ alkyl group, $R^7$ is a $C_{1-6}$ alkyl group, $R^8$ is a hydrogen atom, X is a bond or a linker represented by $CR^9R^{10}$ wherein $R^9$ is a $C_{1-6}$ alkyl group and $R^{10}$ is a $C_{1-6}$ alkyl group;

[10] the compound of the above-mentioned [1], which is selected from
i) 2-chloro-4-[(2S,3S)-3-(1-hydroxy-1-methylethyl)-2-methylpyrrolidin-1-yl]-3-methylbenzonitrile,
ii) 2-chloro-4-[(2S,3S)-3-(1-hydroxy-1-methylethyl)-2-methylpyrrolidin-1-yl]benzonitrile,
iii) 4-[(2S,3S)-3-(1-hydroxy-1-methylethyl)-2-methylpyrrolidin-1-yl]-2-methoxybenzonitrile,
iv) 2-bromo-4-[(2S,3S)-3-(1-hydroxy-1-methylethyl)-2-methylpyrrolidin-1-yl]benzonitrile, and
v) 4-[(2S,3S)-3-hydroxy-2-methylpyrrolidin-1-yl]-3-(trifluoromethyl)benzonitrile;

[11] a prodrug of the compound of the above-mentioned [1];
[12] a pharmaceutical agent comprising the compound of the above-mentioned [1] or a prodrug thereof or a salt thereof;
[13] an androgen receptor agonist comprising a compound of the above-mentioned [1] or a prodrug thereof or a salt thereof;
[14] an agent for the prophylaxis or treatment of hypogonadism, male climacteric disorder, frailty or cachexia, which comprises the compound of the above-mentioned [1] or a prodrug thereof or a salt thereof;
[15] an agent for the prophylaxis or treatment of osteoporosis, which comprises the compound of the above-mentioned [1] or a prodrug thereof or a salt thereof;
[16] an androgen receptor modulator comprising the compound of the above-mentioned [1] or a prodrug thereof or a salt thereof;
[17] a method for the prophylaxis or treatment of hypogonadism, male climacteric disorder, frailty, cachexia or osteoporosis in a mammal, which comprises administering an effective amount of the compound of the above-mentioned [1] or a prodrug thereof or a salt thereof;
[18] use of the compound of the above-mentioned [1] or a prodrug thereof for the production of an agent for the prophylaxis or treatment of hypogonadism, male climacteric disorder, frailty, cachexia or osteoporosis;
[19] an androgen receptor agonist comprising a compound represented by the formula (I')

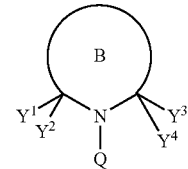

(I')

wherein ring B is a 4- to 10-membered ring further optionally having substituent(s), $Y^1$, $Y^2$, $Y^3$ and $Y^4$ are each independently a hydrogen atom, a halogen atom, a group bonded via a carbon atom, a group bonded via a nitrogen atom, a group bonded via an oxygen atom or a group bonded via a sulfur atom, and Q is a monocyclic aromatic ring group optionally having substituent(s) or a prodrug thereof or a salt thereof;

[20] the agent of the above-mentioned [19], which is an agent for the prophylaxis or treatment of hypogonadism, male climacteric disorder, frailty, cachexia or osteoporosis;

[21] the agent of the above-mentioned [19] or [20], wherein $Y^1$, $Y^2$, $Y^3$ and $Y^4$ are each independently a hydrogen atom or an alkyl group optionally having substituent(s);

[22] a method for the prophylaxis or treatment of hypogonadism, male climacteric disorder, frailty, cachexia or osteoporosis, which comprises administering, to a mammal, an effective amount of a compound represented by the formula (I')

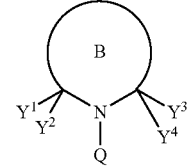

(I')

wherein ring B is a 4- to 10-membered ring further optionally having substituent(s), $Y^1$, $Y^2$, $Y^3$ and $Y^4$ are each independently a hydrogen atom, a halogen atom, a group bonded via a carbon atom, a group bonded via a nitrogen atom, a group bonded via an oxygen atom or a group bonded via a sulfur atom, and Q is a monocyclic aromatic ring group optionally having substituent(s) or a prodrug thereof or a salt thereof;

[23] the method of the above-mentioned [22], wherein $Y^1$, $Y^2$, $Y^3$ and $Y^4$ are each independently a hydrogen atom or an alkyl group optionally having substituent(s);

[24] use of a compound represented by the formula (I')

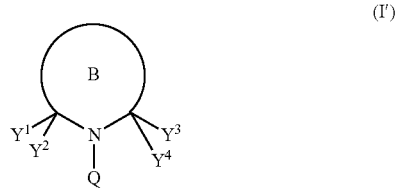

wherein ring B is a 4- to 10-membered ring further optionally having substituent(s), $Y^1$, $Y^2$, $Y^3$ and $Y^4$ are each independently a hydrogen atom, a halogen atom, a group bonded via a carbon atom, a group bonded via a nitrogen atom, a group bonded via an oxygen atom or a group bonded via a sulfur atom, and Q is a monocyclic aromatic ring group optionally having substituent(s) or a prodrug thereof or a salt thereof, for the production of an agent for the prophylaxis or treatment of hypogonadism, male climacteric disorder, frailty, cachexia or osteoporosis; and

[25] the use of the above-mentioned [24], wherein $Y^1$, $Y^2$, $Y^3$ and $Y^4$ are each independently a hydrogen atom or an alkyl group optionally having substituent(s); and the like.

Moreover, the present invention also relates to

[1'] a compound represented by the formula (I)

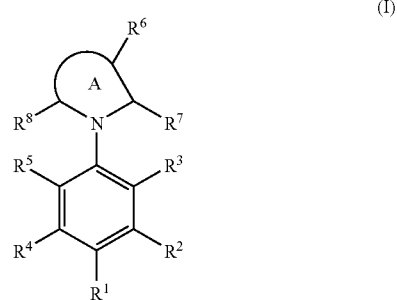

wherein ring A is a 5- or 6-membered ring optionally having further substituent(s) other than $R^6$, $R^7$ and $R^8$,
$R^1$ is an electron-withdrawing group,
$R^2$, $R^3$, $R^4$ and $R^5$ are each independently a hydrogen atom, a halogen atom, a group bonded via a carbon atom, a group bonded via a nitrogen atom, a group bonded via an oxygen atom or a group bonded via a sulfur atom,
$R^6$ is a halogen atom, a group bonded via a carbon atom, a group bonded via a nitrogen atom, a group bonded via an oxygen atom or a group bonded via a sulfur atom,
$R^7$ is an alkyl group optionally having substituent(s), or
$R^6$ and $R^7$ optionally form, together with the carbon atom bonded thereto, a ring optionally having substituent(s), and
$R^8$ is a hydrogen atom or an alkyl group optionally having substituent(s) or a salt thereof;
[2'] an androgen receptor agonist comprising the compound of the above-mentioned [1'] or a prodrug thereof or a salt thereof;
[3'] an agent for the prophylaxis or treatment of hypogonadism, male climacteric disorder, frailty or cachexia, which comprises the compound of the above-mentioned [1'] or a prodrug thereof or a salt thereof;
[4'] an agent for the prophylaxis or treatment of osteoporosis, which comprises the compound of the above-mentioned [1'] or a prodrug thereof or a salt thereof;
[5'] an androgen receptor modulator comprising the compound of the above-mentioned [1'] or a prodrug thereof or a salt thereof;
[6'] a method for the prophylaxis or treatment of hypogonadism, male climacteric disorder, frailty, cachexia or osteoporosis, which comprises administering, to a mammal, an effective amount of the compound of the above-mentioned [1'] or a prodrug thereof or a salt thereof;
[7'] use of the compound of the above-mentioned [1'] or a prodrug thereof for the production of an agent for the prophylaxis or treatment of hypogonadism, male climacteric disorder, frailty, cachexia or osteoporosis; and the like.

DETAILED DESCRIPTION OF THE INVENTION

The "5- to 8-membered ring" for ring A is not particularly limited and, for example, a saturated or unsaturated non-aromatic heterocycle (aliphatic heterocycle) containing, as ring-constituting atom (ring atom), at least one nitrogen atom and optionally containing further, besides the nitrogen atom, 1 to 4, preferably 1 or 2, hetero atoms of 1 to 3 kinds (preferably 1 or 2 kinds) selected from an oxygen atom, a sulfur atom, a nitrogen atom and the like, and the like are used.

Of these, a 5- or 6-membered saturated or unsaturated non-aromatic heterocycle containing 1 or 2 nitrogen atoms is preferable. Particularly, a 5-membered saturated non-aromatic heterocycle containing one nitrogen atom is preferable.

Alternatively, a 6-membered saturated or unsaturated non-aromatic heterocycle containing 1 or 2 nitrogen atoms is preferable.

As the "saturated or unsaturated non-aromatic heterocycle (aliphatic heterocycle)", for example, saturated non-aromatic heterocycles such as pyrrolidine, oxazolidine, thiazolidine, piperidine, piperazine, morpholine, thiomorpholine, homopiperidine, homopiperazine, homomorpholine, thiohomomorpholine, hexahydroazepine, hexahydro-1,4-diazepine, hexahydro-1,4-oxazepine, hexahydro-1,4-thiazepine, azacyclooctane, 1,4-diazacyclooctane, 1,5-diazacyclooctane, 1-aza-4-oxacyclooctane, 1-aza-5-oxacyclooctane, 1-aza-4-thiacyclooctane, 1-aza-5-thiacyclooctane and the like, unsaturated non-aromatic heterocycles such as 2-pyrroline, 3-pyrroline, 1,4-dihydropyridine, 1,2-dihydropyridine, 1,2,3,4-tetrahydropyridine, 1,2,3,6-tetrahydropyridine, 2,3-dihydro-1H-azepine, 2,5-dihydro-1H-azepine, 2,3,4,5-tetrahydro-1H-azepine, 2,3,4,7-tetrahydro-1H-azepine, 2,3,4,5-tetrahydro-4H-1,4-oxazepine, 2,3,4,5-tetrahydro-4H-1,4-thiazepine, azacyclooct-3-ene, azacyclooct-4-ene, 1,4-diazacyclooctane, 1,5-diazacyclooctane, 1-aza-4-oxacyclooct-6-ene, 1-aza-4-thiacyclooct-6-ene and the like, and the like can be used.

The substituent that the "5- to 8-membered ring" for ring A further optionally has besides $R^6$, $R^7$ and $R^8$ is not particularly limited. For example,
(i) a hydrocarbon group optionally having substituent(s) (e.g., alkyl group optionally having substituent(s), alkenyl group optionally having substituent(s), an alkynyl group optionally having substituent(s), aryl group optionally having substituent(s), aralkyl group optionally having substituent(s), cycloalkyl group optionally having substituent(s), cycloalkenyl group optionally having substituent(s), cycloalkanedienyl group optionally having substituent(s) and the like),
(ii) a heterocyclic group optionally having substituent(s),
(iii) an amino group optionally having substituent(s),
(iv) an imidoyl group optionally having substituent(s) (e.g., a group represented by the formula —C(U')═N—U wherein U and U' are each independently a hydrogen atom or a substituent (wherein U is preferably a hydrogen atom) and the like), (v) an amidino group optionally having substituent(s) (e.g., a group represented by the formula —C(NE'E")=N-E wherein E, E' and E" are each independently a hydrogen atom or a substituent (wherein E is preferably a hydrogen atom) and the like),
(vi) a hydroxy group optionally having a substituent,
(vii) a thiol group optionally having a substituent,
(viii) an alkylsulfinyl group optionally having substituent(s),
(ix) an optionally esterified or amidated carboxyl group,
(x) a thiocarbamoyl group optionally having substituent(s),
(xi) a sulfamoyl group optionally having substituent(s),
(xii) a halogen atom (e.g., fluorine atom, chlorine atom, bromine atom, iodine atom),
(xiii) a cyano group,
(xiv) an isocyano group,
(xv) a cyanate group,
(xvi) an isocyanate group,
(xvii) a thiocyanate group,
(xviii) an isothiocyanate group,
(xix) a nitro group,
(xx) a nitroso group,
(xxi) an acyl group optionally having substituent(s) (e.g., an acyl group derived from carboxylic acid optionally having substituent(s), an acyl group derived from sulfonic acid optionally having substituent(s)),
(xxii) an oxo group,
(xxiii) a thioxo group,
(xxiv) a $C_{1-4}$ alkylenedioxy group
and the like (hereinafter to be abbreviated as substituent group A) can be used. These optional substituents may be present in the number of 1 to acceptable maximum number, preferably 1 to 5, more preferably 1 to 3, and particularly preferably 1 or 2, at substitutable position(s) of ring A.

As the "hydrocarbon group" of the "hydrocarbon group is optionally having substituent(s)" in substituent group A, for example, "aliphatic chain hydrocarbon group", "alicyclic hydrocarbon group", "aromatic hydrocarbon group", "aromatic hydrocarbon-aliphatic chain hydrocarbon group" and the like are used.

As the "aliphatic chain hydrocarbon group", for example, a linear or branched chain aliphatic hydrocarbon group such as an alkyl group, an alkenyl group, an alkynyl group and the like are used.

As the "alicyclic hydrocarbon group", for example, a saturated or unsaturated, monocyclic or condensed polycyclic alicyclic hydrocarbon group such as a cycloalkyl group, a cycloalkenyl group, a cycloalkanedienyl group or a bicyclic or tricyclic fused ring wherein these and a $C_{6-14}$ aryl ring (e.g., benzene) and the like are condensed, and the like are used.

As the "aromatic hydrocarbon group", a monocyclic or condensed polycyclic aromatic hydrocarbon group is used. While the group is not particularly limited, it is preferably a $C_{6-22}$ aromatic hydrocarbon group, more preferably a $C_{6-18}$ aromatic hydrocarbon group, further preferably a $C_{6-14}$ aromatic hydrocarbon group, and particularly preferably a $C_{6-10}$ aromatic hydrocarbon group and the like. Specifically, for example, phenyl, o-tolyl, m-tolyl, p-tolyl, 2,3-xylyl, 2,4-xylyl, mesityl, o-cumenyl, m-cumenyl, p-cumenyl, o-biphenyl, m-biphenyl, p-biphenyl, 1-naphthyl, 2-naphthyl, 2-indenyl, 2-s anthryl, azulenyl, phenanthryl, fluorenyl and the like are preferable, and of these, phenyl, 1-naphthyl, 2-naphthyl, 2-anthryl and the like are preferable.

The "aromatic hydrocarbon-aliphatic chain hydrocarbon group" means a group formed by substitution of 1 to 3, the above-mentioned aromatic hydrocarbon groups at any position(s) on the above-mentioned aliphatic chain hydrocarbon group. Specific examples include an aralkyl group such as benzyl, phenethyl, naphthylmethyl, α-methylbenzyl, benzhydryl and the like.

As the substituent of the "hydrocarbon group", for example, a lower alkoxy group (e.g., $C_{1-6}$ alkoxy such as methoxy, ethoxy, propoxy and the like), a halogen atom (e.g., fluorine atom, chlorine atom, bromine atom, iodine atom), a lower alkyl group (e.g., $C_{1-6}$ alkyl such as methyl, ethyl, propyl and the like), a lower alkenyl group (e.g., $C_{2-6}$ alkenyl such as vinyl, allyl and the like), a lower alkynyl group (e.g., $C_{2-6}$ alkynyl such as ethynyl, propargyl and the like), an amino group optionally having substituent(s), a hydroxy group optionally having a substituent, a cyano group, an amidino group optionally having substituent(s), a carboxyl group, a lower alkoxycarbonyl group (e.g., $C_{1-6}$ alkoxycarbonyl such as methoxycarbonyl, ethoxycarbonyl and the like), an N-monosubstituted carbamoyl group, an N,N-disubstituted carbamoyl group, a cyclic carbamoyl group (e.g., 1-azetidinylcarbonyl, 1-pyrrolidinylcarbonyl, piperidinocarbonyl, morpholinocarbonyl, 1-piperazinylcarbonyl and the like) and the like (hereinafter to be abbreviated as substituent group B) are used, where 1 to 3 optional substituents therefrom may be present at any substitutable position(s).

As the "amino group optionally having substituent(s)", "hydroxy group optionally having a substituent", "amidino group optionally having substituent(s)", N-monosubstituted carbamoyl group and N,N-disubstituted carbamoyl group as the substituent of the "hydrocarbon group optionally having substituent(s)", those similar to the below-mentioned groups are used.

As the "alkyl group" of the "alkyl group optionally having substituent(s)" in substituent group A, for example, a $C_{1-6}$ alkyl group such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl and the like, and the like are used. Here, as the substituent for the alkyl group, one selected from the aforementioned substituent group B can be used, where 1 to 3 optional substituents therefrom may be present at any substitutable position(s).

As the "alkenyl group" of the "alkenyl group optionally having substituent(s)" in substituent group A, for example, a $C_{2-6}$ alkenyl group such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like, and the like are used. Here, as the substituent for the alkenyl group, one selected from the aforementioned substituent group B can be used, where 1 to 3 optional substituents therefrom may be present at any substitutable position(s).

As the "alkynyl group" of the "alkynyl group optionally having substituent(s)" in substituent group A, for example, a $C_{2-6}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like, and the like are used. Here, as the substituent for the alkynyl group, one selected from the aforementioned substituent group B can be used, where 1 to 3 optional substituents therefrom may be present at any substitutable position(s).

As the "aryl group" of the "aryl group optionally having substituent(s)" in substituent group A, for example, $C_{6-14}$ aryl group such as phenyl, naphthyl, anthryl, phenanthryl, acenaphthyl and the like, and the like are used. Here, as the substituent for the "aryl group", one selected from the aforementioned substituent group B can be used, where 1 to 3 optional substituents therefrom may be present at any substitutable position(s).

As the "aralkyl group" of the "aralkyl group optionally having substituent(s)" in substituent group A, for example, a $C_{7-11}$ aralkyl group such as benzyl, phenethyl, naphthylmethyl and the like, and the like are used. Here, as the substituent for the aralkyl group, one selected from the aforementioned substituent group B can be used, where 1 to 3 optional substituents therefrom may be present at any substitutable position(s).

As the "cycloalkyl group" of the "cycloalkyl group optionally having substituent(s)" in substituent group A, for example, a $C_{3-10}$ cycloalkyl group such as cyclopropyl, cyclobutyl, cyclopentyl, cyclohexyl, cycloheptyl, cyclooctyl, cyclononyl and the like, preferably a $C_{3-7}$ cycloalkyl group, and the like are used. Here, as the substituent for the "cycloalkyl group", one selected from the aforementioned substituent group B can be used, where 1 to 3 optional substituents therefrom may be present at any substitutable position(s).

As the "cycloalkenyl group" of the "cycloalkenyl group optionally having substituent(s)" in substituent group A, for example, a $C_{3-10}$ cycloalkenyl group such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl and the like, preferably $C_{3-7}$ cycloalkenyl group, and the like are used. Here, as the substituent for the "cycloalkenyl group", one selected from the aforementioned substituent group B can be used, where 1 to 3 optional substituents therefrom may be present at any substitutable position(s).

As the "cycloalkanedienyl group" of the "cycloalkanedienyl group optionally having substituent(s)" in substituent group A, for example, a $C_{4-6}$ cycloalkanedienyl group such as 2,4-cyclopentadien-1-yl, 2,4-cyclohexadien-1-yl, 2,5-cyclohexadien-1-yl and the like, and the like are used. Here, as the substituent for the "cycloalkanedienyl group", one selected from the aforementioned substituent group B can be used, where 1 to 3 optional substituents therefrom may be present at any substitutable position(s).

As the "heterocyclic group" of the "heterocyclic group optionally having substituent(s)" in substituent group A, for example, an aromatic heterocycle or a saturated or unsaturated non-aromatic heterocycle (aliphatic heterocycle) containing, as ring-constituting atom (ring atom), at least one, preferably 1 to 4, more preferably 1 or 2, hetero atoms of 1 to 3 kinds (preferably 1 or 2 kinds) selected from an oxygen atom, a sulfur atom, a nitrogen atom and the like are used.

As the "aromatic heterocyclic group", for example, a 5- or 6-membered monocyclic aromatic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like and, for example, a 8- to 12-membered condensed polycyclic aromatic heterocyclic group such as benzofuranyl, isobenzofuranyl, benzo[b]thienyl, indolyl, isoindolyl, 1H-indazolyl, benzindazolyl, benzooxazolyl, 1,2-benzoisooxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acrydinyl, phenoxazinyl, phenothiazinyl, phenazinyl, phenoxathiinyl, thianthrenyl, phenanthridinyl, phenathrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like, and the like are used.

As the "nonaromatic heterocyclic group", for example, a 3- to 8-membered (preferably 5- or 6-membered) saturated or unsaturated (preferably saturated) nonaromatic heterocyclic group (aliphatic heterocyclic group) such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl and the like, and the like, or a nonaromatic heterocyclic group wherein the double bond of the aforementioned monocyclic aromatic heterocyclic group or condensed polycyclic aromatic heterocyclic group is partly or entirely saturated such as 1,2,3,4-tetrahydroquinolyl, 1,2,3,4-tetrahydroisoquinolyl and the like, and the like are used.

As the "substituent" of the "heterocyclic group optionally having substituent(s)", for example, a lower alkyl group (e.g., a $C_{1-6}$ alkyl group such as methyl, ethyl, propyl and the like), a lower alkenyl group (e.g., a $C_{2-6}$ alkenyl group such as vinyl, allyl and the like), a lower alkynyl group (e.g., a $C_{2-6}$ alkynyl group such as ethynyl, propargyl and the like), an acyl group (e.g., a $C_{1-6}$ alkanoyl such as formyl, acetyl, propionyl, pivaloyl and the like, benzoyl and the like), an amino group optionally having substituent(s), a hydroxy group optionally having a substituent, a halogen atom (e.g., fluorine atom, chlorine atom, bromine atom, iodine atom), an imidoyl group optionally having substituent(s), an amidino group optionally having substituent(s) and the like (hereinafter to be abbreviated as substituent group C) are used. 1 to 5 (preferably 1 to 3) of these optional substituents may be present at substitutable position(s). As the "amino group optionally having substituent(s)", "hydroxy group optionally having a substituent", "imidoyl group optionally having substituent(s)" and "amidino group optionally having substituent(s)" as the substituent of the "heterocyclic group optionally having substituent(s)", 1 to 5 (preferably 1 to 3) of below-mentioned groups may be present at substitutable position(s).

As the "substituent" of the "amino group optionally having substituent(s)", "imidoyl group optionally having substituent(s)", "amidino group optionally having substituent(s)", "hydroxy group optionally having a substituent" and "thiol group optionally having a substituent" in substituent group A, for example, (i) a lower alkyl group (e.g., a $C_{1-6}$ alkyl group such as methyl, ethyl, propyl, isopropyl, butyl, isobutyl, tert-butyl, pentyl, hexyl and the like) optionally substituted with substituent(s) selected from halogen atom, hydroxy, carboxyl, cyano, nitro, optionally halogenated $C_{1-6}$ alkoxy (e.g., methoxy, ethoxy, trifluoromethoxy, 2,2,2-trifluoroethoxy, trichloromethoxy, 2,2,2-trichloroethoxy etc.), formyl, optionally halogenated $C_{1-6}$ alkylcarbonyl, optionally halogenated $C_{1-6}$ alkoxycarbonyl, $C_{7-11}$ alkylaryl (for example, o-toluoyl, m-toluoyl, p-toluoyl, xylyl, mesityl, preferably $C_{1-5}$ alkyl-phenyl) and the like, (ii) an acyl group [for example, formyl, $C_{1-6}$ alkanoyl (e.g., acetyl, propionyl, pivaloyl), benzoyl, $C_{1-6}$ alkylsulfonyl (e.g., methanesulfonyl), benzenesulfonyl, optionally halogenated $C_{1-6}$ alkoxycarbonyl group (e.g., methoxycarbonyl, ethoxycarbonyl, trifluoromethoxycarbonyl, 2,2,2-trifluoroethoxycarbonyl, trichloromethoxycarbonyl, 2,2,2-trichloroethoxycarbonyl), $C_{1-6}$ alkoxycarbonyl group optionally substituted with phenyl group (e.g., benzyloxycarbonyl) and the like], (iii) an aryl group (e.g., a $C_{6-10}$ aryl such as phenyl, 1-naphthyl, 2-naphthyl and the like, etc.), (iv) an aralkyl group (e.g., a $C_{7-10}$ aralkyl such as benzyl, phenethyl and the like, preferably phenyl-$C_{1-4}$ alkyl etc.), (v) an arylalkenyl group (e.g., $C_{8-10}$ arylalkenyl such as cinnamyl and the like, preferably phenyl-$C_{2-4}$ alkenyl), (vi) a heterocyclic group optionally substituted with substituent(s) selected from halogen atom, hydroxy, carboxyl, cyano, nitro, optionally halogenated $C_{1-6}$ alkoxy (e.g., methoxy, ethoxy, trifluoromethoxy, 2,2,2-trifluoroethoxy, trichloromethoxy, 2,2,2-trichloroethoxy etc.), formyl, optionally halogenated $C_{1-6}$ alkylcarbonyl, optionally halogenated $C_{1-6}$ alkoxycarbonyl, $C_{6-10}$ aryl (e.g., phenyl, 1-naphthyl, 2-naphthyl), $C_{7-10}$ aralkyl (e.g., benzyl, phenethyl), $C_{7-11}$ alkylaryl (for example, o-toluoyl, m-toluoyl, p-toluoyl, xylyl, mesityl, preferably $C_{1-5}$ alkyl-phenyl) and the like (as the heterocyclic group, those similar to the heterocyclic group of the "heterocyclic group optionally having substituent(s)" in the aforementioned substituent group A are used), and the like are used. 1 or 2 of these optional substituents may be present at substitutable position(s).

In addition, the "amino group" of the "amino group optionally having substituent(s)" in substituent group A may be substituted by an imidoyl group optionally having substituent(s) (e.g., $C_{1-6}$ alkylimidoyl (e.g., formimidoyl, acetimidoyl), $C_{1-6}$ alkoxyimidoyl, $C_{1-6}$ alkylthioimidoyl, amidino and the like), an amino group optionally substituted with 1 or 2 $C_{1-6}$ alkyl groups and the like. 1 or 2 of these optional substituents may be present at substitutable position(s). Here, as the "imidoyl group optionally having substituent(s)", those similar to the "imidoyl group optionally having substituent(s)" in the substituent group A are used, where any 1 to 3 substituents may be present at substitutable position(s).

In addition, two substituents may form a cyclic amino group together with a nitrogen atom. As such cyclic amino group, for example, 1-azetidinyl, 1-pyrrolidinyl, piperidino, thiomorpholino, morpholino, 1-piperazinyl, a 3- to 8-membered (preferably 5- or 6-membered) cyclic amino (e.g., 1-piperazinyl, 1-pyrrolyl, 1-imidazolyl) optionally having lower alkyl (e.g., $C_{1-6}$ alkyl such as methyl, ethyl, propyl, isopropyl, butyl, tert-butyl, pentyl, hexyl and the like), aralkyl (e.g., $C_{7-10}$ aralkyl such as benzyl, phenethyl and the like), aryl (e.g., $C_{6-10}$ aryl such as phenyl, 1-naphthyl, 2-naphthyl and the like) and the like at the 4-position and the like, and the like are used.

As the "alkylsulfinyl group" of the "alkylsulfinyl group optionally having substituent(s)" in substituent group A, for example, a $C_{1-6}$ alkylsulfinyl group such as methylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl, hexylsulfinyl and the like, and the like are used. Here, as the substituent of the "alkylsulfinyl group", substituents selected from the aforementioned substituent group B are used, where 1 to 3 optional substituents therefrom may be present at any substitutable position(s).

As the "optionally esterified or amidated carboxyl group" in substituent group A, a carboxyl group, an alkoxycarbonyl group optionally having substituent(s), an aryloxycarbonyl group optionally having substituent(s), an aralkyloxycarbonyl group optionally having substituent(s), a carbamoyl group, an N-monosubstituted carbamoyl group, an N,N-disubstituted carbamoyl group and the like are used.

As the "alkoxycarbonyl group", for example, lower ($C_{1-6}$) alkoxycarbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl and the like and the like are used. Of these, $C_{1-3}$ alkoxycarbonyl such as methoxycarbonyl, ethoxycarbonyl, propoxycarbonyl and the like are preferably used.

As the "aryloxycarbonyl group", for example, $C_{6-14}$ aryloxycarbonyl such as phenoxycarbonyl, 1-naphthoxycarbonyl, 2-naphthoxycarbonyl, 1-phenanthoxycarbonyl and the like, and the like are used.

As the "aralkyloxycarbonyl group", for example, $C_{7-14}$ aralkyloxycarbonyl group such as benzyloxycarbonyl, phenethyloxycarbonyl and the like (preferably $C_{6-10}$ aryl-$C_{1-4}$ alkoxy-carbonyl group), and the like are used.

As the substituent for "alkoxycarbonyl group", "aryloxycarbonyl group" and "aralkyloxycarbonyl group", for example, hydroxy, amino optionally having substituent(s) [the substituent for the amino is, for example, 1 or 2 from lower alkyl (e.g., $C_{1-6}$ alkyl such as methyl, ethyl, propyl, isopropyl, butyl, isobutyl, tert-butyl, pentyl, hexyl and the like, preferably methyl, ethyl) optionally substituted with 1 to 5 halogen atoms (for example, fluorine atom, chlorine atom, bromine atom, iodine atom), acyl (e.g., $C_{1-6}$ alkanoyl such as formyl, acetyl, propionyl, pivaloyl and the like, benzoyl), carboxyl, $C_{1-6}$ alkoxycarbonyl and the like], a halogen atom (for example, fluorine, chlorine, bromine, iodine), a nitro group, a cyano group, lower alkoxy (for example, $C_{1-6}$ alkoxy such as methoxy, ethoxy, n-propoxy, isopropoxy, n-butoxy, isobutoxy, sec-butoxy, tert-butoxy and the like, preferably methoxy, ethoxy) optionally substituted with 1 to 5 halogen atoms (for example, fluorine, chlorine, bromine, iodine) and the like are used. These substituents are the same or different and each is preferably substituted by 1 to 3 (preferably 1 or 2) substituents.

As the substituent of the "N-monosubstituted carbamoyl group", for example, lower alkyl (e.g., $C_{1-6}$ alkyl such as methyl, ethyl, propyl, isopropyl, butyl, isobutyl, tert-butyl, pentyl, hexyl and the like), lower alkenyl (e.g., $C_{2-6}$ alkenyl such as vinyl, allyl, isopropenyl, propenyl, butenyl, pentenyl, hexenyl and the like), cycloalkyl (e.g., $C_{3-6}$ cycloalkyl such as cyclopropyl, cyclobutyl, cyclopentyl, cyclohexyl and the like), aryl (e.g., $C_{6-10}$ aryl such as phenyl, 1-naphthyl, 2-naphthyl and the like), aralkyl (e.g., $C_{7-10}$ aralkyl such as benzyl, phenethyl and the like, preferably phenyl-$C_{1-4}$ alkyl), arylalkenyl (e.g., $C_{8-10}$ arylalkenyl such as cinnamyl and the like, preferably phenyl-$C_{2-4}$ alkenyl etc.), a heterocyclic group (for example, those similar to the "heterocyclic group" of the "heterocyclic group optionally having substituent(s)" in substituent group A) and the like are used. These lower alkyl, lower alkenyl, cycloalkyl, aryl, aralkyl, arylalkenyl and heterocyclic group may have a substituent, where a similar number of substituents similar to the substituents that the aforementioned "alkoxycarbonyl group", "aryloxycarbonyl group" and "aralkyloxycarbonyl group" may have are used.

The "N,N-disubstituted carbamoyl group" means a carbamoyl group having 2 substituents on a nitrogen atom. Examples for the one substituent include those similar to the substituents for the aforementioned "N-monosubstituted carbamoyl group". Examples for another include lower alkyl (e.g., $C_{1-6}$ alkyl such as methyl, ethyl, propyl, isopropyl, butyl, tert-butyl, pentyl, hexyl and the like), $C_{3-7}$ cycloalkyl (e.g., cyclopropyl, cyclobutyl, cyclopentyl, cyclohexyl), $C_{7-10}$ aralkyl (e.g., benzyl, phenethyl and the like, preferably phenyl-$C_{1-4}$ alkyl) and the like.

In addition, two substituents may form cyclic amino together with a nitrogen atom. As such cyclic carbamoyl, for example, 3- to 8-membered (preferably 5- or 6-membered) cyclic aminocarbonyl such as 1-azetidinylcarbonyl, 1-pyrrolidinylcarbonyl, piperidinocarbonyl, morpholinocarbonyl, 1-piperazinylcarbonyl and 1-piperazinylcarbonyl optionally having lower alkyl (e.g., $C_{1-6}$ alkyl such as methyl, ethyl, propyl, isopropyl, butyl, tert-butyl, pentyl, hexyl and the like), aralkyl (e.g., $C_{7-10}$ aralkyl such as benzyl, phenethyl and the like), aryl (e.g., $C_{6-10}$ aryl such as phenyl, 1-naphthyl, 2-naphthyl and the like) and the like at the 4-position and the like, and the like are used.

As the "substituent" of the "thiocarbamoyl group optionally having substituent(s) (N-monosubstituted thiocarbamoyl group, N,N-disubstituted thiocarbamoyl group)" and "sulfamoyl group optionally having substituent(s) (N-monosubstituted sulfamoyl group, N,N-disubstituted sulfamoyl group)" in substituent group A, a similar number of substituents similar to the substituents for the "N-monosubstituted carbamoyl group" and "N,N-disubstituted carbamoyl group" of the aforementioned "optionally esterified or amidated carboxyl group" can be used.

As the "acyl group optionally having substituent(s)" in substituent group A, an "acyl group derived from carboxylic acid and optionally having substituent(s)", an "acyl group derived from sulfonic acid and optionally having substituent(s)" and the like are used. As the "acyl group derived from carboxylic acid", for example, a group wherein a hydrogen atom or one substituent that the aforementioned "N-monosubstituted carbamoyl group" has on the nitrogen atom and carbonyl are bonded and the like are used. As the "acyl group derived from sulfonic acid", for example, a group wherein one substituent that the aforementioned "N-monosubstituted carbamoyl group" has on the nitrogen atom and sulfonyl are bonded and the like are used.

More specifically, as the acyl group, for example, an acyl group derived from carboxylic acid such as
(i) a formyl,
(ii) a lower ($C_{1-6}$)alkanoyl group such as acetyl, propionyl, butyryl, isobutyryl, valeryl, isovaleryl, pivaloyl, hexanoyl and the like;
(iii) a lower ($C_{3-7}$)alkenoyl group such as acryloyl, methacryloyl, crotonoyl, isocrotonoyl and the like;
(iv) a $C_{4-7}$ cycloalkanecarbonyl group such as a cyclopropanecarbonyl group, a cyclobutanecarbonyl group, a cyclopentanecarbonyl group, a cyclohexanecarbonyl group and the like;
(v) a $C_{7-14}$ aroyl group such as benzoyl, p-toluoyl, 1-naphthoyl, 2-naphthoyl and the like;
(vi) a $C_{6-10}$ aryl lower ($C_{2-4}$)alkanoyl group such as phenylacetyl, phenylpropionyl, hydratropoyl, phenylbutyryl and the like;
(vii) a $C_{6-10}$ aryl lower ($C_{3-5}$)alkenoyl group such as cinnamoyl, atropoyl and the like, and the like, or
an acyl group derived from sulfonic acid such as
(i) $C_{1-6}$ alkylsulfonyl such as methanesulfonyl, ethanesulfonyl, propanesulfonyl and the like, and the like;
(ii) a $C_{6-10}$ arenesulfonyl group such as benzenesulfonyl, p-toluenesulfonyl group and the like, are used.

As the substituent for the "acyl group", substituents selected from the aforementioned substituent group B are used, where 1 to 3 optional substituents therefrom may be present at any substitutable position(s).

As the "$C_{1-4}$ alkylenedioxy group" in substituent group A, a methylenedioxy group, an ethylenedioxy group, a propylenedioxy group, a butylenedioxy group and the like are used, which may be present on the same carbon or different carbons.

The "electron-withdrawing group" for $R^1$ means a group which generally tends to attract an electron from the other on the basis of hydrogen in a molecule, and is not particularly limited as long as it is used for organic chemistry. For example, a cyano group, a nitro group, a halogen atom (e.g., fluorine atom, chlorine atom, bromine atom, iodine atom), an acyl group optionally having substituent(s), an optionally esterified or amidated carboxyl group or a $C_{1-6}$ alkyl group substituted with 1 to 5 halogen atoms and the like are used. Particularly, an electron-withdrawing group via a carbon atom (e.g., a cyano group, an acyl group optionally having substituent(s), an optionally esterified or amidated carboxyl group, a $C_{1-6}$ alkyl group substituted with 1 to 5 halogen atoms and the like) is preferable. Particularly, a cyano group, a nitro group, an acyl group optionally having substituent(s), an optionally esterified or amidated carboxyl group or a $C_{1-6}$ alkyl group substituted with 1 to 5 halogen atoms and the like are preferable, a cyano group, an acyl group optionally having substituent(s) (particularly an acetyl group optionally having substituent(s), a methanesulfonyl group optionally having substituent(s), an ethanesulfonyl group optionally having substituent(s)), an optionally esterified or amidated carboxyl group (particularly an alkoxycarbonyl group optionally having substituent(s) (e.g., a methoxycarbonyl group, an ethoxycarbonyl group, a propoxycarbonyl group)) and a $C_{1-6}$ alkyl group (particularly methyl, ethyl) substituted with 1 to 5 halogen atoms are more preferable, and a cyano group is particularly preferable.

As the "acyl group optionally having substituent(s)" as an electron-withdrawing group, those similar to the "acyl group optionally having substituent(s)" in substituent group A are used. Particularly, an acetyl group, a methanesulfonyl group and an ethanesulfonyl group are preferable.

As the "optionally esterified or amidated carboxyl group", those similar to the "optionally esterified or amidated carboxyl group" in substituent group A are used. Particularly, an alkoxycarbonyl group optionally having substituent(s) is preferable, and as the alkoxycarbonyl group, a methoxycarbonyl group, an ethoxycarbonyl group and a propoxycarbonyl group are particularly preferable.

As the "$C_{1-6}$ alkyl group substituted with 1 to 5 halogen atoms", for example, a $C_{1-6}$ alkyl group (e.g., methyl, ethyl, propyl, isopropyl, butyl, isobutyl, sec-butyl, tert-butyl, pentyl, hexyl and the like) substituted with 1 to 5, preferably 1 to 3, a halogen atoms (e.g., fluorine atom, chlorine atom, bromine atom, iodine atom) and the like are used. Specifically, fluoromethyl, chloromethyl, difluoromethyl, trichloromethyl, trifluoromethyl, 1-fluoroethyl, 2-bromoethyl, 2,2,2-trifluoroethyl, pentafluoroethyl, 2-fluoropropyl, 1,2-difluoropropyl, 3,3,3-trifluoropropyl, 1-fluorobutyl, 4,4,4-trifluorobutyl, 1-fluoropentyl, 5,5,5-trifluoropentyl, 1-fluorohexyl, 3,3-difluorohexyl, 6,6,6-trifluorohexyl and the like can be used. Of these, trichloromethyl, trifluoromethyl, 2,2,2-trifluoroethyl and pentafluoroethyl are preferable, and trifluoromethyl is particularly preferable.

As the "halogen atom" for $R^2$, $R^3$, $R^4$ or $R^5$, a fluorine atom, a chlorine atom, a bromine atom and an iodine atom are used.

As the "group bonded via a carbon atom" for $R^2$, $R^3$, $R^4$ or $R^5$, for example, a cyano group, a hydrocarbon group optionally having substituent(s), an acyl group derived from carboxylic acid and optionally having substituent(s), an optionally esterified or amidated carboxyl group, an imidoyl group optionally having substituent(s), an amidino group optionally having substituent(s), a thiocarbamoyl group optionally having substituent(s), an optionally substituted heterocyclic group bonded via a carbon atom and the like are used.

As the "group bonded via a nitrogen atom" for $R^2$, $R^3$, $R^4$ or $R^5$, a nitro group, a nitroso group, an amino group optionally having substituent(s), an isocyano group, an isocyanate group, an isothiocyanate group, an optionally substituted heterocyclic group bonded via a nitrogen atom and the like are used.

As the "group bonded via an oxygen atom" for $R^2$, $R^3$, $R^4$ or $R^5$, a hydroxy group optionally having a substituent, an oxo group, a cyanate group and the like are used.

As the "group bonded via a sulfur atom" for $R^2$, $R^3$, $R^4$ or $R^5$, for example, thiol group optionally having a substituent, alkylsulfinyl group optionally having substituent(s), an acyl group derived from sulfonic acid and optionally having substituent(s), sulfamoyl group optionally having substituent(s), thiocyanate group, thioxo group, an optionally substituted heterocyclic group bonded via a sulfur atom and the like are used.

As these "hydrocarbon group optionally having substituent(s)", "acyl group derived from carboxylic acid and optionally having substituent(s)", "optionally esterified or amidated carboxyl group", "imidoyl group optionally having substituent(s)", "amidino group optionally having substituent(s)", "amino group optionally having substituent(s)", "hydroxy group optionally having a substituent", "thiol group optionally having a substituent", "alkylsulfinyl group optionally having substituent(s)", "acyl group derived from sulfonic acid and optionally having substituent(s)", "thiocarbamoyl group optionally having substituent(s)" or "sulfamoyl group optionally having substituent(s)", those similar to the groups exemplified for substituent group A are used.

As the "optionally substituted heterocyclic group" of the "optionally substituted heterocyclic group bonded via a carbon atom", "optionally substituted heterocyclic group bonded via a nitrogen atom" or "optionally substituted heterocyclic group bonded via a sulfur atom", those similar to the "heterocyclic group optionally having substituent(s)" for substituent group A are used.

As the "halogen atom, group bonded via a carbon atom, group bonded via a nitrogen atom, group bonded via an oxygen atom or group bonded via a sulfur atom" for $R^2$, $R^3$, $R^4$ or $R^5$, the groups in substituent group A except a $C_{1-4}$ alkylenedioxy group can be used.

As $R^2$, $R^3$, $R^4$ or $R^5$, a hydrogen atom, a cyano group, a nitro group, a halogen atom, an acyl group optionally having substituent(s), an optionally esterified or amidated carboxyl group, a hydrocarbon group optionally having substituent(s) or a hydroxy group optionally having a substituent is preferable.

Of these, as $R^2$, $R^3$, $R^4$ or $R^5$, a hydrogen atom, a cyano group, a nitro group, a halogen atom, an acyl group optionally having substituent(s), an optionally esterified or amidated carboxyl group, a $C_{1-6}$ alkyl group optionally substituted with 1 to 5 halogen atoms, a hydroxy group optionally substituted with a $C_{1-6}$ alkyl group, a $C_{1-6}$ alkyl group optionally substituted with hydroxy group(s) optionally having a substituent and the like are preferable.

Particularly, a hydrogen atom, a cyano group, a halogen atom (particularly chlorine atom, fluorine atom, bromine atom), a $C_{1-6}$ alkyl group (particularly methyl), a $C_{1-6}$ alkyl group substituted with 1 to 5 halogen atoms (particularly trifluoromethyl group), a $C_{1-6}$ alkyl group substituted with hydroxy group(s) (particularly hydroxymethyl group), a $C_{1-6}$ alkoxy group (particularly methoxy) and the like are preferable.

As the "halogen atom", "group bonded via a nitrogen atom", "group bonded via an oxygen atom" and "group bonded via a sulfur atom" for $R^6$, those similar to the "halogen atom", "group bonded via a nitrogen atom", "group bonded via an oxygen atom" and "group bonded via a sulfur atom" for $R^2$, $R^3$, $R^4$ or $R^5$ can be used.

As the "group bonded via a carbon atom" for $R^6$, for example, a cyano group, a hydrocarbon group optionally having substituent(s), an acyl group derived from carboxylic acid and optionally having substituent(s), an optionally esterified or amidated carboxyl group, an imidoyl group optionally having substituent(s), an amidino group optionally having substituent(s), a thiocarbamoyl group optionally having substituent(s), an optionally substituted heterocyclic group bonded via a carbon atom and the like are used.

As the "acyl group derived from carboxylic acid and optionally having substituent(s)", "optionally esterified or amidated carboxyl group", "imidoyl group optionally having substituent(s)", "amidino group optionally having substituent(s)", "thiocarbamoyl group optionally having substituent(s)", "optionally substituted heterocyclic group bonded via a carbon atom" of the "group bonded via a carbon atom" for $R^6$, those similar to the "acyl group derived from carboxylic acid and optionally having substituent(s)", "optionally esterified or amidated carboxyl group", "imidoyl group optionally having substituent(s)", "amidino group optionally having substituent(s)", "thiocarbamoyl group optionally having substituent(s)", "optionally substituted heterocyclic group bonded via a carbon atom" of the "group bonded via a carbon atom" for $R^2$, $R^3$, $R^4$ or $R^5$ can be used.

As the "hydrocarbon group" of the "hydrocarbon group optionally having substituent(s)" of the "group bonded via a carbon atom" for $R^6$, those similar to the "hydrocarbon group" of the below-mentioned "hydrocarbon group optionally having substituent(s)" for $R^7$ can be used. Preferred is the "hydrocarbon group" of the "hydrocarbon group optionally having substituent(s)" in substituent group A.

As the "substituent" of the "hydrocarbon group optionally having substituent(s)" of the "group bonded via a carbon atom" for $R^6$, a substituent selected from substituent group A is used, and a substituent selected from substituent group B is preferably used. These optional substituents in the number of 1 to acceptable maximum number, preferably 1 to 5, more preferably 1 to 3, and particularly preferably 1 or 2 may be present at substitutable position(s) of hydrocarbon group.

As $R^6$, a hydroxy group or a group having hydroxy group(s) and the like are preferable.

The "group having hydroxy group(s)" for $R^6$ is not particularly limited as long as it is a group having at least one hydroxy group in a molecule. For example, a "group bonded via a carbon atom", a "group bonded via a nitrogen atom", a "group bonded via an oxygen atom" or a "group bonded via a sulfur atom" for $R^6$, which has at least one hydroxy group can be used and a group represented by the below-mentioned —X—OH and the like are preferably used.

As the "acyl group optionally having substituent(s)" and "optionally esterified or amidated carboxyl group" for $R^7$, those similar to the "acyl group optionally having substituent(s)" and "optionally esterified or amidated carboxyl group" in substituent group A are used.

As the "hydrocarbon group" of the "hydrocarbon group optionally having substituent(s)" for $R^7$, an "aliphatic chain hydrocarbon group", an "alicyclic hydrocarbon group", an "aromatic hydrocarbon group", an "aromatic hydrocarbon-aliphatic chain hydrocarbon group" and the like are used.

As the "aliphatic chain hydrocarbon group" for $R^7$, for example, a linear or branched chain aliphatic hydrocarbon group such as an alkyl group, an alkenyl group, an alkynyl group and the like are used.

As the "alkyl group" for $R^7$, for example, a $C_{1-10}$ alkyl group such as methyl, ethyl, n-propyl, isopropyl, n-butyl, isobutyl, sec-butyl, tert-butyl, n-pentyl, isopentyl, neopentyl, n-hexyl, isohexyl, 1,1-dimethylbutyl, 2,2-dimethylbutyl, 3,3-dimethylbutyl, 3,3-dimethylpropyl, 2-ethylbutyl, n-heptyl, 1-methylheptyl, 1-ethylhexyl, n-octyl, 1-methylheptyl, nonyl and the like, and the like are used. Of these, $C_{1-6}$ alkyl (e.g., methyl, ethyl, n-propyl, isopropyl, n-butyl, sec-butyl, tert-butyl and the like) and the like are preferable.

As the "alkenyl group" for $R^7$, for example, a $C_{2-6}$ alkenyl group such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like, and the like are used.

As the "alkynyl group" for $R^7$, for example, a $C_{2-6}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like, and the like are used.

As the "alicyclic hydrocarbon group" for $R^7$, for example, a saturated or unsaturated, monocyclic or condensed polycyclic alicyclic hydrocarbon group such as a cycloalkyl group, a cycloalkenyl group, a cycloalkanedienyl group or a bicyclic or tricyclic fused ring wherein these and a $C_{6-14}$ aryl ring (e.g., benzene) and the like are condensed, and the like are used.

As the "cycloalkyl group" for $R^7$, for example, a $C_{3-10}$ cycloalkyl group such as cyclopropyl, cyclobutyl, cyclopentyl, cyclohexyl, cycloheptyl, cyclooctyl, cyclononyl and the like, preferably a $C_{3-7}$ cycloalkyl group and the like are used.

As the "cycloalkenyl group" for $R^7$, for example, a $C_{3-10}$ cycloalkenyl group such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl and the like, preferably a $C_{3-7}$ cycloalkenyl group and the like are used.

As the "cycloalkanedienyl group" for $R^7$, for example, a $C_{4-6}$ cycloalkanedienyl group such as 2,4-cyclopentadien-1-yl, 2,4-cyclohexadien-1-yl, 2,5-cyclohexadien-1-yl and the like, and the like are used.

As the "aromatic hydrocarbon group" for $R^7$, a monocyclic or condensed polycyclic aromatic hydrocarbon group is used. While the group is not particularly limited, it is preferably a $C_{6-22}$ aromatic hydrocarbon group, more preferably a $C_{6-18}$ aromatic hydrocarbon group, more preferably a $C_{6-14}$ aromatic hydrocarbon group, particularly preferably a $C_{6-10}$ aromatic hydrocarbon group and the like. Specifically, for example, phenyl, o-tolyl, m-tolyl, p-tolyl, 2,3-xylyl, 2,4-xylyl, mesityl, o-cumenyl, m-cumenyl, p-cumenyl, o-biphenyl, m-biphenyl, p-biphenyl, 1-naphthyl, 2-naphthyl, 2-indenyl, 2-anthryl, azulenyl, phenanthryl, fluorenyl and the like can be used, and phenyl, 1-naphthyl, 2-naphthyl, 2-anthryl and the like are particularly preferable.

The "aromatic hydrocarbon-aliphatic chain hydrocarbon group" for $R^7$ means a group formed by substituting the above-mentioned aliphatic chain hydrocarbon group with 1 to 3, the above-mentioned aromatic hydrocarbon groups. Specifically, for example, a $C_{7-15}$ aralkyl group such as benzyl, phenethyl, naphthylmethyl, α-methylbenzyl, benzhydryl and the like, preferably a $C_{7-11}$ aralkyl group can be used.

As the "substituent" of the "hydrocarbon group optionally having substituent(s)" for $R^7$, a substituent selected from substituent group A is used. These optional substituents in the number of 1 to acceptable maximum number, preferably 1 to 5, more preferably 1 to 3, and particularly preferably 1 or 2 may be present at substitutable position(s) of hydrocarbon group.

In addition, $R^6$ and $R^7$ may form a ring optionally having substituent(s) together with the carbon atom bonded thereto.

As the "ring" of the "ring optionally having substituent(s)" for $R^6$ and $R^7$, "alicyclic hydrocarbon", "non-aromatic heterocycle" and the like are used.

As the "alicyclic hydrocarbon group" for the "ring" formed by $R^6$ and $R^7$, for example, a saturated or unsaturated, monocyclic or condensed polycyclic alicyclic hydrocarbon group such as a cycloalkyl group, a cycloalkenyl group, a cycloalkanedienyl group or a bicyclic or tricyclic fused ring wherein these and a $C_{6-14}$ aryl ring (e.g., benzene) and the like are condensed, and the like are used.

As the "cycloalkane" of the "ring" formed by $R^6$ and $R^7$, for example, $C_{3-10}$ cycloalkane such as cyclopropane, cyclobutane, cyclopentane, cyclohexane, cycloheptane, cyclooctane, cyclononane and the like, preferably $C_{3-7}$ cycloalkane, and the like are used.

As the "cycloalkene" of the "ring" formed by $R^6$ and $R^7$, for example, $C_{3-10}$ cycloalkene such as cyclopropene, cyclobutene, cyclopentene, cyclohexene and the like, preferably $C_{3-7}$ cycloalkene and the like, are used.

As the "cycloalkandiene" of the "ring" formed by $R^6$ and $R^7$, for example, $C_{4-6}$ cycloalkandiene such as cyclopentadiene, cyclohexadiene and the like, and the like are used.

As the "non-aromatic heterocycle" of the "ring" formed by $R^6$ and $R^7$, for example, a saturated or unsaturated non-aromatic heterocycle containing, as ring-constituting atom (ring atom), at least one, preferably 1 to 4, more preferably 1 or 2, hetero atoms of 1 to 3 kinds (preferably 1 or 2 kinds) selected from an oxygen atom, a sulfur atom, a nitrogen atom and the like are used. As the "non-aromatic heterocycle", for example, a 3- to 8-membered (preferably 5- or 6-membered) saturated or unsaturated (preferably saturated) non-aromatic heterocycle (aliphatic heterocycle) such as oxirane, azetidine, oxetane, thietane, pyrrolidine, tetrahydrofuran, thioran, piperidine, tetrahydropyran, morpholine, thiomorpholine, piperazine and the like, and the like, or a nonaromatic heterocycle wherein the double bond of the aforementioned monocyclic aromatic heterocycle or condensed polycyclic aromatic heterocycle group is partly or entirely saturated such as 1,2,3,4-tetrahydroquinoline, 1,2,3,4-tetrahydroisoquinoline and the like, and the like are used.

As the "ring optionally having substituent(s)" formed by $R^6$ and $R^7$, an alicyclic hydrocarbon optionally having substituent(s) is preferable, cycloalkane optionally having substituent(s) is more preferable, and cyclopentane, cyclohexane or cycloheptane each of which optionally has substituent(s) is particularly preferable.

As the "substituent" of the "ring optionally having substituent(s)" formed by $R^6$ and $R^7$, the aforementioned substituent selected from substituent group A are used, where 1 to 3 optional substituents therefrom may be present at any substitutable position(s).

As $R^7$, an alkyl group optionally having substituent(s) is preferable.

As the "alkyl group" of the "alkyl group optionally having substituent(s)" for preferable $R^7$, for example, a $C_{1-10}$ alkyl group such as methyl, ethyl, n-propyl, isopropyl, n-butyl, isobutyl, sec-butyl, tert-butyl, n-pentyl, isopentyl, neopentyl, n-hexyl, isohexyl, 1,1-dimethylbutyl, 2,2-dimethylbutyl, 3,3-dimethylbutyl, 3,3-dimethylpropyl, 2-ethylbutyl, n-heptyl, 1-methylheptyl, 1-ethylhexyl, n-octyl, 1-methylheptyl, nonyl and the like, and the like are used. Of these, $C_{1-6}$ alkyl (e.g., methyl, ethyl, n-propyl, isopropyl, n-butyl, sec-butyl, tert-butyl and the like) and the like are preferable. As the substituent of the "alkyl group", the aforementioned substituent selected from substituent group A is used, where 1 to 3 optional substituents therefrom may be present at any substitutable position(s).

As $R^7$, a $C_{1-6}$ alkyl group (e.g., methyl, ethyl, isopropyl) and the like are more preferable, and a methyl group and an isopropyl group are particularly preferable.

As the "halogen atom", "group bonded via a nitrogen atom", "group bonded via an oxygen atom", "group bonded via a sulfur atom" for R$^8$, those similar to the "halogen atom", "group bonded via a nitrogen atom", "group bonded via an oxygen atom" and "group bonded via a sulfur atom" for R$^2$, R$^3$, R$^4$ or R$^5$ can be used. As the "group bonded via a carbon atom" for R$^8$, for example, a cyano group, a hydrocarbon group optionally having substituent(s), an acyl group derived from carboxylic acid and optionally having substituent(s), an optionally esterified or amidated carboxyl group, an imidoyl group optionally having substituent(s), an amidino group optionally having substituent(s), a thiocarbamoyl group optionally having substituent(s), an optionally substituted heterocyclic group bonded via a carbon atom and the like are used.

As the "acyl group derived from carboxylic acid and optionally having substituent(s)", "optionally esterified or amidated carboxyl group", "imidoyl group optionally having substituent(s)", "amidino group optionally having substituent(s)", "thiocarbamoyl group optionally having substituent(s)" and "optionally substituted heterocyclic group bonded via a carbon atom" of the "group bonded via a carbon atom" for R$^8$, those similar to the "acyl group derived from carboxylic acid and optionally having substituent(s)", "optionally esterified or amidated carboxyl group", "imidoyl group optionally having substituent(s)", "amidino group optionally having substituent(s)", "thiocarbamoyl group optionally having substituent(s)", "optionally substituted heterocyclic group bonded via a carbon atom" exemplified as the "group bonded via a carbon atom" for R$^2$, R$^3$, R$^4$ or R$^5$ can be used.

As the "hydrocarbon group optionally having substituent(s)" of the "group bonded via a carbon atom" for R$^8$, those similar to the "hydrocarbon group optionally having substituent(s)" for R$^7$ can be used.

As the "substituent" of the "hydrocarbon group optionally having substituent(s)" of the "group bonded via a carbon atom" for R$^8$, a substituent selected from substituent group A is used. These 1 to 3 optional substituents may be present at substitutable position(s) of the hydrocarbon group.

As R$^8$, a hydrogen atom or an alkyl group optionally having substituent(s) is preferable.

Here, as the "alkyl group" of the "alkyl group optionally having substituent(s)" for preferable R$^8$, for example, a C$_{1-10}$ alkyl group such as methyl, ethyl, n-propyl, isopropyl, n-butyl, isobutyl, sec-butyl, tert-butyl, n-pentyl, isopentyl, neopentyl, n-hexyl, isohexyl, 1,1-dimethylbutyl, 2,2-dimethylbutyl, 3,3-dimethylbutyl, 3,3-dimethylpropyl, 2-ethylbutyl, n-heptyl, 1-methylheptyl, 1-ethylhexyl, n-octyl, 1-methylheptyl, nonyl and the like, and the like are used. Of these, C$_{1-6}$ alkyl (e.g., methyl, ethyl, n-propyl, isopropyl, n-butyl, sec-butyl, tert-butyl and the like) and the like are preferable. As the substituent of the "alkyl group", a substituent selected from the aforementioned substituent group A is used, where 1 to 3 optional substituents therefrom may be present at any substitutable position(s).

As R$^8$, a hydrogen atom, a C$_{1-6}$ alkyl group (e.g., methyl, ethyl) and the like are more preferable, a hydrogen atom is particularly preferable.

As compound (I), a compound wherein at least two of R$^2$, R$^3$, R$^4$ and R$^5$ are each a halogen atom, a group bonded via a carbon atom (e.g., a cyano group, an acyl group derived from carboxylic acid and optionally having substituent(s), an optionally esterified or amidated carboxyl group, a C$_{1-6}$ alkyl group optionally substituted with 1 to 5 halogen atoms and the like), a group bonded via a nitrogen atom (e.g., a nitro group), a group bonded via an oxygen atom (e.g., a C$_{1-6}$ alkoxy group) or a group bonded via a sulfur atom is preferable, particularly a compound wherein R$^2$ and R$^3$ are each a halogen atom, a group bonded via a carbon atom (e.g., a cyano group, an acyl group derived from carboxylic acid and optionally having substituent(s), an optionally esterified or amidated carboxyl group, a C$_{1-6}$ alkyl group optionally substituted with 1 to 5 halogen atoms and the like), a group bonded via a nitrogen atom (e.g., a nitro group), a group bonded via an oxygen atom (e.g., a C$_{1-6}$ alkoxy group) or a group bonded via a sulfur atom is preferable.

[Explanation of Compound (II)]

As the "linker" for X, (i) a divalent hydrocarbon group optionally having substituent(s) (preferably an alkylene group), (ii) a divalent heterocyclic group optionally having substituent(s), (iii) —O—, (iv) —S(O)n$^1$— (n$^1$ is an integer of 0 to 2), (v) —NR$^{13}$— (R$^{13}$ is a hydrogen atom, a hydrocarbon group optionally having substituent(s) or a heterocyclic group optionally having substituent(s)), or (vi) a group wherein two or more (for example, 2 to 5, preferably 2 or 3) thereof are combined, and the like are used.

As the "divalent hydrocarbon group" of the "divalent hydrocarbon group optionally having substituent(s)", for example, an alkylene group, an alkenylene group, an alkynylene group, or a group obtained by removing two hydrogen atoms from one carbon atom of cyclic hydrocarbon, a group obtained by removing one hydrogen atom from each of two carbon atoms of cyclic hydrocarbon and the like are used.

As the alkylene group, for example, a C$_{1-6}$ alkylene group such as methylene, ethylene, propylene and the like, and the like are used. Of these, methylene is preferable.

As the alkenylene group, for example, a C$_{2-6}$ alkenylene, group such as —CH=CH—, —CH=CH—CH$_2$—, —CH$_2$—CH=CH—CH$_2$—, —(CH$_2$)$_2$—CH=CH—CH$_2$—, —(CH$_2$)$_2$—CH=CH—(CH$_2$)$_2$—, —(CH$_2$)$_3$—CH=CH—CH$_2$— and the like, and the like are used.

As the alkynylene group, for example, a C$_{2-6}$ alkynylene group such as —C≡C—CH$_2$—, —CH$_2$—C≡C—CH$_2$—, —(CH$_2$)$_2$—C≡C—CH$_2$—, —(CH$_2$)$_2$—C≡C—(CH$_2$)$_2$—, —(CH$_2$)$_3$—C≡C—CH$_2$— and the like, and the like are used.

As the group obtained by removing two hydrogen atoms from one carbon atom of cyclic hydrocarbon, or the group obtained by removing one hydrogen atom from each of two carbon atoms of cyclic hydrocarbon, for example, a group obtained by removing two hydrogen atoms from one carbon atom of a C$_{6-14}$ aryl ring (e.g., benzene, naphthalene and the like), C$_{3-8}$ cycloalkane (e.g., cyclopropane, cyclobutane, cyclopentane, cyclohexane and the like) and the like, or a group obtained by removing one hydrogen atom from each of two carbon atoms of cyclic hydrocarbon and the like are used. Specifically, cyclopropane-1,1-diyl, cyclobutane-1,1-diyl, 1,4-phenylene, 1,4-cyclohexylene and the like are used.

As the "divalent heterocyclic group" of the "divalent heterocyclic group optionally having substituent(s)", for example, a group obtained by removing two hydrogen atoms from one atom (carbon atom or hetero atom) of heterocycle, group obtained by removing one hydrogen atom from each of two atoms (carbon atom or hetero atom) of heterocycle and the like are used.

As the "heterocyclic group", those similar to the "heterocyclic group" of the "heterocyclic group optionally having substituent(s)" in substituent group A are used.

As the substituent of the "divalent hydrocarbon group" or "divalent heterocyclic group", a similar number of substituents similar to the substituent selected from the aforementioned substituent group A are used. Particularly, "an alkyl group optionally having substituent(s)" is preferable.

As the "hydrocarbon group optionally having substituent(s)" for $R^{13}$, those similar to the "hydrocarbon group optionally having substituent(s)" in substituent group A are used.

As the "heterocyclic group optionally having substituent(s)" for $R^{13}$, those similar to the "heterocyclic group optionally having substituent(s)" in substituent group A are used.

As the linker for X, an alkylene group optionally having substituent(s) is preferably. Particularly, $CR^9R^{10}$ ($R^9$ and $R^{10}$ are each a hydrogen atom or an alkyl group optionally having substituent(s)) and the like are preferable.

In addition, X is also preferably a bond.

As the "alkyl group" of the "alkyl group optionally having substituent(s)" for $R^9$ or $R^{10}$, for example, a $C_{1-10}$ alkyl group such as methyl, ethyl, n-propyl, isopropyl, n-butyl, isobutyl, sec-butyl, tert-butyl, n-pentyl, isopentyl, neopentyl, n-hexyl, isohexyl, 1,1-dimethylbutyl, 2,2-dimethylbutyl, 3,3-dimethylbutyl, 3,3-dimethylpropyl, 2-ethylbutyl, n-heptyl, 1-methylheptyl, 1-ethylhexyl, n-octyl, 1-methylheptyl, nonyl and the like, and the like are used. Particularly, $C_{1-6}$ alkyl (e.g., methyl, ethyl, n-propyl, isopropyl, n-butyl, sec-butyl, tert-butyl and the like) and the like are preferable.

As the substituent of the "alkyl group", a similar number of substituents similar to the substituent selected from the aforementioned substituent group A are used.

As each of $R^9$ and $R^{10}$, a $C_{1-6}$ alkyl group (e.g., methyl, ethyl) and the like are preferable, and a methyl group is particularly preferable.

While the configuration of the substituent of the compound (II) of the present invention is not particularly limited, the absolute configuration of $R^7$ for compound (II) is preferable as shown in the formula (III) or a salt thereof.

The formula (III).

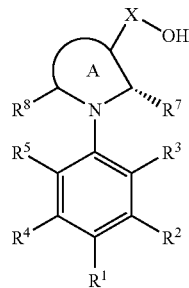

(III)

As compound (I), compound (II) is preferable, compound (III) is particularly preferable, and a compound wherein X is a bond or $CR^9R^{10}$ ($R^9$ and $R^{10}$ are as mentioned above) is more preferable.

As a preferable compound, a compound wherein ring A is a pyrrolidine ring or a piperidine ring,
$R^1$ is a cyano group, a nitro group, a halogen atom, an acyl group optionally having substituent(s), an optionally esterified or amidated carboxyl group or a $C_{1-6}$ alkyl group substituted with 1 to 5 halogen atoms,
$R^2$, $R^3$, $R^4$ and $R^5$ are each a hydrogen atom, a cyano group, a nitro group, a halogen atom, an acyl group optionally having substituent(s), an optionally esterified or amidated carboxyl group, a $C_{1-6}$ alkyl group optionally substituted with 1 to 5 halogen atoms, a hydroxyl group optionally substituted with a $C_{1-6}$ alkyl group or a $C_{1-6}$ alkyl group optionally substituted with hydroxy group(s) optionally having a substituent,
$R^7$ is a $C_{1-6}$ alkyl group,
$R^8$ is a hydrogen atom or a $C_{1-6}$ alkyl group, and
X is a bond or $CR^9R^{10}$ wherein $R^9$ is a $C_{1-6}$ alkyl group and $R^{10}$ is a $C_{1-6}$ alkyl group is preferable.

Particularly, a compound wherein
ring A is a pyrrolidine ring or a piperidine ring,
$R^1$ is a cyano group,
$R^2$ is a hydrogen atom, a cyano group, a halogen atom (e.g., chlorine atom, fluorine atom, bromine atom), a $C_{1-6}$ alkoxy group (e.g., methoxy group) or a $C_{1-6}$ alkyl group (e.g., methyl group) substituted with 1 to 5 halogen atoms (e.g., fluorine atom),
$R^3$ is a hydrogen atom, a cyano group, a halogen atom (e.g., chlorine atom, fluorine atom), a $C_{1-6}$ alkyl group (e.g., methyl, ethyl), a $C_{1-6}$ alkoxy group (e.g., methoxy group), a $C_{1-6}$ alkyl group substituted with 1 to 5 halogen atoms (e.g., a trifluoromethyl group) or a $C_{1-6}$ alkyl group substituted with hydroxy group(s) (e.g., $CH_2OH$),
$R^4$ is a hydrogen atom, a halogen atom (e.g., fluorine atom) or a cyano group,
$R^5$ is a hydrogen atom, a halogen atom (e.g., fluorine atom) or a $C_{1-6}$ alkyl group (e.g., methyl),
$R^7$ is a $C_{1-6}$ alkyl group (e.g., methyl, isopropyl),
$R^8$ is a hydrogen atom, and
X is a bond or $CR^9R^{10}$ wherein $R^9$ is a methyl group and $R^{10}$ is a methyl group is more preferable.

Particularly preferable compounds (I) include
i) 2-chloro-4-[(2S,3S)-3-(1-hydroxy-1-methylethyl)-2-methylpyrrolidin-1-yl]-3-methylbenzonitrile,
ii) 2-chloro-4-[(2S,3S)-3-(1-hydroxy-1-methylethyl)-2-methylpyrrolidin-1-yl]benzonitrile,
iii) 4-[(2S,3S)-3-(1-hydroxy-1-methylethyl)-2-methylpyrrolidin-1-yl]-2-methoxybenzonitrile,
iv) 2-bromo-4-[(2S,3S)-3-(1-hydroxy-1-methylethyl)-2-methylpyrrolidin-1-yl]benzonitrile, and
v) 4-[(2S,3S)-3-hydroxy-2-methylpyrrolidin-1-yl]-3-(trifluoromethyl)benzonitrile.

Moreover, the present invention also encompasses an androgen receptor agonist containing a compound represented by the formula (I')

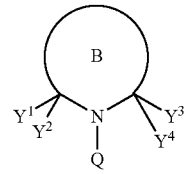

(I')

wherein ring B is a 4- to 10-membered ring further optionally having substituent(s), $Y^1$, $Y^2$, $Y^3$ and $Y^4$ are each independently a hydrogen atom, a halogen atom, a group bonded via a carbon atom, a group bonded via a nitrogen atom, a group bonded via an oxygen atom or a group bonded via a sulfur atom, and Q is a monocyclic aromatic ring group optionally having substituent(s) [hereinafter to be referred to as compound (I')] or a prodrug thereof or a salt thereof.

The androgen receptor agonist is preferably an agent for the prophylaxis or treatment of hypogonadism, male climacteric disorder, frailty, cachexia or osteoporosis.

$Y^1$, $Y^2$, $Y^3$ and $Y^4$ are each preferably a hydrogen atom or an alkyl group optionally having substituent(s).

[Explanation of Compound (I')]

As the "4- to 10-membered ring" of the "4- to 10-membered ring optionally having substituent(s)" for ring B, a 4- to 10-membered ring optionally containing, besides nitrogen atom bonded to Q, at least one, preferably 1 to 4, more preferably 1 or 2, hetero atoms of 1 to 3 kinds (preferably 1 or 2 kinds) selected from an oxygen atom, a sulfur atom, a nitrogen atom and the like are used.

As such ring, for example, a 5-membered monocyclic nitrogen-containing aromatic heterocycle such as pyrrolyl, imidazolyl, pyrazolyl, 1,2,3-triazolyl, 1,2,4-triazolyl, tetrazolyl and the like; for example, a 8- to 10-membered condensed polycyclic nitrogen-containing aromatic heterocyclic group such as indolyl, isoindolyl, 1H-indazolyl, benzindazolyl, 1H-benzotriazolyl, purinyl and the like; for example, a 4- to 8-membered (preferably 5- or 6-membered) saturated or unsaturated (preferably saturated) nonaromatic nitrogen-containing heterocycle (aliphatic nitrogen-containing heterocycle) such as azetidinyl, pyrrolidinyl, piperidyl, morpholinyl, thiomorpholinyl, piperazinyl and the like, or a nonaromatic nitrogen-containing heterocycle wherein the double bond of the aforementioned monocyclic nitrogen-containing aromatic heterocycle or condensed polycyclic nitrogen-containing aromatic heterocycle is partly or entirely saturated such as 1,2,3,4-tetrahydroquinolyl, 1,2,3,4-tetrahydroisoquinolyl and the like, and the like are used.

The "4 to 10-membered ring" optionally further has substituent(s) other than $Y^1, Y^2, Y^3$ and $Y^4$. As such substituent, a similar number of substituents similar to the substituent selected from substituent group A are used. As the "halogen atom", "group bonded via a carbon atom", "group bonded via a nitrogen atom", "group bonded via an oxygen atom" and "group bonded via a sulfur atom" for $Y^1, Y^2, Y^3$ or $Y^4$, those similar to the "halogen atom", "group bonded via a carbon atom", "group bonded via a nitrogen atom", "group bonded via an oxygen atom" and "group bonded via a sulfur atom" for $R^8$ are used.

As $Y^1, Y^2, Y^3$ or $Y^4$, a hydrogen atom or an alkyl group optionally having substituent(s) is preferable.

As the "monocyclic aromatic ring group" of the "monocyclic aromatic ring group optionally having substituent(s)" for Q, for example, (i) phenyl group, or (ii) a 5- to 8-membered (preferably 5- or 6-membered) monocyclic aromatic heterocyclic group containing, as ring-constituting atom (ring atom), at least one, preferably 1 to 4, more preferably 1 or 2, hetero atoms of 1 to 3 kinds (preferably 1 or 2 kinds) selected from an oxygen atom, a sulfur atom, a nitrogen atom and the like, and the like are used.

As the "monocyclic aromatic heterocyclic group", for example, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like are used.

As the substituent of the "monocyclic aromatic ring", a similar number of substituents similar to the substituent selected from substituent group A are used.

As compound (I'), compound (I) is preferable.

Furthermore, the present invention encompasses

[26] a compound represented by the formula (IV)

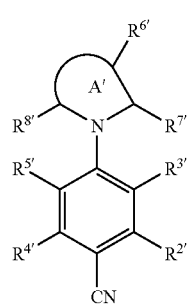

(IV)

wherein $R^{2'}, R^{3'}, R^{4'}$ and $R^{5'}$ are each independently a hydrogen atom, a halogen atom, a group bonded via a carbon atom, a group bonded via a nitrogen atom, a group bonded via an oxygen atom or a group bonded via a sulfur atom, $R^{6'}$ a group bonded via a carbon atom, a group bonded via a nitrogen atom, a group bonded via an oxygen atom or a group bonded via a sulfur atom, $R^{7'}$ is a cyano group, a nitro group, an acyl group optionally having substituent(s), an optionally esterified or amidated carboxyl group or a hydrocarbon group optionally having substituent(s), or $R^{6'}$ and $R^{7'}$ may form a ring optionally having substituent(s) together with the carbon atom bonded thereto, $R^{8'}$ is a hydrogen atom, a halogen atom, a group bonded via a carbon atom, a group bonded via a nitrogen atom, a group bonded via an oxygen atom or a group bonded via a sulfur atom, ring A' is a 5- to 8-membered ring optionally having substituent(s) other than $R^{6'}, R^{7'}$ and $R^{8'}$ [hereinafter to be also referred to as compound (IV)], or a salt thereof;

[27] the compound of the above-mentioned [26], which is represented by the formula (IV)

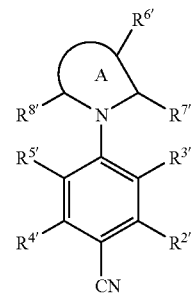

(IV)

wherein ring A is a 5- or 6-membered ring optionally further having substituent(s) other than $R^{6'}, R^{7'}$ and $R^{8'}$, $R^{2'}, R^{3'}, R^{4'}$ and $R^{5'}$ are each independently a hydrogen atom, a halogen atom, a group bonded via a carbon atom, a group bonded via a nitrogen atom, a group bonded via an oxygen atom or a group bonded via a sulfur atom, $R^{6'}$ is a halogen atom, a group bonded via a carbon atom, a group bonded via a nitrogen atom, a group bonded via an oxygen atom or a group bonded via a sulfur atom, $R^{7'}$ is an alkyl group optionally having substituent(s), or $R^{6'}$ and $R^{7'}$ may form a ring optionally having substituent(s) together with the carbon atom bonded thereto, and $R^{8'}$ is a hydrogen atom or an alkyl group optionally having substituent(s), provided that (i) 4-[(2S,3S)-2-benzyl-3-phenylpyrrolidin-1-yl]benzonitrile and (iii) 4-[(2S,3R)-2-(4-tert-butylbenzyl)-3-methylpyrrolidin-1-yl]benzonitrile are excluded;

[28] the compound of the above-mentioned [26], which is represented by the formula (IV')

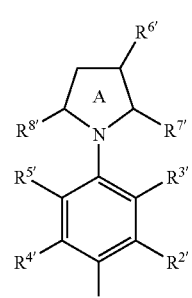

(IV')

wherein ring A is a 5-membered ring optionally further having substituent(s) other than $R^{6'}$, $R^{7'}$ and $R^{8'}$, $R^{2'}$, $R^{3'}$, $R^{4'}$ and $R^{5'}$ are each independently a hydrogen atom, a halogen atom, a group bonded via a carbon atom, a group bonded via a nitrogen atom, a group bonded via an oxygen atom or a group bonded via a sulfur atom, $R^{6'}$ is a halogen atom, a group bonded via a carbon atom, a group bonded via a nitrogen atom, a group bonded via an oxygen atom or a group bonded via a sulfur atom, $R^{7'}$ is an alkyl group optionally having substituent(s), and $R^{8'}$ is a hydrogen atom or an alkyl group optionally having substituent(s), provided that (i) 4-[(2S,3S)-2-benzyl-3-phenylpyrrolidin-1-yl]benzonitrile and (iii) 4-[(2S,3R)-2-(4-tert-butylbenzyl)-3-methylpyrrolidin-1-yl]benzonitrile are excluded;

[29] a compound represented by the formula (V)

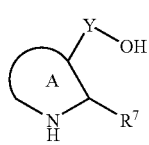

(V)

wherein ring A is a 5-membered ring to 8-membered ring, Y is a linker, and $R^7$ is a cyano group, a nitro group, an acyl group optionally having substituent(s), an optionally esterified or amidated carboxyl group or hydrocarbon group optionally having substituent(s) [hereinafter to be also referred to as compound (v)], or a salt thereof;

[30] the compound of the above-mentioned [29], which is represented by the formula (V)

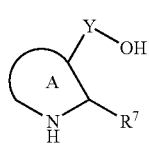

(V)

wherein ring A is a 5-membered or 6-membered ring optionally further having substituent(s) other than $R^7$ and —Y—OH, Y is a linker, and $R^7$ is an alkyl group optionally having substituent(s);

[31] the compound of the above-mentioned [29], which is represented by the formula (V')

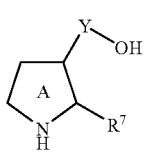

(V')

wherein ring A is a 5-membered ring optionally further having substituent(s) other than $R^7$ and —Y—OH, Y is a linker, and $R^7$ is an alkyl group optionally having substituent(s);

[32] the compound of the above-mentioned [29], which is represented by the formula (V")

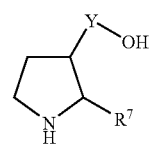

(V")

wherein Y is a linker, and $R^7$ is an alkyl group optionally having substituent(s);

[33] the compound of the above-mentioned [29], which is represented by the formula

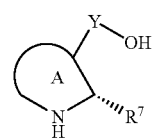

(VI)

wherein ring A is a 5-membered ring to 8-membered ring, Y is a linker, and $R^7$ is a cyano group, a nitro group, an acyl group optionally having substituent(s), an optionally esterified or amidated carboxyl group or hydrocarbon group optionally having substituent(s) [hereinafter to be also referred to as compound (VI)];

[34] the compound of the above-mentioned [30], which is represented by the formula

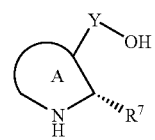

(VI)

wherein ring A is a 5- or 6-membered ring, Y is a linker, and $R^7$ is an alkyl group optionally having substituent(s);

[35] the compound of the above-mentioned [31], which is represented by the formula (VI')

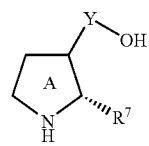

(VI')

wherein ring A is a 5-membered ring, Y is a linker, and $R^7$ is an alkyl group optionally having substituent(s);

[36] the compound of the above-mentioned [32], which is represented by the formula (VI")

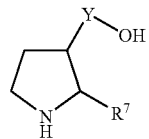

(VI")

wherein Y is a linker, and $R^7$ is an alkyl group optionally having substituent(s); and

[37] the compound of the above-mentioned [29] to [37], wherein the linker is a group represented by $CR^{11}R^{12}$ ($R^{11}$ and $R^{12}$ are each independently a hydrogen atom or an alkyl group optionally having substituent(s)), and the like.

[Explanation of Compound (IV)]

In compound (I), a compound wherein, when $R^1$ is a cyano group, $R^6$ is a group bonded via a carbon atom, a group bonded via a nitrogen atom, a group bonded via an oxygen atom or a group bonded via a sulfur atom, namely, compound (IV), is preferable.

As the "5- to 8-membered ring" for ring A', those similar to the "5- to 8-membered ring" for the above-mentioned ring A are used. Ring A' is preferably a 5- or 6-membered ring, more preferably a 5-membered ring.

In compound (IV), as the substituent that ring A' may further have other than $R^{6'}$, $R^{7'}$ and $R^{8'}$, a similar number of substituents similar to the substituents selected from the aforementioned substituent group A are used.

As the halogen atom, group bonded via a carbon atom, group bonded via nitrogen atom, group bonded via an oxygen atom or a bonded via a sulfur atom for $R^{2'}$, $R^{3'}$, $R^{4'}$ and $R^{5'}$, those similar to the halogen atom, group bonded via a carbon atom, group bonded via a nitrogen atom, group bonded via an oxygen atom or group bonded via a sulfur atom for $R^2$, $R^3$, $R^4$ and $R^5$ are used.

As the group bonded via a carbon atom, group bonded via a nitrogen atom, group bonded via an oxygen atom or group bonded via a sulfur atom for $R^{6'}$, those similar to the group bonded via a carbon atom, a group bonded via a nitrogen atom, a group bonded via an oxygen atom or a group bonded via a sulfur atom for $R^6$ are used.

As the "acyl group optionally having substituent(s)", "optionally esterified or amidated carboxyl group" or "hydrocarbon group optionally having substituent(s)" for $R^{7'}$, those similar to the "acyl group optionally having substituent(s)", "optionally esterified or amidated carboxyl group" or "hydrocarbon group optionally having substituent(s)" for $R^7$ are used.

As the "ring optionally having substituent(s)" formed by $R^{6'}$ and $R^{7'}$ together with the carbon atom bonded thereto, those similar to the "ring optionally having substituent(s)" for $R^6$ and $R^7$ are used.

As $R^{7'}$, an alkyl group optionally having substituent(s) is preferable.

As the "halogen atom", "group bonded via a carbon atom", "group bonded via a nitrogen atom", "group bonded via an oxygen atom" or "group bonded via a sulfur atom" for $R^{8'}$, those similar to the "halogen atom", "group bonded via a carbon atom", "group bonded via a nitrogen atom", "group bonded via an oxygen atom" or "group bonded via a sulfur atom" for $R^8$ are used. As $R^{8'}$, a hydrogen atom or an alkyl group optionally having substituent(s) is preferable.

[Production Method of Compound (I)]

Compound (I) of the present invention can be produced by a general organic synthesis method, or according to a known synthetic method (e.g., WO 2004-016576). For example, it can be synthesized by the following method.

Compound (I) can be produced, for example, by reacting a compound represented by the formula (VII)

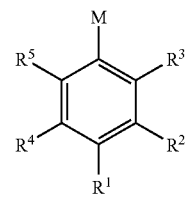

(VII)

wherein M is a leaving group, and other symbols are as defined above, or a salt thereof, with a compound represented by the formula (VIII)

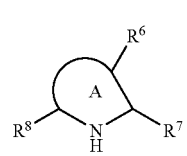

(VIII)

wherein each symbol is as defined above, or a salt thereof, and, when a protecting group is present, removing the protecting group.

As the "leaving group" for M, for example, a halogen such as fluorine, chlorine, bromine, iodine and the like, trifluoromethanesulfonyloxy, p-toluenesulfonyloxy, methanesulfonyloxy and the like can be used.

The compound (VIII) or a salt thereof is generally used in an amount of 1 to 3 mols per 1 mol of compound (VII). The reaction also proceeds smoothly by, where necessary, the addition of a base such as lithium carbonate, potassium carbonate, sodium carbonate, cesium carbonate, sodium hydrogencarbonate, sodium hydroxide, sodium t-butoxide, potassium tert-butoxide, triethylamine, diisopropylethylamine (DIEA), pyridine, 4-(dimethylamino)pyridine (DMAP), 1,8-diazabicyclo[5,4,0]undec-7-ene (DBU), 1,5-diazabicyclo[4,3,0]non-5-ene (DBN) and the like. Furthermore, the use of a transition metal catalyst (e.g., J.O.C., 1997, 62, pp 1264-1267) as a catalyst is also preferable.

The reaction can be performed in an inert solvent, for example, methanol, ethanol, propanol, isopropanol, n-butanol, tetrahydrofuran, diethyl ether, acetonitrile, acetone, ethyl acetate, 1,2-dimethoxyethane, 1,4-dioxane, toluene, benzene, xylene, dichloromethane, chloroform, 1,2-dichloroethane, N,N-dimethylformamide (DMF), dimethyl sulfoxide (DMSO) etc., or a mixed solvent thereof. The reaction can be performed in a temperature range of about 0° C. to 180° C. The reaction time is not particularly limited but it is generally 0.1 hr to 100 hr, preferably 0.5 hr to 72 hr.

Moreover, one or more substituents on ring A in compound (I) can be converted to other substituents. For example, it is possible to reduce a carbonyl group to alcohol, lead alcohol to olefin by dehydration, or alkylate alcohol to ether according to a method known per se.

The compounds (VII) and (VIII) used as starting substances can be synthesized by a known method or a method analogous thereto and, for example, can be produced by a method shown in the Reference Examples shown below.

Here, the group in the above-mentioned formulas may be protected by a protecting group generally used for organic synthesis. Where desired, the protecting group can be removed after the reaction by a known method.

Thus-obtained compound (I) can be isolated and purified by a separation means known per se, such as concentration, concentration under reduced pressure, solvent extraction, liquid conversion, salting out, crystallization, recrystallization, phase transfer, chromatography and the like.

When compound (I) is obtained as a free form, it can be converted to a desired salt by a method known per se or a modification thereof; conversely, when compound (I) is obtained as a salt, it can be converted to a free form or other desired salt by a method known per se or a modification thereof.

The compound (I') can be produced by the production method of the above-mentioned compound (I), the production method described in WO 2004/16576 and the like.

[Explanation of Compound (V) and Compound (VI)]

Of compounds (VIII), a compound represented by the formula (V)

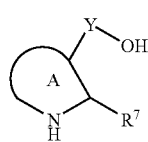

(V)

wherein each symbol is as defined above, or a salt thereof is a novel synthetic intermediate. Particularly, a compound represented by the formula (VI)

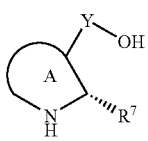

(VI)

wherein each symbol is as defined above, or a salt thereof is preferable.

As the "5- to 8-membered ring" for ring A in compound (VI), those similar to the "5- to 8-membered ring" for ring A in compound (I) are used. The ring A in compound (VI) is preferably a 5- or 6-membered ring, more preferably a 5-membered ring. In compound (VI), as the substituent that ring A may further have besides $R^7$ and —Y—OH, a similar number of substituents similar to the aforementioned substituent selected from substituent group A are used.

As the linker for Y, those similar to the linker for X are used. Particularly, a group represented by $CR^{11}R^{12}$ ($R^{11}$ and $R^{12}$ are each a hydrogen atom or an alkyl group optionally having substituent(s)) is preferable.

As the "alkyl group optionally having substituent(s)" for $R^{11}$ or $R^{12}$, those similar to the "alkyl group optionally having substituent(s)" for $R^9$ or $R^{10}$ are used. Particularly, a $C_{1-6}$ alkyl group (e.g., methyl, ethyl) and the like are preferable, and a methyl group is particularly preferable.

In compound (VI), as the "acyl group optionally having substituent(s)", "optionally esterified or amidated carboxyl group" or "hydrocarbon group optionally having substituent(s)" for $R^7$, those similar to "acyl group optionally having substituent(s)", "optionally esterified or amidated carboxyl group" or "hydrocarbon group optionally having substituent(s)" for $R^7$ in compound (I) are used.

As $R^7$, an alkyl group optionally having substituent(s) is preferable, a $C_{1-6}$ alkyl group (e.g., methyl, ethyl) and the like are more preferable, and a methyl group is particularly preferable.

The compounds (V) and (VI) can be synthesized by a known method or a method analogous thereto. For example, they can be produced by the methods shown in the Reference Examples to be mentioned below.

The compound (I) or compound (I') (hereinafter abbreviated as compound (I)) and the like may be a hydrate or a non-hydrate.

When compound (I) and the like are obtained as a mixture of optically active forms, they can be separated to the object (R) form and (S) form by an optical resolution means known per se.

Compound (I) and the like may be labeled with an isotope (e.g., $^3H$, $^{14}C$ etc.) and the like.

A prodrug of the compound (I) means a compound which is converted to the compound (I) with a reaction due to an enzyme, an gastric acid, etc. under the physiological condition in the living body, that is, a compound which is converted to the compound (I) with oxidation, reduction, hydrolysis, etc. according to an enzyme; a compound which is converted to the compound (I) by hydrolysis etc. due to gastric acid, etc.

A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation, dimethylaminomethylcarbonylation, etc.); a compound obtained by subjecting a carboxyl group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se.

A prodrug for compound (I) may also be one which is converted into compound (I) under a physiological condition, such as those described in IYAKUHIN no KAIHATSU (Development of Pharmaceuticals), Vol. 7, Design of Molecules, p. 163-198, 1990, Published by HIROKAWA SHOTEN.

The compound (including prodrug) of the present invention may form a salt. A salt of the compound is not particularly limited as long as it does not inhibit the reaction. For example, a salt with inorganic base, an ammonium salt, a salt with organic base, a salt with inorganic acid, a salt with organic acid, a salt with amino acid and the like can be mentioned. Preferable examples of salts with inorganic base include alkali metal salt such as sodium salt, potassium salt and the like, alkaline earth metal salt such as calcium salt, magnesium salt and the like, and aluminum salt, ammonium salt and the like. Preferable examples of salts with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of salts with inorganic acid include salts with hydrochloric acid, hydrobromic acid, nitric acid, sulfuric acid, phosphoric acid and the like. Preferable examples of salts with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of salts with basic amino acid include salts with arginine, lysine, ornithine and the like, and preferable examples of salts with acidic amino acid include salts with aspartic acid, glutamic acid and the like.

The compound of the present invention (I) or a prodrug thereof or a salt thereof (including the compound of the present invention (I') or a prodrug thereof or a salt thereof, hereinafter the same) (hereinafter sometimes to be abbreviated as the compound of the present invention) has an androgen receptor regulating action, particularly an androgen receptor agonist action, and can be used for the prophylaxis or treatment of a disease in a mammal, for which administration of an androgen receptor agonist is effective. The disease for which administration of an androgen receptor agonist is effective includes hypogonadism, osteoporosis, hormone resistant cancer (particularly LHRH agonist resistant cancer), climacteric disorder (particularly male climacteric disorder), frailty, cachexia, anemia, arteriosclerosis, Alzheimer's disease, erectile dysfunction, depression, wasting disease and the like.

The compound of the present invention has an organ specific androgen receptor regulating action and, for example, an antagonistic action on the prostate and an agonist action on the muscle, and shows effect as a frailty suppresser, a muscle strength enhancer or a muscle increasing agent while using as an agent for the prophylaxis or treatment of prostatomegaly or an agent for reducing the weight of the prostate. Accordingly, it is expected to shorten the period of rehabilitation without leaving aged inpatients bedridden. Without the side effect of increasing the weight of the prostate, it is expected to provide an agent for the treatment or prophylaxis of prostate cancer in patients with high possibility of prostate cancer. Without the side effect of virilization, moreover, it can be applied to female, and is expected to provide a suppressant of loss of muscle strength or bone mineral density loss in postmenopausal female, or a suppressant of hot flash (hot flash, sweating etc.) in postmenopausal female. Furthermore, it also is expected as an agent for reducing the side effects of LHRH agonists (leuprorelin, goserelin, buserelin, nafarelin, triptorelin, gonadorelin and the like), and LHRH antagonists (ganirelix, cetrorelix, antarelix, abarelix, and the like), a suppressant of loss of muscle strength or bone mineral density loss after administration of these pharmaceutical agents, or a suppressant of hot flash (hot flash, sweating and the like) after administration of these pharmaceutical agents.

The compound of the present invention achieves growth inhibition and cell death by conversely placing an excessive stimulation on cancer that has acquired resistance to a hormone treatment by being hypersensitive to androgen. Thus, it can be used as an agent for the prophylaxis or treatment of, from various cancers, breast cancer, prostate cancer, endometrial cancer, cancer of the uterine cervix, ovarian cancer, urinary bladder cancer, thyroid cancer, bone tumor and penile cancer, that acquired hormone resistance, and is particularly useful as an agent for the prophylaxis or treatment of prostate cancer.

As hormone resistant cancer, for example, LHRH derivative resistant cancer, preferably LHRH agonist resistant cancer can be mentioned.

The compound of the present invention has an androgen receptor agonist action and can be used for the prophylaxis or treatment of a disease in mammal, for which administration of an androgen receptor agonist is effective. The disease for which administration of an androgen receptor agonist is effective includes hypogonadism, osteoporosis, hormone resistant cancer (particularly LHRH agonist resistant cancer), climacteric disorder (particularly male climacteric disorder), frailty, cachexia, anemia, arteriosclerosis, Alzheimer's disease, erectile dysfunction, depression or wasting disease and the like.

The compound of the present invention shows low toxicity and can be used as a pharmaceutical agent as it is, or as a pharmaceutical composition in admixture with a commonly known pharmaceutically acceptable carrier etc. in mammals (e.g., humans, horses, bovines, dogs, cats, rats, mice, rabbits, pigs, monkeys, and the like).

In addition to the compound of the present invention, said pharmaceutical composition may contain other active ingredients, e.g., the following hormonal therapeutic agents, anticancer agent (e.g., chemotherapeutic agents, immunotherapeutic agents, or pharmaceutical agents inhibiting the action of cell growth factors or cell growth factor receptors), and the like.

As a pharmaceutical agent for mammals such as humans, the compound of the present invention can be administered orally in the form of, for example, tablets, capsules (including soft capsules and microcapsules), powders, granules and the like, or parenterally in the form of injections, suppositories, pellets and the like. Examples of the "parenteral administration route" include intravenous, intramuscular, subcutaneous, intra-tissue, intranasal, intradermal, instillation, intracerebral, intrarectal, intravaginal, intraperitoneal, intratumoral, juxtaposition of tumor and administration directly to the lesion.

The dose of the compound of the present invention varies depending on the route of administration, symptoms, etc. For example, when it is administered orally as an anticancer agent to a patient (body weight 40 to 80 kg) with breast cancer or prostate cancer, its dose is, for example, 0.1 to 200 mg/kg body weight per day, preferably 1 to 100 mg/kg body weight per day, and more preferably 1 to 50 mg/kg body weight per day. This amount may be administered once or in 2 to 3 divided portions daily.

The compound of the present invention can be orally or parenterally administered in the form of a solid dosage form such as tablet, capsule, granule, powder and the like; or a liquid preparation such as syrup, injection and the like, by admixing with a pharmaceutically acceptable carrier.

As a pharmaceutically acceptable carrier, various organic or inorganic carrier substances conventionally used as preparation materials can be used. For example, excipient, lubricant, binder and disintegrant for solid preparations, solvent, dissolution aids, suspending agent, isotonicity agent, buffer and soothing agent for liquid preparations and the like can be mentioned. Where necessary, conventional preparation additives such as preservatives, antioxidants, coloring agents, sweetening agents and the like can be used.

Preferable examples of the excipient include lactose, sucrose, D-mannitol, starch, crystalline cellulose, light anhydrous silicic acid and the like.

Preferable examples of the lubricant include magnesium stearate, calcium stearate, talc, colloidal silica and the like.

Preferable examples of the binder include crystalline cellulose, sucrose, D-mannitol, dextrin, hydroxypropylcellulose, hydroxypropylmethylcellulose, polyvinylpyrrolidone and the like.

Preferable examples of the disintegrant include starch, carboxymethylcellulose, calcium carboxymethylcellulose, croscarmellose sodium, carboxymethyl starch sodium and the like.

Preferable examples of the solvent include water for injection, alcohol, propylene glycol, macrogol, sesame oil, corn oil and the like.

Preferable examples of the dissolution aids include polyethylene glycol, propylene glycol, D-mannitol, benzyl benzoate, ethanol, trisaminomethane, cholesterol, triethanolamine, sodium carbonate, sodium citrate and the like.

Preferable examples of the suspending agent include surfactants such as stearyltriethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; and the like.

Preferable examples of the isotonicity agent include sodium chloride, glycerol, D-mannitol and the like.

Preferable examples of the buffer include buffers such as phosphate, acetate, carbonate, citrate and the like; and the like.

Preferable examples of the soothing agent include benzyl alcohol and the like.

Preferable examples of the preservative include paraoxybenzoates, chlorobutanol, benzyl alcohol, phenethyl alcohol, dehydroacetic acid, sorbic acid and the like.

Preferable examples of the antioxidant include sulfite, ascorbic acid and the like.

A pharmaceutical composition can be produced according to a conventional method by adding the compound of the present invention generally in a proportion of 0.1 to 95% (w/w) relative to the total amount of the preparation, though subject to change depending on the dosage form, administration method, carrier and the like.

In addition, a combination of (1) administering an effective amount of a compound of the present invention and (2) 1 to 3 selected from the group consisting of (i) administering an effective amount of other anticancer agents, (ii) administering an effective amount of hormonal therapeutic agents and (iii) non-drug therapy can prevent and/or treat cancer more effectively. As the non-drug therapy, for example, surgery, radiotherapy, gene therapy, thermotherapy, cryotherapy, laser cauterization, and the like are exemplified and two or more of these may be combined.

For example, the compound of the present invention can be used in combination with other hormonal therapeutic agents, anticancer agents (e.g., chemotherapeutic agents, immunotherapeutic agents, or pharmaceutical agents inhibiting the action of cell growth factors or cell growth factor receptors), antiemetic and the like (these are hereinafter abbreviated as a concomitant drug).

While the compound of the present invention exhibits excellent anticancer action even when used as a simple agent, its effect can be still more enhanced or QOL of patients can be improved by using it in combination with one or more of the concomitant drug(s) mentioned above (multi-agent co-administration).

As the "hormonal therapeutic agent", for example, fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, antiestrogens (e.g., tamoxifen citrate, toremifene citrate etc.), pill preparation, mepitiostane, testrolactone, aminoglutethimide, droloxifene, epitiostanol, ethinylestradiol sulfonate, aromatase inhibitors (e.g., fadrozole hydrochloride, anastrozole, retrozole, exemestane, vorozole, formestane etc.), anti-androgens (e.g., flutamide, bicartamide, nilutamide etc.), 5α-reductase inhibitors (e.g., finasteride, epristeride etc.), corticosteroids (e.g., dexamethasone, prednisolone, betamethasone, triamcinolone etc.), androgen synthesis inhibitors (e.g., abiraterone etc.), retinoid and drugs that retard retinoid metabolism (e.g., liarozole etc.), LH-RH derivative and the like are used. Preferred is an LH-RH derivative.

Examples of the "chemotherapeutic agents" include alkylating agents, antimetabolites, anticancer antibiotics, plant-derived anticancer agents, and the like.

Examples of the "alkylating agent" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, carboquone, adozelesin, cystemustine, bizelesin, and the like.

Examples of the "antimetabolites" include mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emitefur etc.), aminopterine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine and the like.

Examples of the "antitumor antibiotics" include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride and the like.

Examples of the "plant-derived antitumor agent" include etoposide, etoposide phosphate, vinblastine sulfate, vincristine sulfate, vindesine sulfate, teniposide, paclitaxel, docetaxel, DJ-927, vinorelbine and the like.

Examples of the "immunotherapeutic agent (BRM)" include picibanil, krestin, schizophyllan, lentinan, ubenimex, interferon, interleukin, macrophage colony stimulating agent, granulocyte colony stimulating factor, erythropoietin, lymphotoxin, BCG vaccine, *Corynebacterium parvum*, levamisole, polysaccharide K, procodazole and the like.

The "growth factor" in said "pharmaceutical agents inhibiting the action of cell growth factors or cell growth factor receptors" may be any as long as it promotes cell proliferation, which is normally peptide having a molecular weight of not more than 20,000 that is capable of exhibiting its activity at low concentrations by binding to a receptor. Examples thereof include (1) EGF (epidermal growth factor) or substances possessing substantially the same activity as it [e.g., EGF, heregulin (HER2 ligand), and the like], (2) insulin or substances possessing substantially the same activity as it [e.g., insulin, IGF (insulin-like growth factor)-1, IGF-2, and the like], (3) FGF (fibroblast growth factor) or substances possessing substantially the same activity as it [e.g., acidic FGF, basic FGF, KGF (keratinocyte growth factor), FGF-10, and the like], (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial cell growth factor), and the like], and the like.

Examples of the "growth factor receptors" include any receptors capable of binding to the aforementioned cell growth factors, including EGF receptor, heregulin receptor (HER2), insulin receptor, IGF receptor, FGF receptor-1 or FGF receptor-2, and the like.

Examples of the "pharmaceutical agents inhibiting the action of cell growth factor" include trastuzumab (Herceptin (trade mark): HER2 antibody), imatinib mesilate, ZD1839 or cetuximab, and the like.

In addition to the aforementioned drugs, L-asparaginase, aceglatone, procarbazine hydrochloride, protoporphyrin-cobalt complex salt, mercuric hematoporphyrin-sodium, topoisomerase I inhibitors (e.g., irinotecan, nogitecan, exatecan (DX-8951f. DE-310), rubitecan, T-0128 etc.), topoisomerase II inhibitors (e.g., sobuzoxane, and the like), differentiation inducers (e.g., retinoid, vitamin D, and the like), angiogenesis inhibitors, α-blockers (e.g., tamsulosin hydrochloride and the like), TZT-1027, and the like can also be used.

As the "antiemetic", gastric motility enhancers such as 5-$HT_3$ antagonist such as ondansetron, tropisetron hydrochloride, azasetron, ramosetron, granisetron, dolasetron mesylate, palonosetron and the like, 5-$HT_4$ antagonists such as domperidone, mosapride, metoclopramide and the like, and the like; gastrointestinal tract motility regulators such as trimebutine and the like; phenothiazine pharmaceutical agents such as prochlorperazine maleate, promethazine, thiethylperazine and the like; tranquilizers such as haloperidol, chlorpromazine phenolphthalinate, diazepam, droperidol and the like; steroids such as dexamethasone, prednisolone, betamethasone, triamcinolone and the like; as well as dimethylhydrin acid, diphenhydramine, hyoscine, hyoscine hydrobromide, tetrabenazine and the like can be used.

As the aforementioned LH-RH derivative, an LH-RH derivative or a salt thereof effective for hormone dependent disease, particularly sex hormone dependent disease such as sex hormone dependent cancer (e.g., prostate cancer, uterine cancer, breast cancer, pituitary gland tumor, liver cancer and the like), prostatomegaly, endometriosis, hysteromyoma, precocity, dysmenorrhea, amenorrhea, premenstrual syndrome, polycystic ovary syndrome and the like and contraception (or infertility when rebound effect after cessation of the drug is used) are used. In addition, an LH-RH derivative or a salt thereof effective for benignant or malignant tumor, which is sex hormone independent but LH-RH sensitive, and the like is also used.

Specific examples of the LH-RH derivative or a salt thereof include peptides described in Treatment with GnRH analogs: Controversies and perspectives (The Parthenon Publishing Group Ltd., published in 1996), JP-A-3-503165, JP-A-3-101695, JP-A-7-97334, JP-A-8-259460 and the like.

Examples of the LH-RH derivative include an LH-RH agonist and an LH-RH antagonist. As the LH-RH antagonist, for example, physiologically active peptide represented by the formula X-D2Nal-D4ClPhe-D3Pal-Ser-A-B-Leu-C-Pro-DAlaNH$_2$ wherein X is N(4H$_2$-furoyl)Gly or NAc, A is a residue selected from NMeTyr, Tyr, Aph(Atz) and NMeAph(Atz), B is a residue selected from DLys(Nic), DCit, DLys(Azag-lyNic), DLys(AzaglyFur), DhArg(Et$_2$), DAph(Atz) and DhCi, and C is Lys(Nisp), Arg or hArg(Et$_2$), or a salt thereof and the like are used, particularly preferably abarelix, ganirelix, cetrorelix, 5-(N-benzyl-N-methylaminomethyl)-1-(2,6-difluorobenzyl)-6-[4-(3-methoxyureido)phenyl]-3-phenylthieno[2,3-d]pyrimidine-2,4(1H,3H)-dione, 5-(N-benzyl-N-methylaminomethyl)-1-(2,6-difluorobenzyl)-6-[4-(3-ethylureido)phenyl]-3-phenylthieno[2,3-d]pyrimidine-2,4(1H,3H)-dione, 5-(N-benzyl-N-methylaminomethyl)-1-(2,6-difluorobenzyl)-6-[4-(3-ethylureido)phenyl]-3-phenylthieno[2,3-d]pyrimidine-2,4(1H,3H)-dione hydrochloride and the like are used.

As the LH-RH agonist, for example, physiologically active peptides represented by the formula 5-oxo-Pro-His-Trp-Ser-Tyr-Y-Leu-Arg-Pro-Z wherein Y is a residue selected from DLeu, DAla, DTrp, DSer(tBu), D2Nal and DHis(ImBzl), and Z is NH—C$_2$H$_5$ or Gly-NH$_2$, or a salt thereof and the like are used. For example, they are goserelin acetate, buserelin and the like. Particularly, peptide wherein Y is DLeu and Z is NH—C$_2$H$_5$ (i.e., peptide A represented by 5-oxo-Pro-His-Trp-Ser-Tyr-DLeu-Leu-Arg-Pro-NH—C$_2$H$_5$; leuprorelin) or a salt thereof (e.g., acetate) is preferable.

When the amino acid, peptide, protecting group and the like of the polypeptide described in the present specification are indicated using abbreviations, they are based on the abbreviations according to the IUPAC-IUB Commission on Biochemical Nomenclature or conventional abbreviations in the field. When an optical isomer due to amino acid is present, it means an L form unless otherwise specified.

Examples of the abbreviations are as follows.

Abu: aminobutyric acid
Aibu: 2-aminobutyric acid
Ala: alanine
Arg: arginine
Gly: glycine
His: histidine
Ile: isoleucine
Leu: leucine
Met: methionine
Nle: norleucine
Nval: norvaline
Phe: phenylalanine
Phg: phenylglycine
Pro: proline
(Pyr)Glu: pyroglutamic acid
Ser: serine
Thr: threonine
Trp: tryptophan
Tyr: tyrosine
Val: valine
D2Nal: D-3-(2-naphthyl)alanine residue
DSer(tBu): O-tert-butyl-D-serine
DHis(ImBzl): N$^{im}$-benzyl-D-histidine
PAM: phenylacetamidomethyl
Boc: t-butyloxycarbonyl
Fmoc: 9-fluorenylmethyloxycarbonyl
Cl—Z: 2-chloro-benzyloxycarbonyl
Br—Z: 2-bromo-benzyloxycarbonyl
Bzl: benzyl
Cl$_2$-Bzl: 2,6-dichlorobenzyl
Tos: p-toluenesulfonyl
HONb: N-hydroxy-5-norbornane-2,3-dicarboxylmide
HOBt: 1-hydroxybenzotriazole
HOOBt: 3-hydroxy-3,4-dihydro-4-oxo-1,2,3-benzotriazine
MeBzl: 4-methylbenzyl Bom: benzyloxymethyl
Bum: t-butoxy methyl
Trt: trityl
DNP: dinitrophenyl
DCC: N,N'-dicyclohexylcarbodiimide Of the aforementioned drugs, preferable concomitant drugs are an LH-RH agonist (e.g., goserelin acetate, buserelin, leuprorelin etc.) and the like.

When using the compound of the present invention and a concomitant drug in combination, the administration time of the compound of the present invention and the concomitant drug is not restricted, and the compound of the present invention or the concomitant drug can be administered to an administration subject simultaneously, or may be administered at different times. The dosage of the concomitant drug may be determined according to the administration amount clinically used, and can be appropriately selected depending on an administration subject, administration route, disease, combination and the like.

The administration mode of the compound of the present invention and the concomitant drug is not particularly limited, and the compound of the present invention and the concomitant drug only need to be combined on administration. Examples of such administration mode include the following: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (for example, administration in the order of the compound of the present invention and the concomitant drug, or in the reverse order) and the like. In the following, these administration modes are collectively abbreviated as the concomitant drug of the present invention.

The concomitant drug of the present invention has low toxicity, and for example, the compound of the present invention and/or the above-mentioned concomitant drug can be mixed, according to a method known per se, with a pharmacologically acceptable carrier to give pharmaceutical compositions, such as tablets (including sugar-coated tablet, film-coated tablet), powders, granules, capsules (including soft capsule), solutions, injections, suppositories, sustained release agents and the like, which can be safely administered orally or parenterally (e.g., local, rectum, vein, and the like). An injection can be administered intravenously, intramuscularly, subcutaneously, into the organ, intranasally, intradermally, by instillation, intracerebrally, intrarectally, vaginally and intraperitoneally, intratumorally, proximally to the tumor and the like, or directly to the lesion.

As a pharmacologically acceptable carrier which may be used for producing the concomitant drug of the present invention, those similar to the aforementioned pharmacologically acceptable carriers that can be used for the pharmaceutical composition of the present invention can be used.

The compounding ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to 100% by weight, preferably from about 0.1 to 50% by weight, further preferably from about 0.5 to 20% by weight, based on the entire preparation.

The content of the concomitant drug in the combination agent of the present invention differs depending on the form of a preparation, and usually from about 0.01 to 100% by weight, preferably from about 0.1 to 50% by weight, further preferably from about 0.5 to 20% by weight, based on the entire preparation.

The content of additives such as carrier and the like in the combination agent of the present invention differs depending on the form of a preparation, and usually from about 1 to 99.99% by weight, preferably from about 10 to 90% by weight, based on the entire preparation.

In the case when the compound of the present invention and the concomitant drug are separately prepared respectively, the same contents may be adopted.

These preparations can be produced by a method known per se usually used in a preparation process.

For example, the compound of the present invention and the concomitant drug can be made into an aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin and the like), a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, mannitol, sorbitol, glucose and the like), a pH regulator (e.g., hydrochloric acid, sodium hydroxide and the like), a preservative (e.g., ethyl p-oxybenzoate, benzoic acid, methylparaben, propylparaben, benzyl alcohol and the like), a dissolving agent (e.g., conc. glycerin, meglumine and the like), a dissolution aid (e.g., propylene glycol, sucrose and the like), a soothing agent (e.g., glucose, benzyl alcohol and the like), and the like, or can be dissolved, suspended or emulsified in a vegetable oil such as olive oil, sesame oil, cotton seed oil, corn oil and the like or a dissolution aid such as propylene glycol and prepared into an oily injection, whereby an injection is afforded.

To produce a preparation for oral administration, an excipient (e.g., lactose, sucrose, starch and the like), a disintegrating agent (e.g., starch, calcium carbonate and the like), a binder (e.g., starch, gum Arabic, carboxymethylcellulose, polyvinylpyrrolidone, hydroxypropylcellulose and the like), a lubricant (e.g., talc, magnesium stearate, polyethylene glycol 6000 and the like) and the like, for example, can be added to the compound of the present invention or the concomitant drug, according to a method known per se, and the mixture can be compression-molded, then if desirable, the molder product can be coated by a method known per se for the purpose of masking of taste, enteric property or durability, to obtain a preparation for oral administration. As the coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudoragit (methacrylic acid.acrylic acid copolymer, manufactured by Rohm, DE), pigment (e.g., iron oxide red, titanium dioxide, etc.) and the like can be used. The preparation for oral administration may be any of a immediate-release preparation and a sustained release preparation.

For example, to give a suppository, the compound of the present invention and the concomitant drug can be made into an oily or aqueous solid, semisolid or liquid suppository according to a method known per se. As the oily substrate to be used for the aforementioned composition, for example, glycerides of higher fatty acids [e.g., cacao butter, Witepsols (manufactured by Dynamit Nobel, Germany), etc.], medium chain fatty acid [e.g., Miglyols (manufactured by Dynamit Nobel, Germany), etc.], or vegetable oils (e.g., sesame oil, soybean oil, cotton seed oil and the like), and the like are listed. Further, as the aqueous substrate, for example, polyethylene glycols, propylene glycol are listed, and as the aqueous gel substrate, for example, natural gums, cellulose derivatives, vinyl polymers, acrylic acid polymers and the like are listed.

As the above-mentioned sustained release preparation, sustained release microcapsules and the like are used.

The sustained release microcapsule can be produced by a method known per se and, for example, a sustained-release preparation such as the one shown in the following [2] is preferably formed and administered.

The compound of the present invention is preferably molded into an oral administration preparation such as a solid preparation (e.g., powder, granule, tablet, capsule) and the like, or molded into a rectal administration preparation such as a suppository. Particularly, an oral administration preparation is preferable.

The concomitant drug can be made into the above-mentioned drug form depending on the kind of the drug.

[1] An injection of the compound of the present invention or the concomitant drug, and preparation thereof, [2] a sustained release preparation or immediate-release preparation of the compound of the present invention or the concomitant drug, and preparation thereof, [3] a sublingual, buccal or intraoral quick integrating agent of the compound of the present invention or the concomitant drug, and preparation thereof, will be specifically described in the following.

[1] Injection and Preparation Thereof

An injection prepared by dissolving the compound of the present invention or the concomitant drug into water is preferable. This injection may be allowed to contain a benzoate and/or salicylate.

The injection is obtained by dissolving the compound of the present invention or the concomitant drug, and if desirable, a benzoate and/or salicylate, into water.

As the above-mentioned salts of benzoic acid and salicylic acid, for example, salts of alkali metals such as sodium, potassium and the like, salts of alkaline earth metals such as calcium, magnesium and the like, ammonium salts, meglumine salts, salts with organic acid salts such as tromethamol and the like, etc. are used.

The concentration of the compound of the present invention or the concomitant drug in an injection is from 0.5 to 50 w/v %, preferably from about 3 to 20 w/v %. The concentration of a benzoate or/and salicylate is from 0.5 to 50 w/v %, preferably from about 3 to 20 w/v %.

Into this injection, additives usually used in an injection, for example, a stabilizer (e.g., ascorbic acid, sodium pyrosulfite and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride and the like), a dispersing agent (e.g., hydroxypropylmethylcellulose, dextrin), a pH regulator (e.g., hydrochloric acid, sodium hydroxide and the like), a preservative (e.g., ethyl p-oxybenzoate, benzoic acid and the like), a dissolving agent (e.g., conc. glycerin, meglumine and the like), a dissolution aid (e.g., propylene glycol, sucrose and the like), a soothing agent (e.g., glucose, benzyl alcohol and the like), and the like, can be appropriately blended. These additives are generally blended in a proportion usually used in an injection.

It is advantageous that pH of an injection is controlled from pH 2 to 12, preferably from pH 2.5 to 8.0 by addition of a pH regulator.

An injection is obtained by dissolving the compound of the present invention or the concomitant drug and if desirable, a benzoate and/or a salicylate, and if necessary, the above-mentioned additives into water. These may be dissolved in any order, and can be appropriately dissolved in the same manner as in a conventional method of producing an injection.

An aqueous solution for injection is advantageously heated, alternatively, for example, filter sterilization, high pressure heat sterilization and the like can be conducted in the same manner as for a usual injection, to provide an injection.

It is advantageous that an aqueous solution for injection be subjected to high pressure heat sterilization at 100 to 121° C. for 5 to 30 min.

Further, a preparation endowed with an antibacterial property of a solution may also be produced so that it can be used as a preparation which is divided and administered multiple-times.

[2] Sustained Release Preparation or Immediate-Release Preparation, and Preparation Thereof A sustained release preparation is preferable, which is obtained, if desirable, by coating a nucleus containing the compound of the present invention or the concomitant drug with a film agent such as a water-insoluble substance, swellable polymer and the like. For example, a sustained release preparation for oral administration of once administration per day type is preferable.

As the water-insoluble substance used in a film agent, there are listed, for example, cellulose ethers such as ethylcellulose, butylcellulose and the like, cellulose esters such as cellulose acetate, cellulose propionate and the like, polyvinyl esters such as polyvinyl acetate, polyvinyl butyrate and the like, acrylic acid/methacrylic acid copolymers, methyl methacrylate copolymers, ethoxyethyl methacrylate/cinnamoethyl methacrylate/aminoalkyl methacrylate copolymers, polyacrylic acid, polymethacrylic acid, methacrylic acid alkylamide copolymers, poly(methyl methacrylate), polymethacrylates, polymethacrylamides, aminoalkyl methacrylate copolymers, poly(methacrylic anhydride), glycidyl methacrylate copolymers, particularly, acrylic acid-based polymers such as Eudoragit (Rohm Pharma) such as Eudoragit RS-100, RL-100, RS-30D, RL-30D, RL-PO, RS-PO (ethyl acrylate/methyl methacrylate/trimethylammoniumethyl methacrylate chloride copolymer), Eudoragit NE-30D (methyl methacrylate/ethyl acrylate copolymer), and the like, hydrogenated oils such as hydrogenated castor oil (e.g., Lubri wax (Freund Corporation) and the like) and the like, waxes such as carnauba wax, glycerin fatty acid ester, paraffin and the like, polyglycerin fatty esters, and the like.

As the swellable polymer, polymers having an acidic dissociating group and showing pH dependent swell are preferable, and polymers having an acidic dissociating group, which manifest small swelling in acidic regions such as in stomach and large swelling in neutral regions such as in small intestine and large intestine, are preferable.

As such a polymer having an acidic dissociating group and showing pH dependent swell, cross-linkable polyacrylic acid polymers such as, for example, Carbomer 934P, 940, 941, 974P, 980, 1342 and the like, polycarbophil, calcium polycarbophil (last two are manufactured by BF Goodrich), Hiviswako 103, 104, 105, 304 (all are manufactured by Wako Pure Chemical Industries, Ltd.), and the like, are listed.

The film agent used in a sustained release preparation may further contain a hydrophilic substance.

As the hydrophilic substance, for example, polysaccharides which may contain a sulfate group such as pullulan, dextrin, alkali metal alginate and the like, polysaccharides having a hydroxyalkyl group or carboxyalkyl group such as hydroxypropylcellulose, hydroxypropylmethylcellulose, carboxymethylcellulose sodium and the like, methylcellulose, polyvinylpyrrolidone, polyvinyl alcohol, polyethylene glycol and the like can be mentioned.

The content of a water-insoluble substance in the film agent of a sustained release preparation is from about 30 to about 90% (w/w), preferably from about 35 to about 80% (w/w), further preferably from about 40 to about 75% (w/w), the content of a swellable polymer is from about 3 to about 30% (w/w), preferably from about 3 to about 15% (w/w). The film agent may further contain a hydrophilic substance, and in which case, the content of a hydrophilic substance in the film agent is about 50% (w/w) or less, preferably about 5 to 40% (w/w), further preferably from about 5 to 35% (w/w). This % (w/w) indicates % by weight based on a film agent composition which is obtained by removing a solvent (e.g., water, lower alcohols such as methanol, ethanol and the like) from a film agent solution.

The sustained release preparation is produced by preparing a nucleus containing a drugs as exemplified below, then, coating the resulted nucleus with a film agent solution prepared by heat-solving a water-insoluble substance, swellable polymer and the like or by dissolving or dispersing it in a solvent.

I. Preparation of Nucleus Containing Drug

The form of nucleus containing a drug to be coated with a film agent (hereinafter, sometimes simply referred to as nucleus) is not particularly restricted, and preferably, the nucleus is formed into particles such as a granule or fine particle.

When the nucleus is composed of granules or fine particles, the average particle size thereof is preferably from about 150 to about 2000 μm, further preferably, from about 500 to about 1400 μm.

Preparation of the nucleus can be effected by a usual production method. For example, a suitable excipient, binding agent, disintegrating agent, lubricant, stabilizer and the like are mixed with a drug, and the mixture is subjected to a wet extrusion granulating method, fluidized bed granulating method or the like, to prepare a nucleus.

The content of drugs in a nucleus is from about 0.5 to about 95% (w/w), preferably from about 5.0 to about 80% (w/w), further preferably from about 30 to about 70% (w/w).

As the excipient contained in the nucleus, for example, saccharides such as sucrose, lactose, mannitol, glucose and the like, starch, crystalline cellulose, calcium phosphate, corn starch and the like are used. Among them, crystalline cellulose, corn starch are preferable.

As the binding agent, for example, polyvinyl alcohol, hydroxypropylcellulose, polyethylene glycol, polyvinyl pyrrolidone, Pluronic F68, gum Arabic, gelatin, starch and the like are used. As the disintegrating agent, for example, carboxymethylcellulose calcium (ECG505), croscarmelose sodium (Ac-Di-Sol), crosslinked polyvinylpyrrolidone (Crospovidone), low substituted hydroxypropylcellulose (L-HPC) and the like are used. Among them, hydroxypropylcellulose, polyvinylpyrrolidone, lower substituted hydroxypropylcellulose are preferable. As the lubricant and coagulation inhibitor, for example, talc, magnesium stearate and inorganic salts thereof are used, and as the lubricant, polyethylene glycol and the like are used. As the stabilizer, acids such as tartaric acid, citric acid, succinic acid, fumaric acid, maleic acid and the like, are used.

A nucleus can also be prepared by, in addition to the above-mentioned, for example, a rolling granulation method in which a drug or a mixture of a drug with an excipient, lubricant and the like are added portionwise onto an inert carrier particle which is the core of the nucleus while spraying a binder dissolved in a suitable solvent such as water, lower alcohol (e.g., methanol, ethanol and the like) and the like, a pan coating method, a fluidized bed coating method or a melt granulating method. As the inert carrier particle, for example, those made of sucrose, lactose, starch, crystalline cellulose or waxes can be used, and the average particle size thereof is preferably from about 100 μm to about 1500 μm.

For separating a drug contained in a nucleus and a film agent, the surface of the nucleus may be coated with a protective agent. As the protective agent, for example, the above-mentioned hydrophilic substances, water-insoluble substances and the like are used. As the protective agent, preferably polyethylene glycol, and polysaccharides having a hydroxyalkyl group or carboxyalkyl group are used, more preferably, hydroxypropylmethylcellulose and hydroxypropylcellulose are used. The protective agent may contain, as stabilizer, acids such as tartaric acid, citric acid, succinic acid, fumaric acid, maleic acid and the like, and lubricants such as talc and the like. When the protective agent is used, the coating amount is from about 1 to about 15% (w/w), preferably from about 1 to about 10% (w/w), further preferably from about 2 to about 8% (w/w), based on the nucleus.

The protective agent can be coated by a usual coating method, and specifically, the protective agent can be coated by spray-coating the nucleus, for example, by a fluidized bed coating method, pan coating method and the like.

II. Coating of Nucleus with Film Agent

A nucleus obtained in the above-mentioned step I is coated with a film agent solution obtained by heat-solving the above-mentioned water-insoluble substance and pH-dependent swellable polymer, and a hydrophilic substance, or by dissolving or dispersing them in a solvent, to give a sustained release preparation.

As the method for coating a nucleus with a film agent solution, for example, a spray coating method and the like are listed.

The composition ratio of a water-insoluble substance, swellable polymer or hydrophilic substance in a film agent solution is appropriately selected so that the contents of these components in a coated film are the above-mentioned contents, respectively.

The coating amount of a film agent is from about 1 to about 90% (w/w), preferably from about 5 to about 50% (w/w), further preferably from about 5 to about 35% (w/w), based on a nucleus (not including coating amount of protective agent).

As the solvent in a film agent solution, water or an organic solvent can be used alone or in admixture thereof. In the case of use in admixture, the mixing ratio of water to an organic solvent (water/organic solvent: by weight) can be varied in the range from 1 to 100%, and is preferably from 1 to about 30%. The organic solvent is not particularly restricted providing it dissolves a water-insoluble substance, and for example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Among them, lower alcohols are preferable, and ethyl alcohol and isopropyl alcohol are particularly preferable. Water, and a mixture of water with an organic solvent are preferably used as a solvent for a film agent. In this case, if necessary, an acid such as tartaric acid, citric acid, succinic acid, fumaric acid, maleic acid and the like may also be added into a film agent solution for stabilizing the film agent solution.

An operation of coating by spray coating can be effected by a usual coating method, and specifically, it can be performed by spray-coating a film agent solution onto a nucleus by a fluidized bed coating method, pan coating method and the like. In this case, if necessary, talc, titanium oxide, magnesium stearate, calcium stearate, light anhydrous silicic acid and the like may also be added as a lubricant, and glycerin fatty acid ester, hydrogenated castor oil, triethyl citrate, cetyl alcohol, stearyl alcohol and the like may also be added as a plasticizer.

After coating with a film agent, if necessary, an antistatic agent such as talc and the like may be mixed.

The immediate-release preparation may be liquid (solution, suspension, emulsion and the like) or solid (particle, pill, tablet and the like). Oral agents and parenteral agents such as an injection and the like are used, and oral agents are preferable.

The immediate-release preparation, usually, may contain, in addition to an active component drug, also carriers, additives and excipients conventionally used in the production field (hereinafter, sometimes abbreviated as excipient). The preparation excipient used is not particularly restricted providing it is an excipient ordinarily used as a preparation excipient. For example, as the excipient for an oral solid preparation, lactose, starch, corn starch, crystalline cellulose (Avicel PH101, manufactured by Asahi Kasei Corporation, and the like), powder sugar, granulated sugar, mannitol, light anhydrous silicic acid, magnesium carbonate, calcium carbonate, L-cysteine and the like are listed, and preferably, corn starch and mannitol and the like are listed. These excipients can be used alone or in combination of two or more. The content of the excipient is, for example, from about 4.5 to about 99.4 w/w %, preferably from about 20 to about 98.5 w/w %, further preferably from about 30 to about 97 w/w %, based on the total amount of the immediate-release preparation.

The content of a drug in the immediate-release preparation can be appropriately selected in the range from about 0.5 to about 95%, preferably from about 1 to about 60% based on the total amount of the immediate-release preparation.

When the immediate-release preparation is an oral solid preparation, it usually contains, in addition to the above-mentioned components, also an integrating agent. As this integrating agent, for example, carboxymethylcellulose calcium (ECG-505, manufactured by Gotoku Yakuhin), croscarmelose sodium (for example, Actisol, manufactured by Asahi Kasei Corporation), crospovidone (for example, Kollidon CL, manufactured by BASF), low substituted hydroxypropylcellulose (manufactured by Shin-Etsu Chemical Co., Ltd.), carboxymethylstarch (manufactured by Matsutani Kagaku K.K.), carboxymethylstarch sodium (Exprotab, manufactured by Kimura Sangyo), partially pregelatinized starch (PCS, manufactured by Asahi Kasei Corporation), and the like are used, and for example, those which disintegrate a granule by adsorbing water in contact with water, causing swelling, or making a channel between an effective ingredient constituting the nucleus and an excipient, can be used. These disintegrating agents can be used alone or in combination of two or more. The amount of the disintegrating agent used is appropriately selected depending on the kind and blending amount of a drug used, design of releasing property, and the like, and for example, from about 0.05 to about 30 w/w %, preferably from about 0.5 to about 15 w/w %, based on the total amount of the quick releasing agent.

When the immediate-release preparation is an oral solid preparation, it may further contain, in addition to the above-mentioned composition in the case of the oral solid preparation, if desired, additives conventional in solid preparations. As such an additive, there are used, for example, a binder (e.g., sucrose, gelatin, gum Arabic powder, methylcellulose, hydroxypropylcellulose, hydroxypropylmethylcellulose, carboxymethylcellulose, polyvinylpyrrolidone, pullulan, dextrin and the like), a lubricant (e.g., polyethylene glycol, magnesium stearate, talc, light anhydrous silicic acid (for example, Aerosil (Nippon Aerosil)), a surfactant (e.g., anionic surfactants such as sodium alkylsulfate and the like, nonionic surfactants such as polyoxyethylene fatty acid ester and polyoxyethylene sorbitan fatty acid ester, polyoxyethylene castor oil derivatives and the like), a coloring agent (e.g., tar coloring matter, caramel, iron oxide red, titanium oxide, riboflavins), if necessary, an appetizing agent (e.g., sweetening agent, flavoring agent and the like), an adsorbent, preservative, wetting agent, antistatic agent, and the like. Further, as the stabilizer, an organic acid such as tartaric acid, citric acid, succinic acid, fumaric acid and the like may also be added.

As the above-mentioned binder, hydroxypropylcellulose, polyethylene glycol and polyvinylpyrrolidone and the like are preferably used.

The immediate-release preparation can be prepared by, based on a usual technology of producing preparations, mixing the above-mentioned components, and if necessary, further kneading the mixture, and molding it. The above-mentioned mixing is conducted by generally used methods, for example, mixing, kneading and the like. Specifically, when a immediate-release preparation is formed, for example, into a particle, it can be prepared, according to the same means as in the above-mentioned method for preparing a nucleus of a sustained release preparation, by mixing the components using a vertical granulator, universal kneader (manufactured by Hata Tekkosho), fluidized bed granulator FD-5S (manufactured by Powrex Corporation), and the like, and then, granulating the mixture by a wet extrusion granulation method, fluidized bed granulation method and the like.

Thus obtained immediate-release preparation and sustained release preparation may be themselves made into products or made into products appropriately together with preparation excipients and the like, separately, by an ordinary method, then, may be administered simultaneously or may be administered in combination at any administration interval, or they may be themselves made into one oral preparation (e.g., granule, fine particle, tablet, capsule and the like) or made into one oral preparation appropriately together with preparation excipients and the like. It may also be permissible that they are made into granules or fine particles, and filled in the same capsule to be used as a preparation for oral administration.

[3] Sublingual, Buccal or Intraoral Quick Disintegrating Agent and Preparation Thereof Sublingual, buccal or intraoral quick disintegrating agents may be a solid preparation such as tablet and the like, or may be an oral mucosa membrane patch (film).

As the sublingual, buccal or intraoral quick disintegrating agent, a preparation containing the compound of the present invention or the concomitant drug and an excipient is preferable. It may contain also auxiliary agents such as a lubricant, isotonizing agent, hydrophilic carrier, water-dispersible polymer, stabilizer and the like. Further, for easy absorption and increased bioavailability, β-cyclodextrin or β-cyclodextrin derivatives (e.g., hydroxypropyl-β-cyclodextrin and the like) and the like may also be contained.

As the above-mentioned excipient, lactose, sucrose, D-mannitol, starch, crystalline cellulose, light anhydrous silicic acid and the like are listed. As the lubricant, magnesium stearate, calcium stearate, talc, colloidal silica and the like are listed, and particularly, magnesium stearate and colloidal silica are preferable. As the isotonizing agent, sodium chloride, glucose, fructose, mannitol, sorbitol, lactose, saccharose, glycerin, urea and the like are listed, and particularly, mannitol is preferable. As the hydrophilic carrier, swellable hydrophilic carriers such as crystalline cellulose, ethylcellulose, crosslinkable polyvinylpyrrolidone, light anhydrous silicic acid, silicic acid, dicalcium phosphate, calcium carbonate and the like are listed, and particularly, crystalline cellulose (e.g., microcrystalline cellulose and the like) is preferable. As the water-dispersible polymer, gums (e.g., gum tragacanth, acacia gum, guar gum), alginates (e.g., sodium alginate), cellulose derivatives (e.g., methylcellulose, carboxymethylcellulose, hydroxymethylcellulose, hydroxypropylcellulose, hydroxypropylmethylcellulose), gelatin, water-soluble starch, polyacrylic acids (e.g., Carbomer), polymethacylic acid, polyvinyl alcohol, polyethylene glycol, polyvinylpyrrolidone, polycarbophil, ascorbate palmitates and the like are listed, and hydroxypropylmethylcellulose, polyacrylic acid, alginate, gelatin, carboxymethylcellulose, polyvinylpyrrolidone, polyethylene glycol and the like are preferable. Particularly, hydroxypropylmethylcellulose is preferable. As the stabilizer, cysteine, thiosorbitol, tartaric acid, citric acid, sodium carbonate, ascorbic acid, glycine, sodium sulfite and the like are listed, and particularly, citric acid and ascorbic acid are preferable.

The sublingual, buccal or intraoral quick disintegrating agent can be produced by mixing the compound of the present invention or the concomitant drug and an excipient by a method known per se. Further, if desired, the above-mentioned auxiliary agents such as a lubricant, isotonizing agent, hydrophilic carrier, water-dispersible polymer, stabilizer, coloring agent, sweetening agent, preservative and the like may be mixed. The sublingual, buccal or intraoral quick disintegrating agent is obtained by mixing the above-mentioned components simultaneously or at a time interval, then subjecting the mixture to tablet-making molding under pressure. For obtaining suitable hardness, it may also be permissible that the materials are moistened by using a solvent such as water, alcohol and the like if desired before and after the tablet making process, and after the molding, the materials are dried, to obtain a product.

In the case of molding into a mucosa membrane patch (film), the compound of the present invention or the concomitant drug and the above-mentioned water-dispersible polymer (preferably, hydroxypropylcellulose, hydroxypropylmethylcellulose), excipient and the like are dissolved in a solvent such as water and the like, and the resulted solution is cast to give a film. Further, additives such as a plasticizer, stabilizer, antioxidant, preservative, coloring agent, buffer, sweetening agent and the like may also be added. For imparting suitable elasticity to the film, glycols such as polyethylene glycol, propylene glycol and the like may be contained, or for enhancing adhesion of the film to an intraoral mucosa membrane lining, a bio-adhesive polymer (e.g., polycarbophil, carbopol) may also be contained. In the casting, a solution is poured on the non-adhesive surface, spread to uniform thickness (preferably, about 10 to 1000 micron) by an application tool such as a doctor blade and the like, then, the solution is dried to form a film. It may be advantageous that thus formed film is dried at room temperature or under heat, and cut into a desired area.

As the preferable intraoral quick disintegrating agent, there are listed solid quick scattering dose agents composed of a network body comprising the compound of the present invention or the concomitant drug, and a water-soluble or water-diffusible carrier which is inert to the compound of the present invention or concomitant drug, are listed. This network body is obtained by sublimating a solvent from the solid composition constituted of a solution prepared by dissolving the compound of the present invention or the concomitant drug in a suitable solvent.

It is preferable that the composition of an intraoral quick disintegrating agent contains a matrix forming agent and a secondary component, in addition to the compound of the present invention or the concomitant drug.

Examples of the matrix forming agent include animal proteins or vegetable proteins such as gelatins, dextrins, soybean, wheat and psyllium seed protein and the like; rubber substances such as gum Arabic, guar gum, agar, xanthane gum and the like; polysaccharides; alginic acids; carboxymethylcelluloses; carageenans; dextrans; pectines; synthetic polymers such as polyvinylpyrrolidone and the like; substances derived from a gelatin-gum Arabic complex, and the like. Further, saccharides such as mannitol, dextrose, lactose, galactose, trehalose and the like; cyclic saccharides such as cyclodextrin and the like; inorganic salts such as sodium phosphate, sodium chloride and aluminum silicate and the like; amino acids having 2 to 12 carbon atoms such as glycine, L-alanine, L-aspartic acid, L-glutamic acid, L-hydroxyproline, L-isoleucine, L-leucine, L-phenylalanine and the like, are contained.

One or more of the matrix forming agents can be introduced in a solution or suspension before solidification. Such as matrix forming agent may be present in addition to a surfactant, or may be present while a surfactant being excluded. The matrix forming agents aid to maintain the compound of the present invention or the concomitant drug in the solution or suspension in diffused condition, in addition to formation of the matrix.

The composition may contain secondary components such as a preservative, antioxidant, surfactant, thickening agent, coloring agent, pH controlling agent, flavoring agent, sweetening agent, food taste masking agent and the like. As the suitable coloring agent, there are listed red, black and yellow iron oxides, and FD & C dyes such as FD & C Blue 2, FD & C Red 40 and the like manufactured by Ellis and Everard. Examples of the suitable flavoring agent include mint, raspberry, licorice, orange, lemon, grapefruit, caramel, vanilla, cherry, grape flavor and combinations thereof. Examples of the suitable pH controlling agent include citric acid, tartaric acid, phosphoric acid, hydrochloric acid and maleic acid. Examples of the suitable sweetening agent include aspartame, acesulfame K and thaumatin and the like. Examples of the suitable food taste masking agent include sodium bicarbonate, ion exchange resin, cyclodextrin-inclusion compounds, adsorbent substances and microcapsulated apomorphine.

The preparation contains the compound of the present invention or the concomitant drug in an amount usually from about 0.1 to about 5.0% by weight, preferably from about 0.1 to about 30% by weight, and preferable are preparations (such as the above-mentioned sublingual agent, buccal and the like) which can dissolve 90% or more of the compound of the present invention or the concomitant drug (into water) within the time range of about 1 to about 60 min, preferably of about 1 to about 15 min, more preferably of about 2 to about 5 min, and intraoral quick disintegrating preparations which are disintegrated within the range of 1 to 60 sec, preferably of 1 to 30 sec, further preferably of 1 to 10 sec, after placed in an oral cavity.

The content of the above-mentioned excipient in the whole preparation is from about 10 to about 99% by weight, preferably from about 30 to about 90% by weight. The content of β-cyclodextrin or β-cyclodextrin derivative in the whole preparation is from 0 to about 30% by weight. The content of the lubricant in the whole preparation is from about 0.01 to about 10% by weight, preferably from about 1 to about 5% by weight. The content of the isotonizing agent in the whole preparation is from about 0.1 to about 90% by weight, preferably, from about 10 to about 70% by weight. The content of the hydrophilic carrier in the whole preparation is from about 0.1 to about 50% by weight, preferably, from about 10 to about 30% by weight. The content of the water-dispersible polymer in the whole preparation is from about 0.1 to about 30% by weight, preferably, from about 10 to about 25% by weight. The content of the stabilizer in the whole preparation is from about 0.1 to about 10% by weight, preferably, from about 1 to 5% by weight. The above-mentioned preparation may further contain additives such as a coloring agent, sweetening agent, preservative and the like, if necessary.

The dosage of a combination agent of the present invention differs depending on the kind of a compound of the present invention, age, body weight, condition, drug form, administration method, administration period and the like, and for example, for one prostate cancer patient (adult, body weight: about 60 kg), the combination agent is administered intravenously, at a dose of about 0.01 to about 1000 mg/kg/day, preferably about 0.01 to about 100 mg/kg/day, more preferably about 0.1 to about 100 mg/kg/day, particularly about 0.1 to about 50 mg/kg/day, especially about 1.5 to about 30 mg/kg/day, in terms of the compound of the present invention or the concomitant drug, respectively, once or several times in division a day. Of course, since the dose as described above varies depending on various conditions, amounts smaller than the above-mentioned dosage may sometimes be sufficient, further, amounts over that range sometimes have to be administered.

The amount of the concomitant drug can be set at any value unless side effects are problematical. The daily dosage in terms of the concomitant drug differs depending on the severity of the symptom, age, sex, body weight, sensitivity difference of the subject, administration period, interval, and nature, pharmacy, kind of the pharmaceutical preparation, kind of effective ingredient, and the like, and not particularly restricted, and the amount of a drug is, in the case of oral administration for example, usually from about 0.001 to 2000 mg, preferably from about 0.01 to 500 mg, further preferably from about 0.1 to 100 mg, per 1 kg of a mammal and this is usually administered once to 4-times in division a day.

In administration of a combination agent of the present invention, it may be permissible that the compound of the present invention is administered after the first administration of the concomitant drugs or vice versa, though they may be administered simultaneously. When administered at a time interval, the interval differs depending on the effective ingredient to be administered, drug form and administration method, and for example, when the concomitant drug is administered first, a method in which the compound of the present invention is administered within time range of from 1 min to 3 days, preferably from 10 min to 1 day, more preferably from 15 min to 1 hr after administration of the concomitant drug is exemplified. When the compound of the present invention is administered first, a method in which the concomitant drug is administered within time range of from 1 min to 1 day, preferably from 10 min to 6 hrs, more preferably from 15 min to 1 hr after administration of the compound of the present invention is exemplified.

In a preferable administration method, for example, the concomitant drug which has been molded into an oral administration preparation is administered orally at a daily dose of about 0.001 to 200 mg/kg, and about 15 min later, the compound of the present invention which has been molded into an oral administration preparation is administered orally at a daily dose of about 0.005 to 100 mg/kg.

Furthermore, the pharmaceutical composition or the concomitant drug of the present invention can be combined with a non-drug therapy such as (1) surgery, (2) hypertensive chemotherapy using angiotensin II etc., (3) gene therapy, (4) thermotherapy, (5) cryotherapy, (6) laser cauterization, (7) radiotherapy, and the like.

For example, by using the pharmaceutical composition of the present invention or the concomitant drug of the present invention before and after an operation and the like, or by using before and after a treatment combining two or three kinds thereof, effects of prevention of resistance expression, elongation of Disease-Free Survival, suppression of cancer metastasis or recurrence, apothanasia and the like can be obtained.

In addition, a treatment with the pharmaceutical composition of the present invention or, the concomitant drug of the present invention can be combined with a supporting therapy [(i) administration of antibiotic (e.g., β-lactam such as pansporin and the like, macrolides such as clarithromycin and the like etc.) for complication with various infectious diseases, (ii) administration of high-calorie infusion, amino acid preparation or general vitamin preparation for malnutrition improvement, (iii) administration of morphine for pain mitigation, (iv) administration of pharmaceutical agent for improving side effects such as nausea, vomiting, anorexia, diarrhea, leucopenia, thrombocytopenia, hemoglobin concentration decrease, hair loss, hepatopathy, renopathy, DIC, fever and the like, and (v) administration of pharmaceutical agent for suppressing multiple drug resistance of cancer etc.].

Specific examples of a pharmaceutical agent for such object, e.g., "antiemetic", include gastric motility enhancers such as 5-$HT_3$ antagonists (e.g., ondansetron, tropisetron hydrochloride, azasetron, ramosetron, granisetron, dolasetron mesylate, palonosetron and the like); NK1 receptor antagonists (e.g., sendide, CP-99994, CP-100263, CP-122721-1, CP-96345, FK224, RPR100893, NKP608, aprepitant (EMEND (trademark)) and the like; 5-$HT_4$ antagonists (e.g., domperidone, mosapride, metoclopramide and the like), and the like; gastrointestinal tract motility regulators such as trimebutine and the like; phenothiazine pharmaceutical agents such as prochlorperazine maleate, promethazine, thiethylperazine and the like; tranquilizers such as haloperidol, chlorpromazine phenolphthalinate, diazepam, droperidol and the like; steroids such as dexamethasone, prednisolone, betamethasone, triamcinolone and the like; as well as dimethylhydrin acid, diphenhydramine, hyoscine, hyoscine hydrobromide, tetrabenazine and the like.

Preferably, the pharmaceutical composition of the present invention or the combination agent of the present invention is administered orally (including sustained-release preparations), intravenously (including boluses, infusions and clathrates), subcutaneously and intramuscularly (including boluses, infusions and sustained-release preparations), transdermally, intratumorally or proximally before or after the above-described treatment is conducted.

As a period for administration of the pharmaceutical composition of the present invention or the combination agent of the present invention before the surgery, etc., for example, it can be administrated once about 30 min to 24 hr before the surgery, etc., or in 1 to 3 cycles about 3 to 6 months before the surgery, etc. In this way, the surgery, etc. can be conducted easily because, for example, a cancer tissue can be reduced by administering the pharmaceutical composition of the present invention or the combination agent of the present invention before the surgery, and the like.

As a period for administration of the pharmaceutical composition of the present invention or the combination agent of the present invention after the surgery and the like, for example, it can be administrated repeatedly about 30 min to 24 hr after the surgery, and the like in a unit of several weeks to 3 months. In this way, the effect of the surgery and the like can be enhanced by administering the pharmaceutical composition of the present invention or the combination agent of the present invention after the surgery and the like.

EXAMPLES

The present invention is explained in detail in the following by referring to Reference Examples, Examples, Formulation Examples and Experimental Examples, which are not to be construed as limitative.

The elution by column chromatography in Reference Examples and Examples was performed under observation by TLC (Thin Layer Chromatography). In the observation by TLC, Kieselgel 60 $F_{254}$ plate manufactured by Merck was used as a TLC plate, the solvent used as an elution solvent in column chromatography was used as a developing solvent, and a UV detector was adopted as a detection method. The silica gel for the column used was also Kieselgel 60 $F_{254}$ (70-230 mesh) manufactured by Merck. The NMR spectrum shows proton NMR, VARIAN Gemini-200 (200 MHz type spectrometer), VARIAN Mercury-300 (300 MHz) or JMTCO 400/54 (JEOL Ltd., 400 MHz) was used for the measurement with tetramethylsilane as the internal standard, and δ value is shown in ppm. The reaction using a microwave reaction apparatus was performed using Emrys Optimizer manufactured by Biotage Ltd.

The infrared absorption spectrum (IR) was measured using Paragon 1000 manufactured by PerkinElmer Inc.

The abbreviations used in the Reference Examples and Examples mean the following.
s: singlet
br: broad
d: doublet
t: triplet
q: quartet
dd: double doublet
ddd: double double doublet
dt: double triplet
m: multiplet
J: coupling constant
Hz: hertz
THF: tetrahydrofuran
DMSO: dimethyl sulfoxide
DMF: N,N-dimethylformamide Reference Example 1

Production of 2-chloro-4-fluoro-3-methylbenzonitrile

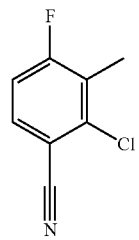

To a solution (60 ml) of 2-chloro-4-fluoro-3-methylbenzoic acid (5.66 g) synthesized by a known method in THF were added thionyl chloride (10.7 g) and DMF (0.2 ml) with stirring under ice-cooling, and the mixture was stirred at 70° C. for 3 hr. The solvent was evaporated under reduced pressure, and the residue was dissolved in dry THF (50 ml) and added dropwise to a mixture of concentrated aqueous ammonia (130 ml) and THF (86 ml) with stirring under ice-cooling. The mixture was stirred at the same temperature for 1 hr and extracted with ethyl acetate. The organic layer was washed with saturated brine and dried over anhydrous sodium sulfate. The solvent was evaporated under reduced pressure, and the precipitated crystals were collected by filtration, washed with diethyl ether and dried to give 2-chloro-4-fluoro-3-methylbenzamide (4.82 g) as crystals.

$^{1}$H-NMR (CDCl$_{3}$) δ: 2.35 (3H, d), 5.93 (1H, s), 6.19 (1H, s), 7.04 (1H, t), 7.57 (1H, dd).

To a solution (50 ml) of 2-chloro-4-fluoro-3-methylbenzamide (4.69 g) and pyridine (2.97 g) in DMF was added dropwise oxalyl chloride (3.80 g) with stirring under ice-cooling at not more than 10° C. After stirring at the same temperature for 1 hr, the mixture was poured into ethyl acetate/water and partitioned. The organic layer was washed with water, aqueous sodium hydrogencarbonate solution and saturated brine, and dried over anhydrous sodium sulfate. The solvent was evaporated under reduced pressure, and the precipitated crystals were collected by filtration, washed with cold hexane and dried to give the title compound (3.00 g) as crystals.

$^{1}$H-NMR (CDCl$_{3}$) δ: 2.36 (3H, d), 7.07 (1H, t), 7.54 (1H, dd).

Reference Example 2

(4S,5S)-4-hydroxy-5-methylpyrrolidin-2-one

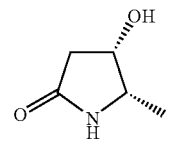

To a mixture of tert-butyl (2S,3S)-3-hydroxy-2-methyl-5-oxopyrrolidine-1-carboxylate (1.00 g) synthesized by a known method and ethyl acetate (10 ml) was added dropwise 4N hydrogen chloride-ethyl acetate (3.5 ml) at room temperature, and the mixture was stirred for 30 min. The solvent was evaporated under reduced pressure and the residue was dissolved in methanol (10 ml). The obtained solution was added to a suspension of Amberlyst A-21 (3.2 g, washed with methanol before use) in methanol (20 ml), and the mixture was stirred at room temperature for 30 min. Amberlyst A-21 was filtered off and washed with methanol (10 ml×4). The mother liquor and washing solution were combined and toluene was added thereto. The solvent was evaporated under reduced pressure. The obtained residue was recrystallized from a mixture of methanol and diisopropylether to give the title compound (389 mg) as crystals.

mp 139-140° C.

$^1$H-NMR (DMSO-$d_6$) δ: 1.03 (3H, d), 1.95 (1H, dd), 2.39 (1H, dd), 3.52-3.61 (1H, m), 4.10-4.17 (1H, m), 4.93 (1H, d), 7.50 (1H, br).

Reference Example 3

(2S,3S)-3-(1-hydroxy-1-methylethyl)-2-methylpyrrolidine 1/2oxalate (compound 1)

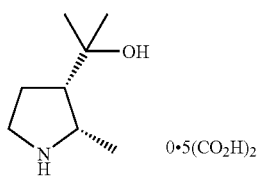

A mixture of 2-[(2S,3S)-2-methyl-1-[(1S)-1-phenylethyl]pyrrolidin-3-yl]propan-2-ol (2.00 g) synthesized by a known method, 10% palladium-carbon (50% water-containing product, 172 mg) and methanol (30 ml) was stirred under a hydrogen atmosphere at room temperature for 60 hr. The catalyst was removed by filtration through celite, and the mother liquor was concentrated. The obtained oily substance was dissolved in methanol, oxalic acid dihydrate (510 mg) was added thereto, and the mixture was concentrated. The residue was crystallized from diethyl ether to give the title compound (1.47 g, 1/2 hydrate).

mp 120-122° C.

$^1$H-NMR (DMSO-$d_6$) δ: 1.128 (3H, s), 1.129 (3H, d), 1.17 (3H, s), 1.74-2.08 (3H, m), 3.01-3.19 (2H, m), 3.56-3.65 (1H, m).

Example 1

2-chloro-4-[(2S,3S)-3-(1-hydroxy-1-methylethyl)-2-methylpyrrolidin-1-yl]-3-methylbenzonitrile (compound 2)

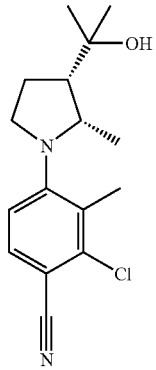 [SMILES: Cc1c(N2CC[C@H](C(C)(C)O)[C@@H]2C)ccc(C#N)c1Cl]

A mixture of compound 1 (1.56 g), 2-chloro-4-fluoro-3-methylbenzonitrile (1.27 g), lithium carbonate (1.16 g) and DMSO (37.5 ml) was stirred at 100° C. for 1 hr. The reaction mixture was cooled and partitioned between water and ethyl acetate. The organic layer was washed with water, dried (sodium sulfate), and concentrated. The obtained residue was purified by silica gel column chromatography (ethyl acetate-hexane), and crystallized from ethyl acetate-hexane to give the title compound (357 mg) as crystals.

$^1$H-NMR (CDCl$_3$) δ: 0.95 (3H, d), 1.24 (1H, s), 1.31 (3H, s), 1.36 (3H, s), 2.04-2.13 (2H, m), 2.31 (3H, s), 2.34-2.41 (1H, m), 3.06-3.15 (1H, m), 3.58-3.66 (1H, m), 4.04-4.14 (1H, m), 6.80 (1H, d), 7.39 (1H, d).

IR(KBr):3470, 2971, 2226, 1586, 1474 cm$^{-1}$.

Example 1 (1)

2-chloro-4-[(2S,3S)-3-(1-hydroxy-1-methylethyl)-2-methylpyrrolidin-1-yl]benzonitrile (compound 3)

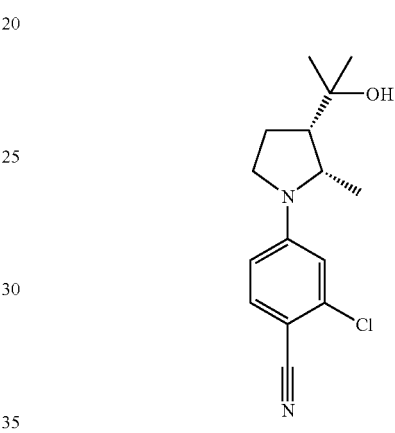

Using compound 1 and 2-chloro-4-fluorobenzonitrile as starting materials, the title compound was obtained by the same manner as shown in Example 1.

$^1$H-NMR (CDCl$_3$) δ: 1.21 (3H, d), 1.21 (1H, s), 1.34 (3H, s), 1.39 (3H, s), 2.07-2.24 (3H, m), 3.21-3.30 (1H, m), 3.43 (1H, t), 4.03 (1H, m), 6.39 (1H, dd), 6.53 (1H, d), 7.40 (1H, d).

IR(KBr):2975, 2216, 1601, 1514, 1389 cm$^{-1}$.

Example 1 (2)

4-[(2S,3S)-3-(1-hydroxy-1-methylethyl)-2-methylpyrrolidin-1-yl]-3-methylbenzonitrile (compound 4)

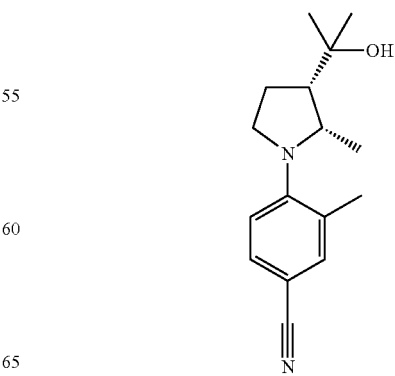

Using compound 1 and 4-fluoro-3-methylbenzonitrile as starting materials, the title compound was obtained by the same manner as shown in Example 1 (reaction temperature 90° C., reaction time 3 hr).

$^1$H-NMR (CDCl$_3$) δ: 0.99 (3H, d), 1.29 (1H, s), 1.31 (3H, s), 1.37 (3H, s), 2.02-2.12 (2H, m), 2.33 (3H, s), 2.29-2.38 (1H, m), 3.20-3.28 (1H, m), 3.60-3.68 (1H, m), 4.21-4.30 (1H, m), 6.73 (1H, d), 7.31 (1H, d), 7.36 (1H, dd).

Example 1 (3)

4-[(2S,3S)-3-(1-hydroxy-1-methylethyl)-2-methylpyrrolidin-1-yl]benzonitrile (compound 5)

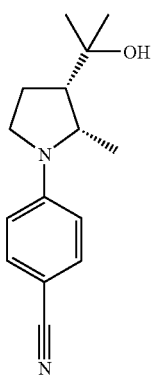 [SMILES: C[C@H]1[C@@H](C(C)(C)O)CCN1c1ccc(C#N)cc1]

Using compound 1 and 4-fluorobenzonitrile as starting materials, the title compound was obtained by the same manner as shown in Example 1 (reaction temperature 90° C., reaction time 3 hr).

$^1$H-NMR (CDCl$_3$) δ: 1.20 (3H, d), 1.24 (1H, s), 1.33 (3H, s), 1.39 (3H, s), 2.06-2.22 (3H, m), 3.21-3.30 (1H, m), 3.40-3.46 (1H, m), 4.02-4.10 (1H, m), 6.49 (2H, d), 7.44 (2H, d).

Example 2

2-chloro-4-[(2S,3S)-3-hydroxy-2-methylpyrrolidin-1-yl]-3-methylbenzonitrile (compound 6)

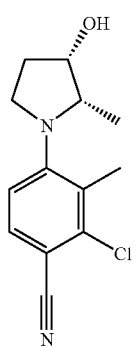 [SMILES: Cc1c(N2CC[C@H](O)[C@@H]2C)ccc(C#N)c1Cl]

To a suspension (13 ml) of (4S,5S)-4-hydroxy-5-methylpyrrolidin-2-one (317 mg) in dry THF was added dropwise Red-Al (3.07 g; 70% toluene solution) under ice cooling, under a nitrogen stream. The mixture was stirred at room temperature for 20 min, and refluxed for 3 hr. The reaction mixture was ice-cooled again, and sodium carbonate decahydrate (1.26 g) was added thereto under a nitrogen stream. The reaction mixture was stirred at room temperature overnight, an insoluble material was filtered through celite, and washed with THF. The filtrate and the washing solution were combined, and concentrated under reduced pressure to give (2S, 3S)-3-hydroxy-2-methylpyrrolidine. The present compound was used for the next step without further purification.

A mixture of (2S,3S)-3-hydroxy-2-methylpyrrolidine, 2-chloro-4-fluoro-3-methylbenzonitrile (424 mg), lithium carbonate (370 mg) and DMSO (12.5 ml) was stirred at 100° C. for 2 hr. The reaction mixture was cooled and partitioned between water and ethyl acetate. The organic layer was washed with water, dried (sodium sulfate), and concentrated. The obtained residue was purified by silica gel column chromatography (ethyl acetate-hexane), and crystallized from ethyl acetate-hexane to give the title compound (114 mg) as crystals.

$^1$H-NMR (CDCl$_3$) δ: 1.13 (3H, d), 1.77 (1H, d), 1.98-2.09 (2H, m), 2.34 (3H, s), 2.86-2.93 (1H, m), 3.72-3.79 (1H, m), 3.88-3.97 (1H, m), 4.35-4.42 (1H, m), 6.80 (1H, d), 7.41 (1H, d).

Example 2 (1)

2-chloro-4-[(2S,3S)-3-hydroxy-2-methylpyrrolidin-1-yl]benzonitrile (compound 7)

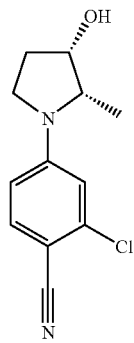 [SMILES: C[C@H]1[C@@H](O)CCN1c1ccc(C#N)c(Cl)c1]

Using (4S,5S)-4-hydroxy-5-methylpyrrolidin-2-one and 2-chloro-4-fluorobenzonitrile as starting materials, the title compound was obtained by the same manner as shown in Example 2 (reaction time 1 hr).

$^1$H-NMR (CDCl$_3$) δ: 1.18 (3H, d), 1.82 (1H, d), 2.01-2.14 (1H, m), 2.25-2.35 (1H, m), 3.19-3.28 (1H, m), 3.43-3.51 (1H, m), 3.89-3.98 (1H, m), 4.43-4.52 (1H, m), 6.43 (1H, dd), 6.56 (1H, d), 7.41 (1H, d).

Example 2 (2)

4-[(2S,3S)-3-hydroxy-2-methylpyrrolidin-1-yl]benzonitrile (compound 8)

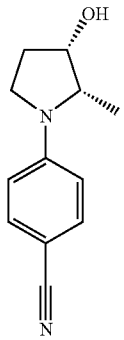

Using (4S,5S)-4-hydroxy-5-methylpyrrolidin-2-one and 4-fluorobenzonitrile as starting materials, the title compound was obtained by the same manner as shown in Example 2 (reaction time 1 hr).

$^1$H-NMR (CDCl$_3$) δ: 1.18 (3H, d), 1.72 (1H, s), 2.04-2.14 (1H, m), 2.25-2.35 (1H, m), 3.19-3.28 (1H, m), 3.43-3.50 (1H, m), 3.90-4.00 (1H, m), 4.41-4.52 (1H, m), 6.53 (2H, d), 7.44 (2H, d).

Reference Example 4

2-chloro-3,4-difluorobenzoic acid (compound 9)

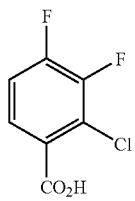

To a mixture of N,N,N',N'-tetramethylethylenediamine (8.40 mL) and tetrahydrofuran (75 mL) was added sec-butyllithium (1.0 mol/L cyclohexane solution, 55.7 mL) under an argon atmosphere at −78° C., and the mixture was stirred for 30 min. A mixture of 3,4-difluorobenzoic acid (4.00 g) and tetrahydrofuran (25 mL) was added dropwise to the reaction mixture at the same temperature over 30 min. After the reaction mixture was stirred for 30 min, a mixture of hexachloroethane (24.0 g) and tetrahydrofuran (40 mL) was added dropwise to the reaction mixture at the same temperature over 30 min. After stirring for 30 min while raising the temperature to room temperature, the reaction mixture was poured into water. The aqueous layer was washed with diisopropyl ether, acidified with 6 mol/L hydrochloric acid and extracted with diethyl ether. The organic layer was washed with brine, dried over anhydrous sodium sulfate, and concentrated. The obtained residue was washed with diethyl ether to give the title product as a solid (yield: 2.95 g).

$^1$H-NMR (DMSO-d$_6$) δ: 7.51-7.60 (1H, m), 7.73-7.78 (1H, m), 13.7 (1H, br s).

mp: 167-168° C.

Reference Example 5

2-chloro-3,4-difluorobenzamide (compound 10)

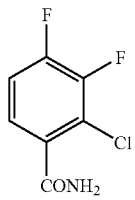

To a mixture of 2-chloro-3,4-difluorobenzoic acid (2.50 g), 1-(3-dimethylaminopropyl)-3-ethylcarbodiimide hydrochloride (2.99 g), 1-hydroxybenztriazole (2.39 g) and N,N-dimethylformamide (72 mL) was added 28% aqueous ammonia (1.6 mL) at room temperature, and the mixture was stirred for 40 hr. The reaction mixture was poured into water and extracted with ethyl acetate. The organic layer was washed with water, dried over anhydrous sodium sulfate, and concentrated. The obtained residue was purified by silica gel column chromatography (developing solvent: ethyl acetate-hexane). The obtained solid was washed with dichloromethane to give the title compound as a solid (yield: 1.30 g).

$^1$H-NMR (DMSO-d$_6$) δ: 7.33-7.38 (1H, m), 7.48-7.56 (1H, m), 7.74 (1H, br s), 7.97 (1H, br s).

mp: 142-143° C.

Reference Example 6

2-chloro-3,4-difluorobenzonitrile (compound 11)

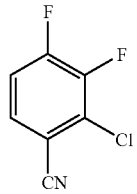 [SMILES: N#Cc1ccc(F)c(F)c1Cl]

To a mixture of 2-chloro-3,4-difluorobenzamide (1.20 g), pyridine (1.01 mL) and N,N-dimethylformamide (18 mL) was added oxalyl chloride (0.82 mL) at 0° C. over 10 min. The mixture was stirred for 1 hr while raising the temperature to room temperature. The reaction mixture was poured into water and extracted with ethyl acetate. The organic layer was washed with water, dried over anhydrous sodium sulfate and concentrated. The obtained residue was purified by silica gel column chromatography (developing solvent: ethyl acetate-hexane) to give the title compound as a solid (yield: 983 mg).

$^1$H-NMR (CDCl$_3$) δ: 7.20-7.29 (1H, m), 7.48-7.53 (1H, m).

Reference Example 7

1-chloro-3-fluoro-2-vinylbenzene (compound 12)

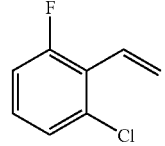

Under an argon atmosphere, to a suspension (1.1 L) of methyltriphenylphosphonium bromide (90 g) in dry tetrahydrofuran was added a solution (264 mL) of 1 mol/L-potassium tert-butoxide in tetrahydrofuran with stirring under ice-cooling, and the mixture was stirred at the same temperature for 30 min. Then, a solution (165 mL) of 2-chloro-6-fluorobenzaldehyde (34.5 g) in tetrahydrofuran was added to the mixture, and the mixture was stirred for 30 min. The insoluble material was removed with celite, and the filtrate was concentrated under reduced pressure. Ethyl acetate was added to the residue and, after triturating, the crystals were collected by filtration and concentrated. The residue was purified by silica gel column chromatography (developing solvent: hexane) using NH-silica gel (manufactured by Fuji Silysia Chemical Ltd.) to give the title compound as a colorless oil (yield: 20.7 g).

$^1$H-NMR (CDCl$_3$) δ: 5.62-5.68 (1H, m), 5.98-6.01 (1H, m), 6.77-6.87 (1H, m), 6.96-7.03 (1H, m), 7.09-7.21 (2H, m).

Reference Example 8

1-chloro-2-ethyl-3-fluorobenzene (compound 13)

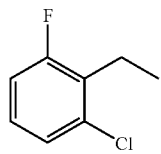

To a solution (120 mL) of 1-chloro-3-fluoro-2-vinylbenzene (9.45 g) in ethyl acetate were added sodium acetate (4.92 g) and 10% Pd/C (50% water-containing product, 0.95 g), and the mixture was vigorously stirred under a hydrogen atmosphere. The catalyst was filtered off, and the filtrate was concentrated. The residue was partitioned with ethyl acetate-water. The organic layer was washed with saturated brine, dried over anhydrous sodium sulfate, and concentrated to give the title compound as a colorless oil (yield: 8.4 g).

$^1$H-NMR (CDCl$_3$) δ: 1.18 (3H, t), 2.80 (2H, q), 6.91-6.97 (1H, m), 7.04-7.16 (2H, m).

Reference Example 9

1-(2-chloro-3-ethyl-4-fluorophenyl)ethanone (compound 14)

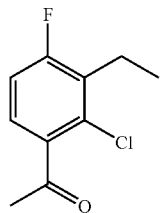

A mixture of 1-chloro-2-ethyl-3-fluorobenzene (8.0 g) and anhydrous aluminum chloride (13.09 g) was stirred at 40° C., acetyl chloride (3 drops) was added thereto, and the mixture was stirred for 10 min. The mixture was cooled to room temperature, acetyl chloride (3.9 g) was added to the mixture, and the mixture was stirred at room temperature for 2 hr. The reaction mixture was poured into ice water, and 2 mol/L hydrochloric acid was added thereto. The mixture was extracted with methylene chloride (240 mL), washed with water, dried over anhydrous sodium sulfate and concentrated. The residue was purified by silica gel column chromatography (developing solvent: hexane-ethyl acetate) to give the title compound as a colorless oil (yield: 3.84 g).

$^1$H-NMR (CDCl$_3$) δ: 1.19 (3H, t), 2.63 (3H, s), 2.86 (2H, dq), 7.01 (1H, t), 7.35 (1H, dd).

Reference Example 10

2-chloro-3-ethyl-4-fluorobenzoic acid (compound 15)

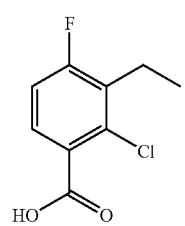

Bromine (8.94 g) was added to an aqueous solution (35.6 mL) of sodium hydroxide (7.61 g) with stirring at 10° C., and a solution (37.4 mL) of 1-(2-chloro-3-ethyl-4-fluorophenyl)ethanone (3.74 g) in dioxane was added under ice-cooling (sodium chloride-ice bath). The mixture was warmed to room temperature and, after stirring for 1 hr, poured into water and partitioned with chloroform. The aqueous layer was adjusted to pH=3 with concentrated hydrochloric acid, and extracted with ether. The organic layer was washed with saturated brine, dried over anhydrous sodium sulfate, and concentrated to give the title compound as colorless crystals (yield: 3.33 g).

$^1$H-NMR (CDCl$_3$) δ: 1.20 (3H, t), 2.90 (2H, dq), 7.04 (1H, t), 7.86 (1H, dd).

Reference Example 11

2-chloro-3-ethyl-4-fluorobenzamide (compound 16)

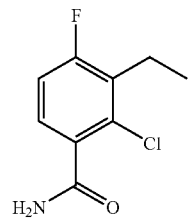

To a solution (32 mL) of 2-chloro-3-ethyl-4-fluorobenzoic acid (3.25 g) in tetrahydrofuran were added thionyl chloride (5.71 g) and N,N-dimethylformamide (3 drops) with stirring under ice-cooling, and the mixture was stirred at 70° C. for 2 hr. The mixture was cooled to room temperature and concentrated. The residue was dissolved in dry tetrahydrofuran (25 mL), added to an ice-cooled 28% aqueous ammonia (69 mL)-tetrahydrofuran (46 mL) mixture and vigorously stirred for 1 hr. The reaction mixture was partitioned between ethyl acetate-saturated brine, and the organic layer was dried over anhydrous sodium sulfate, and concentrated to give the title compound colorless crystals (yield: 2.92 g).

$^1$H-NMR (CDCl$_3$) δ: 1.19 (3H, t), 2.86 (2H, dq), 6.20 (2H, brs), 7.02 (1H, t), 7.53 (1H, dd).

Reference Example 12

2-chloro-4-fluoro-3-ethylbenzonitrile (compound 17)

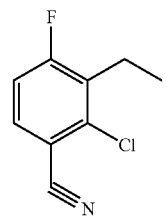

Using 2-chloro-3-ethyl-4-fluorobenzamide (2.83 g), the title compound was obtained as colorless crystals (yield: 2.48 g) by an operation similar to that in Reference Example 6.

$^1$H-NMR (CDCl$_3$) δ: 1.20 (3H, t), 2.85 (2H, dq), 7.07 (1H, t), 7.54 (1H, dd).

Reference Example 13

1,2-dichloro-3-fluoro-4-methylbenzene (compound 18)

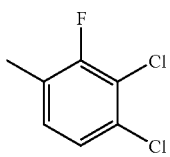

Under an argon atmosphere, to a solution (75 mL) of N,N,N',N'-tetramethylethylenediamine (16.15 g) in dry tetrahydrofuran was added a solution (139 mL) of 1 mol/L-sec-butyllithium in hexane/cyclohexane under cooling (dry ice-acetone bath) at not higher than −60° C., and the mixture was stirred at the same temperature for 20 min. The mixture was further cooled to −78° C., and a solution (50 mL) of 4-chloro-2-fluoro-1-methylbenzene (18.26 g) in dry tetrahydrofuran was added thereto. After the reaction mixture was stirred at the same temperature for 30 min, a solution (275 mL) of hexachloroethane (119.6 g) in dry tetrahydrofuran was added dropwise thereto. The mixture was stirred at the same temperature for 30 min to gradually warm to room temperature. To the reaction mixture was added 6 mol/L hydrochloric acid to adjust to pH=5 and the mixture was concentrated. The residue was partitioned between ether and water, and the organic layer was washed with saturated brine, dried over anhydrous magnesium sulfate and concentrated. The residue was placed on a glass filter, washed with a small amount of ether and filtrated. The filtrate was concentrated and evaporated under reduced pressure. The fraction at the boiling point of 48° C. (1.5 Torr) was collected to give the title compound as a colorless oil (yield: 19 g).

$^1$H-NMR (CDCl$_3$) δ: 2.27 (3H, s), 7.01 (1H, t), 7.14 (1H, d).

Reference Example 14

1-(2,3-dichloro-4-fluoro-5-methylphenyl)ethanone (compound 19)

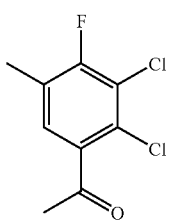

Using 1,2-dichloro-3-fluoro-4-methylbenzene (12.0 g), anhydrous aluminum chloride (17.87 g) and acetyl chloride (5.26 g), the title compound was obtained as a pale-yellow oil (yield: 5.46 g) by an operation similar to that in Reference Example 9.

$^1$H-NMR (CDCl$_3$) δ: 2.32 (3H, d), 2.63 (3H, s), 7.30 (1H, d).

Reference Example 15

2,3-dichloro-4-fluoro-5-methylbenzoic acid (compound 20)

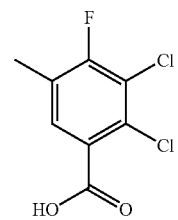

Using 1-(2,3-dichloro-4-fluoro-5-methylphenyl)ethanone (6.64 g), the title compound was obtained as colorless crystals (yield: 5.87 g) by an operation similar to that in Reference Example 10.

$^1$H-NMR (CDCl$_3$) δ: 2.34-2.35 (3H, m), 7.81 (1H, d).

Reference Example 16

2,3-dichloro-4-fluoro-5-methylbenzamide (compound 21)

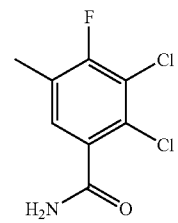

Using 2,3-dichloro-4-fluoro-5-methylbenzoic acid (5.42 g), the title compound was obtained as colorless crystals (yield: 4.75 g) by an operation similar to that in Reference Example $^1$H-NMR (DMSO-d$_6$) δ: 2.29 (3H, d), 7.41 (1H, d), 7.69 (1H, s 7.92 (1H, s).

Reference Example 17

2,3-dichloro-4-fluoro-5-methylbenzonitrile (compound 22)

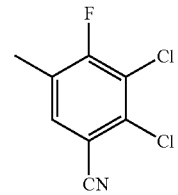

Using 2,3-dichloro-4-fluoro-5-methylbenzamide (4.44 g), the title compound was obtained as colorless crystals (yield: 3.70 g) by an operation similar to that in Reference Example 6.

$^1$H-NMR (CDCl$_3$) δ: 2.34-2.35 (3H, m), 7.46 (1H, d).

Reference Example 18

2-chloro-4-fluoro-5-methylbenzonitrile (compound 23)

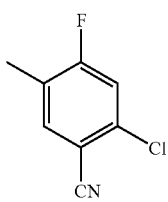

Under an argon atmosphere, to a solution (20 mL) of 1-bromo-2-chloro-4-fluoro-5-methylbenzene (4.47 g) in N,N-dimethylformamide were added tetrakis(triphenylphosphine)palladium(0) (0.78 g) and zinc cyanide (1.23 g). The mixture was stirred at 110° C. for 13 hr and partitioned between ethyl acetate-water. The organic layer was washed with saturated brine, dried over anhydrous magnesium sulfate, and concentrated. The residue was purified by silica gel column chromatography (developing solvent: hexane-ethyl acetate) and crystallized from ethyl acetate-hexane to give the title compound as a colorless solid (yield: 2.3 g).

$^1$H-NMR (CDCl$_3$) δ: 2.29 (3H, d), 7.19 (1H, d), 7.52 (1H, d).

Reference Example 19

3,4,5-trifluorobenzamide (compound 24)

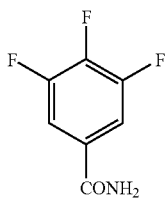 [SMILES: NC(=O)c1cc(F)c(F)c(F)c1]

3,4,5-Trifluorobenzoic acid (1.00 g) was dissolved in N,N-dimethylformamide (15 mL), and 1-(3-dimethylaminopropyl)-3-ethylcarbodiimide hydrochloride (1.31 g) and N-hydroxysuccinimide (785 mg) were added thereto at 0° C. The mixture was stirred at room temperature for 3 hr. 28% Aqueous ammonia solution (2 mL) was added to the mixture at 0° C. and the mixture was stirred at room temperature for 30 min. Water was added to the mixture and the mixture was extracted with ethyl acetate. The extract was dried over anhydrous magnesium sulfate and concentrated under reduced pressure. The residue was purified by silica gel column chromatography (developing solvent: ethyl acetate-hexane=1:2→3:1) and recrystallized from a mixed solvent of isopropyl ether and hexane to give the title compound as colorless crystals (yield: 734 mg).

$^1$H-NMR (CDCl$_3$) δ: 5.50-6.12 (2H, m), 7.48 (2H, t).

Reference Example 20

3,4,5-trifluorobenzonitrile (compound 25)

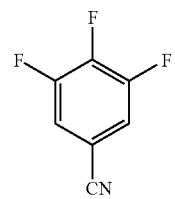 [SMILES: N#Cc1cc(F)c(F)c(F)c1]

Using 3,4,5-trifluorobenzamide (297 mg), the title compound was obtained as a yellow oil (yield: 353 mg) by an operation similar to that in Reference Example 6.

$^1$H-NMR (CDCl$_3$) δ: 7.36 (2H, t).

Reference Example 21

4-fluoro-2-methoxybenzamide (compound 26)

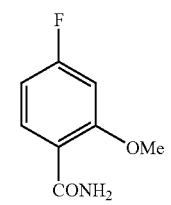 [SMILES: COc1cc(F)ccc1C(N)=O]

Using 4-fluoro-2-methoxybenzoic acid (1.00 g), the title compound was obtained as a colorless solid (yield: 875 mg) by an operation similar to that in Reference Example 19.

25 $^1$H-NMR (CDCl$_3$) δ: 3.98 (3H, s), 5.56-5.82 (1H, m), 6.60-6.90 (2H, m), 7.44-7.68 (1H, m), 8.24 (1H, dd).

Reference Example 22

4-fluoro-2-methoxybenzonitrile (compound 27)

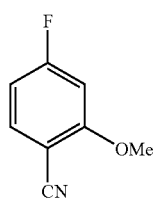 [SMILES: COc1cc(F)ccc1C#N]

Using 4-fluoro-2-methoxybenzamide (300 mg), the title compound was obtained as a yellow solid (yield: 352 mg) by an operation similar to that in Reference Example 6.

$^1$H-NMR (CDCl$_3$) δ: 3.93 (3H, s), 6.60-6.80 (2H, m), 7.56 (1H, dd).

Reference Example 23

2,4,5-trifluorobenzamide (compound 28)

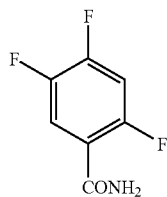

Using 2,4,5-trifluorobenzoic acid (1.00 g), the title compound was obtained as a colorless solid (yield: 574 mg) by an operation similar to that in Reference Example 19.

$^1$H-NMR (CDCl$_3$) δ: 5.78 (1H, br s), 6.61 (1H, br s), 6.90-7.12 (1H, m), 7.85-8.15 (1H, m).

Reference Example 24

2,4,5-trifluorobenzonitrile (compound 29)

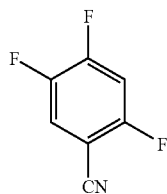 [SMILES: N#Cc1cc(F)c(F)cc1F]

Using 2,4,5-trifluorobenzamide (300 mg), the title compound was obtained as a colorless solid (yield: 153 mg) by an operation similar to that in Reference Example 6.

$^1$H-NMR (CDCl$_3$) δ: 7.03-7.25 (1H, m), 7.40-7.60 (1H, m).

Reference Example 25

4-fluoro-3-methoxybenzamide (compound 30)

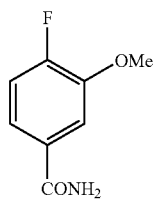

Using 4-fluoro-3-methoxybenzoic acid (1.00 g), the title compound was obtained as a colorless solid (yield: 601 mg) by an operation similar to that in Reference Example 19.

$^1$H-NMR (CDCl$_3$) δ: 3.95 (3H, s), 5.30-6.25 (2H, m), 7.12 (1H, dd), 7.23-7.29 (1H, m), 7.56 (1H, dd).

Reference Example 26

4-fluoro-3-methoxybenzonitrile (compound 31)

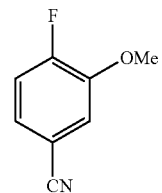 [SMILES: COc1cc(C#N)ccc1F]

Using 4-fluoro-3-methoxybenzamide (300 mg), the title compound was obtained as an orange solid (yield: 232 mg) by an operation similar to that in Reference Example 6.

$^1$H-NMR (CDCl$_3$) δ: 7.05-7.35 (3H, m), 3.93 (3H, s).

Reference Example 27

2-chloro-3-(1,3-dioxolan-2-yl)-6-fluorobenzaldehyde (compound 32)

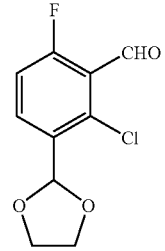 [SMILES: O=Cc1c(F)ccc(C2OCCO2)c1Cl]

To a solution of diisopropylamine (4.25 mL) in tetrahydrofuran (25 ml) was added dropwise 1.6 mol/L solution (18.9 mL) of n-butyllithium in hexane at −78° C., and the mixture was stirred at 0° C. for 1 hr. To the prepared lithium diisopropylamide was added dropwise a solution of 2-(2-chloro-4-fluorophenyl)-1,3-dioxolane (5.34 g) in tetrahydrofuran (25 mL) at −78° C. The mixture was stirred at the same temperature for 1 hr, and N,N-dimethylformamide (2.3 mL) was added thereto. The reaction mixture was stirred for 30 min, and acetic acid was added thereto. After the temperature of the reaction mixture was raised to room temperature, water was added to the mixture, and the mixture was extracted with ethyl acetate. The extract was dried over anhydrous magnesium sulfate and concentrated under reduced pressure. The obtained residue was purified by silica gel column chromatography (developing solvent: hexane-ethyl acetate=9:1→1:1) and recrystallized from hexane to give the title compound as a colorless solid (yield: 3.96 g).

$^1$H-NMR (CDCl$_3$) δ: 4.00-4.30 (4H, m), 6.16 (1H, s), 7.00-7.20 (1H, m), 7.75-7.95 (1H, m), 10.49 (1H, s).

Reference Example 28

2-chloro-1-(dimethoxymethyl)-4-fluoro-3-propyl-benzene (compound 33)

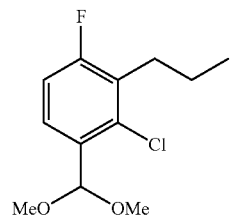 [SMILES: CCCc1c(F)ccc(C(OC)OC)c1Cl]

To a solution of ethyltriphenylphosphonium bromide (3.43 g) in tetrahydrofuran (15 mL) was added potassium tert-butoxide (1.31 g) at 0° C., and the mixture was stirred at room temperature for 1 hr. Successively, 2-chloro-3-(1,3-dioxolan-2-yl)-6-fluorobenzaldehyde (1.35 g) was added to the mixture, and the mixture was stirred for 2.5 hr. To the reaction mixture was added saturated brine, and the mixture was extracted with ethyl acetate. The extract was dried over anhydrous magnesium sulfate and concentrated under reduced pressure to give crude 2-{2-chloro-4-fluoro-3-[prop-1-en-1-yl]phenyl}-1,3-dioxolane (1.41 g).

To a solution of the obtained 2-{2-chloro-4-fluoro-3-[prop-1-en-1-yl]phenyl}-1,3-dioxolane (1.41 g) in methanol (20 ml) was added finely shredded palladium-fibroin (200 mg), and the mixture was vigorously stirred under a hydrogen atmosphere for 12 hr. The reaction mixture was filtered by suction through a glass filter with a layer of celite, and the filtrate was concentrated under reduced pressure. The residue was purified by silica gel column chromatography (developing solvent: hexane-ethyl acetate=30:1→3:1) to give the title compound as a colorless oil (yield: 1.34 g).

$^1$H-NMR (CDCl$_3$) δ: 0.97 (3H, t), 1.56-1.66 (2H, m), 2.71-2.87 (2H, m), 3.38 (6H, s), 5.60 (1H, s), 6.97 (1H, t), 7.45 (1H, dd).

Reference Example 29

2-chloro-4-fluoro-3-propylbenzaldehyde (compound 34)

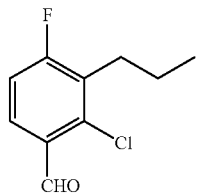

2-Chloro-1-(dimethoxymethyl)-4-fluoro-3-propylbenzene (1.20 g) was dissolved in a mixed solvent of tetrahydrofuran (16 mL)-1 mol/L hydrochloric acid (8 ml), and the mixture was heated under reflux for 2 hr. To the reaction mixture were added water and ethyl acetate, and the mixture was extracted with ethyl acetate. The obtained extract was dried over anhydrous magnesium sulfate. The ethyl acetate solvent was concentrated under reduced pressure, and the obtained residue was purified by silica gel column chromatography (developing solvent: hexane-ethyl acetate=30:1→3:1) to give the title compound as a colorless oil (yield: 970 mg).

$^1$H-NMR (CDCl$_3$) δ: 1.00 (3H, t), 1.49-1.77 (2H, m), 2.77-2.91 (2H, m), 7.07 (1H, t), 7.82 (1H, dd), 10.45 (1H, s).

Reference Example 30

2-chloro-4-fluoro-3-propylbenzonitrile (compound 35)

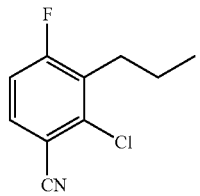

To a solution of 2-chloro-4-fluoro-3-propylbenzaldehyde (877 mg) in 1-methyl-2-pyrrolidone (15 mL) was added hydroxyammonium hydrochloride (383 mg), and the mixture was stirred at 100° C. for 1 hr. The reaction mixture was ice-cooled, thionyl chloride (1.00 mL) was added dropwise thereto, and the mixture was stirred at the same temperature for 10 min. Water was added to the mixture and the mixture was extracted with ethyl acetate. The extract was washed with saturated brine, dried over anhydrous magnesium sulfate and concentrated under reduced pressure. The residue was purified by silica gel column chromatography (developing solvent: hexane-ethyl acetate=15:1→2:1) to give the title compound as a colorless oil (yield: 660 mg).

$^1$H-NMR (CDCl$_3$) δ: 0.99 (3H, t), 1.50-1.73 (2H, m), 2.74-2.87 (2H, m), 7.08 (1H, t), 7.55 (1H, dd).

Reference Example 31

2-chloro-4-fluoro-3-formylbenzonitrile (compound 36)

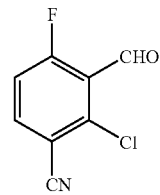

To a solution (300 mL) of diisopropylamine (12.4 mL) in tetrahydrofuran was added dropwise 1.6 mol/L solution (55.4 mL) of n-butyllithium in hexane at −78° C., and the mixture was stirred at 0° C. for 1 hr. To the prepared lithium diisopropylamide was added dropwise a solution (70 mL) of 2-chloro-4-fluorobenzonitrile (12.0 g) in tetrahydrofuran at −78° C. After the reaction mixture was stirred at the same temperature for 1 hr, N,N-dimethylformamide (6.90 mL) was added thereto. The reaction mixture was stirred for 30 min, and acetic acid (20 mL) was added thereto. The temperature of the mixture was raised to room temperature, saturated brine was added to the mixture and the mixture was extracted with ethyl acetate. The extract was dried over magnesium sulfate and concentrated under reduced pressure. The obtained residue was purified by silica gel column chromatography (developing solvent: hexane-ethyl acetate=30:1→1:1) and recrystallized from a mixed solvent of isopropyl ether and hexane to give the title compound as a yellow solid (yield: 5.94 g).

$^1$H-NMR (CDCl$_3$) δ: 7.20-7.35 (1H, m), 7.80-8.00 (1H, m), 10.43 (1H, s).

Reference Example 32

2-chloro-4-fluoroisophthalonitrile (compound 37)

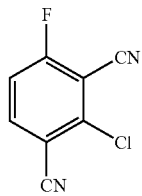 [SMILES: N#Cc1ccc(F)c(C#N)c1Cl]

To a solution of 2-chloro-4-fluoro-3-formylbenzonitrile (597 mg) in 1-methyl-2-pyrrolidone (10 mL) was added hydroxyammonium hydrochloride (310 mg), and the mixture was stirred at 100° C. for 1 hr. The reaction mixture was ice-cooled at 0° C., and thionyl chloride (0.735 mL) was added dropwise thereto. The mixture was stirred at the same temperature for 30 min, water was added to the mixture and the mixture was extracted with ethyl acetate. The extract was washed with saturated brine, dried over anhydrous magnesium sulfate and concentrated under reduced pressure. The residue was recrystallized from hexane to give the title compound as yellow crystals (yield: 503 mg).

$^{1}$H-NMR (CDCl$_{3}$) δ: 7.33 (1H, dd), 7.93 (1H, dd).

Reference Example 33

2,4,5-trifluoro-3-methoxybenzamide (compound 38)

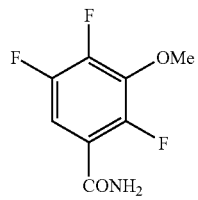 [SMILES: COc1c(F)c(F)cc(C(N)=O)c1F]

Using 2,4,5-trifluoro-3-hydroxybenzoic acid (1.79 g), the title compound was obtained as a yellow oil (yield: 415 mg) by an operation similar to that in Reference Example 19.

$^{1}$H-NMR (CDCl$_{3}$) δ: 4.07 (3H, s), 5.70-6.10 (1H, m), 6.30-6.80 (1H, m), 7.55-7.75 (1H, m).

Reference Example 34

2,4,5-trifluoro-3-methoxybenzonitrile (compound 39)

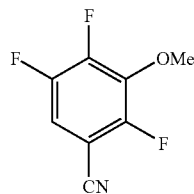 [SMILES: COc1c(F)c(F)cc(C#N)c1F]

Using 2,4,5-trifluoro-3-methoxybenzamide (571 mg), the title compound was obtained as a yellow solid (yield: 347 mg) by an operation similar to that in Reference Example 6.

$^{1}$H-NMR (CDCl$_{3}$) δ: 4.11 (3H, s), 6.95-7.20 (1H, m).

Reference Example 35

2,3-dichloro-4-fluorobenzamide (compound 40)

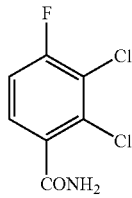

Using 2,3-dichloro-4-fluorobenzoic acid (2.03 g), the title compound was obtained as a colorless solid (yield: 1.35 g) by an operation similar to that in Reference Example 19.

$^{1}$H-NMR (CDCl$_{3}$) δ: 5.94 (1H, br s), 6.18 (1H, br s), 7.18 (1H, dd), 7.67 (1H, dd).

Reference Example 36

2,3-dichloro-4-fluorobenzonitrile (compound 41)

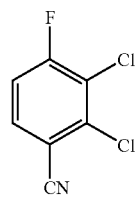 [SMILES: N#Cc1ccc(F)c(Cl)c1Cl]

Using 2,3-dichloro-4-fluorobenzamide (1.23 g), the title compound was obtained as a colorless solid (yield: 1.044 g) by an operation similar to that in Reference Example 6.

$^{1}$H-NMR (CDCl$_{3}$) δ: 7.10-7.30 (1H, m), 7.62 (1H, dd).

Reference Example 37

4-fluoro-5-formyl-2-(trifluoromethyl)benzonitrile (compound 42)

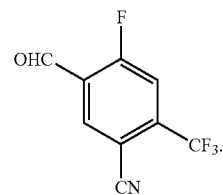 [SMILES: N#Cc1cc(C=O)c(F)cc1C(F)(F)F]

To a solution (75 mL) of diisopropylamine (3.89 mL) in tetrahydrofuran was added dropwise 1.6 mol/L solution (17.30 mL) of n-butyllithium in hexane at 0° C., and the mixture was stirred for 30 min. To the prepared lithium diisopropylamide was added dropwise a solution (25 mL) of 4-fluoro-2-(trifluoromethyl)benzonitrile (3.00 g) in tetrahydrofuran at −78° C., and the mixture was stirred at the same temperature for 20 min. N,N-Dimethylformamide (2.14 mL) was added thereto. The reaction mixture was stirred for 15 min, and acetic acid (4 mL) was added thereto. After the temperature of the reaction mixture was raised to room temperature, saturated brine was added to the mixture and the mixture was extracted with ethyl acetate. The extract was washed with 1 mol/L hydrochloric acid and saturated brine, dried over anhydrous magnesium sulfate and concentrated under reduced pressure. The residue was purified by silica gel column chromatography (developing solvent: hexane-ethyl acetate=15:1→1:1) to give a mixture (2.30 g) of the title compound and 4-fluoro-3-formyl-2-(trifluoromethyl)benzonitrile (3:1) as a yellow oil.

$^{1}$H-NMR (CDCl$_{3}$) δ: 7.70 (1H, d), 8.37 (1H, d), 10.39 (1H, s).

Reference Example 38

4-fluoro-5-(hydroxymethyl)-2-(trifluoromethyl)benzonitrile (compound 43)

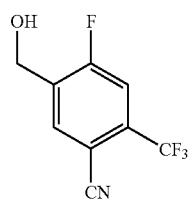 [SMILES: N#Cc1cc(CO)c(F)cc1C(F)(F)F]

To a solution (15 mL) of a mixture (1.01 g) of 4-fluoro-5-formyl-2-(trifluoromethyl)benzonitrile and 4-fluoro-3-formyl-2-(trifluoromethyl)benzonitrile (3:1) in tetrahydrofuran was added sodium borohydride (400 mg) at 0° C., and the mixture was stirred at room temperature for 12 hr. Saturated brine was added to the reaction mixture, and the mixture was extracted with ethyl acetate, dried over anhydrous magnesium sulfate and concentrated under reduced pressure. The residue was purified by silica gel column chromatography (developing solvent: hexane-ethyl acetate=5:1→1:4) to give the title compound as a yellow oil (yield: 456 mg).

$^1$H-NMR (CDCl$_3$) δ: 2.10-3.60 (1H, m), 4.80-5.00 (2H, m), 7.48 (1H, d), 8.08 (1H, d).

Reference Example 39

4-fluoro-5-methyl-2-(trifluoromethyl)benzonitrile (compound 44)

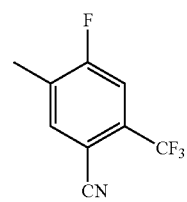

To a solution (10 mL) of 4-fluoro-5-(hydroxymethyl)-2-(trifluoromethyl)benzonitrile (545 mg) and triethylamine (0.862 mL) in tetrahydrofuran was added dropwise methanesulfonyl chloride (0.289 mL) at 0° C. After the dropwise addition, the mixture was stirred at room temperature for 1.5 hr, water was added to the mixture and the mixture was extracted with ethyl acetate. The extract was dried over anhydrous magnesium sulfate and concentrated under reduced pressure. The residue was dissolved in tetrahydrofuran (20 mL) and sodium borohydride (400 mg) was added thereto. The reaction mixture was stirred for 1.5 hr and methanol (2.5 mL) was added thereto. The mixture was stirred for 30 min, and saturated aqueous sodium hydrogencarbonate was added thereto. The mixture was extracted with ethyl acetate, and the extract was dried over anhydrous magnesium sulfate and concentrated under reduced pressure. The residue was purified by silica gel column chromatography (developing solvent: hexane-ethyl acetate=15:1→1:1) to give the title compound as a yellow oil (yield: 89 mg).

$^1$H-NMR (CDCl$_3$) δ: 2.39 (3H, br s), 7.44 (1H, d), 7.70 (1H, d).

Reference Example 40

2-chloro-4,5-difluorobenzonitrile (compound 45)

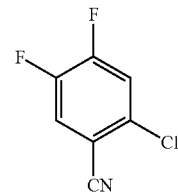

To a solution (20 mL) of 2-chloro-4,5-difluorobenzoic acid (1.0 g) in N,N-dimethylformamide were added N-[3-(dimethylamino)propyl]-N'-ethylcarbodiimide hydrochloride (1.15 g) and N-hydroxysuccinimide (717 mg) under ice-cooling, and the mixture was stirred at room temperature for 1 hr. To the reaction mixture was added 28% aqueous ammonia solution (2 mL) under ice-cooling, and the mixture was stirred at room temperature for 30 min. Water was added to the mixture and the mixture was extracted with ethyl acetate. The extract was washed with saturated brine, dried over anhydrous sodium sulfate and concentrated under reduced pressure to give 2-chloro-4,5-difluorobenzamide as a colorless solid (yield: 760 mg, yield: 76%). To a solution (5 mL) of 2-chloro-4,5-difluorobenzamide (300 mg) in N,N-dimethylformamide was added pyridine (0.253 mL), and oxalyl chloride (0.20 mL) was added dropwise thereto under ice-cooling. The reaction mixture was stirred at room temperature for 30 min, water was added to the mixture and the mixture was extracted with ethyl acetate. The extract was washed with saturated brine, dried over anhydrous sodium sulfate and concentrated under reduced pressure to give the title compound as a colorless solid (yield: 250 mg).

$^1$H-NMR (CDCl$_3$) δ: 7.38 (1H, dd), 7.53 (1H, dd).

Reference Example 41

2-chloro-4-fluoro-3-(hydroxymethyl)benzonitrile (compound 46)

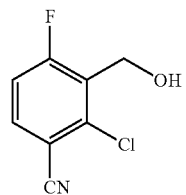 [SMILES: N#Cc1ccc(F)c(CO)c1Cl]

To a solution (10 mL) of 2-chloro-4-fluoro-3-formylbenzonitrile (600 mg) in methanol was added sodium borohydride (136 mg) under ice-cooling, and the mixture was stirred at room temperature for 30 min. Water was added to the reaction mixture, and the mixture was extracted with ethyl acetate. The extract was washed with saturated brine, dried over anhydrous sodium sulfate and concentrated under reduced pressure. The residue was crystallized from hexane-isopropyl ether to give the title compound as a pale-yellow solid (yield: 410 mg).

$^1$H-NMR (CDCl$_3$) δ: 2.05 (1H, t), 4.89 (2H, d), 7.16 (1H, t), 7.67 (1H, dd).

Reference Example 42 ethyl (3S,4S)-4-{[(benzyloxy)carbonyl]amino}-3-hydroxy-5-methylhexanoate (compound 47)

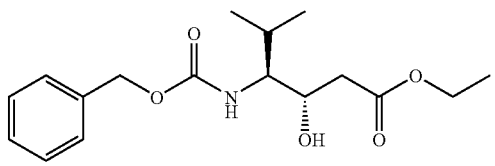 [SMILES: CCOC(=O)C[C@H](O)[C@@H](NC(=O)OCc1ccccc1)C(C)C]

To a solution (40 mL) of diisopropylamine (4.6 mL) in tetrahydrofuran was added 1.6 mol/L solution (20.19 mL) of n-butyllithium in hexane, and the mixture was cooled to −78° C. A solution (5 mL) of ethyl acetate (3.16 mL) in tetrahydrofuran was added dropwise to the mixture at a rate to maintain the reaction mixture at −70° C. or below. After the completion of the dropwise addition, the mixture was stirred at −78° C. for 1 hr, a solution (10 mL) of benzyl [(1S)-1-formyl-2-methylpropyl]carbamate (1.9 g) in tetrahydrofuran was added dropwise thereto at a rate to maintain the reaction mixture at −70° C. or below. The reaction mixture was once warmed to −30° C., and cooled again to −78° C. Acetic acid (2.3 mL) was added to the mixture, and the temperature of the mixture was raised to room temperature. Water was added to the reaction mixture, and the mixture was extracted with ethyl acetate. The extract was washed with saturated brine, dried over anhydrous sodium sulfate and concentrated under reduced pressure. The residue was purified by silica gel column chromatography (developing solvent: hexane:ethyl acetate=9:1→2:1) to give the title compound (yield: 800 mg) and ethyl (3R,4S)-4-{([(benzyloxy)carbonyl]amino}-3-hydroxy-5-methylhexanoate (yield: 550 mg) both as a colorless oil.

$^1$H-NMR (CDCl$_3$) δ: 0.90-1.05 (6H, m), 1.27 (3H, t), 1.80-2.00 (1H, m), 2.45 (1H, dd), 2.55 (1H, dd), 3.10-3.28 (2H, m), 4.16 (2H, q), 4.26 (1H, d), 5.08 (1H, d), 5.13 (1H, d), 7.30-7.40 (5H, m).

$^1$H-NMR data of ethyl (3R,4S)-4-{[(benzyloxy)carbonyl]amino}-3-hydroxy-5-methylhexanoate $^1$H-NMR (CDCl$_3$) δ: 0.8 (3H, d), 0.95 (3H, d), 1.27 (3H, t), 2.10-2.22 (1H, m), 2.47 (1H, dd), 2.60 (1H, dd), 3.25 (1H, d), 3.50-3.63 (1H, m), 3.90-4.00 (1H, m), 4.16 (2H, q), 4.68 (1H, d), 5.10 (2H, s), 7.30-7.40 (5H, m).

Reference Example 43 benzyl (2S,3S)-3-{[tert-butyl(dimethyl)silyl]oxy}-2-isopropylpyrrolidine-1-carboxylate (compound 48)

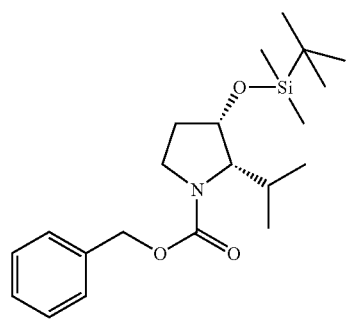 [SMILES: CC(C)[C@H]1[C@@H](O[Si](C)(C)C(C)(C)C)CCN1C(=O)OCc1ccccc1]

To a solution (10 mL) of ethyl (3S,4S)-4-{[(benzyloxy)carbonyl]amino}-3-hydroxy-5-methylhexanoate (700 mg) in tetrahydrofuran were added 2,6-lutidine (0.504 mL) and tert-butyldimethylsilane trifluoromethanesulfonate (0.596 mL), and the mixture was stirred at room temperature for 30 min. Water was added to the reaction mixture and the mixture was extracted with ethyl acetate. The extract was washed with 1 mol/L hydrochloric acid, saturated aqueous sodium hydrogencarbonate solution and saturated brine, dried over anhydrous sodium sulfate and concentrated under reduced pressure. To a solution of the residue in tetrahydrofuran (5 mL)-ethanol (1 mL) was added lithium borohydride (94 mg), and the mixture was stirred at room temperature for 1 hr. Water was added to the reaction mixture and the mixture was extracted with ethyl acetate. The extract was washed with saturated brine, dried over anhydrous sodium sulfate and concentrated under reduced pressure. To a solution (10 mL) of the residue in tetrahydrofuran were added triethylamine (0.602 mL) and methanesulfonyl chloride (0.25 mL), and the mixture was stirred at room temperature for 1 hr. Water was added to the reaction mixture and the mixture was extracted with ethyl acetate. The extract was washed with 1 mol/L hydrochloric acid, saturated aqueous sodium hydrogencarbonate solution and saturated brine, dried over anhydrous sodium sulfate and concentrated under reduced pressure. The residue was dissolved in tetrahydrofuran (10 mL), potassium tert-butoxide (363 mg) was added thereto under ice-cooling, and the mixture was stirred at room temperature for 18 hr. Water was added to the reaction mixture, and the mixture was extracted with ethyl acetate. The extract was washed with 0.1 mol/L hydrochloric acid, saturated aqueous sodium hydrogencarbonate solution and saturated brine, dried over anhydrous sodium sulfate and concentrated under reduced pressure. The residue was purified by silica gel column chromatography (developing solvent: hexane:ethyl acetate=9:1→5:1) to give the title compound (yield: 441 mg) as a pale-yellow oil.

$^1$H-NMR (CDCl$_3$) δ: 0.07 (6H, s), 0.89 (9H, s), 0.80-1.10 (6H, m), 1.80-2.20 (3H, m), 3.30-3.50 (2H, m), 3.65-3.80 (1H, m), 4.26-4.36 (1H, m), 5.08 (1H, d), 5.14 (1H, d), 7.30-7.40 (5H, m).

Reference Example 44 benzyl (2S,3R)-3-{[tert-butyl(dimethyl)silyl]oxy}-2-isopropylpyrrolidine-1-carboxylate (compound 49)

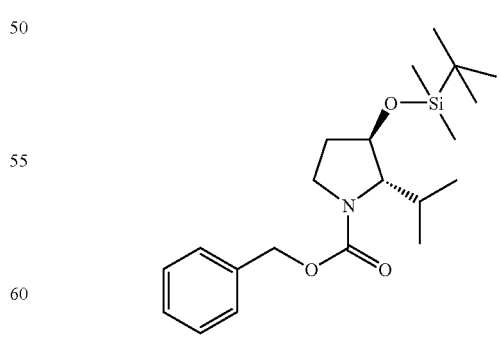

Using ethyl (3R,4S)-4-{[(benzyloxy)carbonyl]amino}-3-hydroxy-5-methylhexanoate (500 mg), the title compound (colorless oil, yield: 412 mg) was synthesized by a method similar to that in Reference Example 43.

$^1$H-NMR (CDCl$_3$) δ: 0.05 (6H, s), 0.80-1.00 (15H, m), 1.60-2.00 (3H, m), 3.35-3.48 (1H, m), 3.50-3.76 (2H, m), 4.14-4.22 (1H, m), 5.10-5.20 (2H, m), 7.30-7.40 (5H, m).

Reference Example 45 benzyl((1S)-2-{[tert-butyl(dimethyl)silyl]oxy}-1-methylpent-4-en-1-yl)carbamate (compound 50)

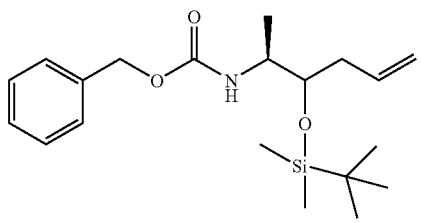 [SMILES: C=CCC(O[Si](C)(C)C(C)(C)C)[C@H](C)NC(=O)OCc1ccccc1]

To a solution (30 mL) of benzyl [(1S)-1-methyl-2-oxoethyl]carbamate (3.0 g) in tetrahydrofuran was added 1.0 mol/L solution (28.8 mL) of allylmagnesium bromide in tetrahydrofuran under ice-cooling, and the mixture was stirred at room temperature for 18 hr. Water was added to the reaction mixture and the mixture was extracted with ethyl acetate. The extract was washed with saturated brine, dried over anhydrous sodium sulfate and concentrated under reduced pressure. The residue was purified by silica gel column chromatography (developing solvent: hexane:ethyl acetate=9:1→1:1) to give benzyl [(1S)-2-hydroxy-1-methylpent-4-en-1-yl]carbamate as a colorless oil. To a solution (10 mL) of the obtained benzyl [(1S)-2-hydroxy-1-methylpent-4-en-1-yl]carbamate in tetrahydrofuran were added 2,6-lutidine (0.629 mL) and tert-butyldimethylsilane trifluoromethanesulfonate (0.91 mL) and the mixture was stirred at room temperature for 30 min. Water was added to the reaction mixture and the mixture was extracted with ethyl acetate. The extract was washed with 1 mol/L hydrochloric acid, saturated aqueous sodium hydrogencarbonate solution and saturated brine, dried over anhydrous sodium sulfate and concentrated under reduced pressure. The residue was purified by silica gel column chromatography (developing solvent: hexane:ethyl acetate=9:1→2:1) to give the title compound as a colorless oil (yield: 610 mg).

$^1$H-NMR (CDCl$_3$) δ: 0.01-0.20 (6H, m), 0.80-1.20 (12H, m), 2.10-2.40 (2H, m), 3.50-3.90 (2H, m), 4.75-5.20 (5H, m), 5.60-5.90 (1H, m), 7.20-7.40 (5H, m).

Reference Example 46 benzyl((1S)-2-{[tert-butyl(dimethyl)silyl]oxy}-5-hydroxy-1-methylpentyl)carbamate (compound 51)

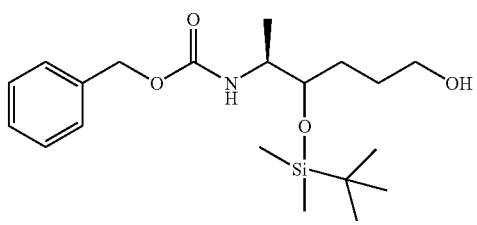 [SMILES: C[C@H](NC(=O)OCc1ccccc1)C(CCCO)O[Si](C)(C)C(C)(C)C]

To a solution (10 mL) of benzyl((1S)-2-{[tert-butyl(dimethyl)silyl]oxy}-1-methylpent-4-en-1-yl)carbamate (600 mg) in tetrahydrofuran was added 0.5 mol/L solution (13.2 mL) of 9-BBN in tetrahydrofuran under ice-cooling, and the mixture was stirred at room temperature for 18 hr. To the reaction mixture were added 1 mol/L aqueous sodium hydroxide solution (12 mL) and 30% aqueous hydrogen peroxide (5 mL), and the mixture was stirred at room temperature for 6 hr. Water was added to the reaction mixture, and the mixture was extracted with ethyl acetate. The extract was washed with saturated brine, dried over anhydrous sodium sulfate and concentrated under reduced pressure. The residue was purified by silica gel column chromatography (developing solvent: hexane:ethyl acetate=9:1→1:1) to give the title compound as a colorless oil (yield: 436 mg).

$^1$H-NMR (CDCl$_3$) δ: 0.02-0.10 (6H, m), 0.89 (9H, s), 1.05-1.20 (3H, m), 1.40-1.75 (5H, m), 3.50-3.90 (4H, m), 4.70-4.95 (1H, m), 5.00-5.20 (2H, m), 7.30-7.40 (5H, m).

Reference Example 47 benzyl (2S)-3-{[tert-butyl(dimethyl)silyl]oxy}-2-methylpiperidine-1-carboxylate (compound 52)

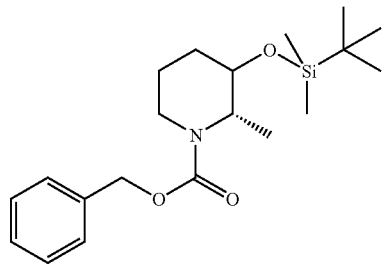 [SMILES: C[C@H]1C(O[Si](C)(C)C(C)(C)C)CCCN1C(=O)OCc1ccccc1]

To a solution (15 mL) of benzyl((1S)-2-{[tert-butyl(dimethyl)silyl]oxy}-5-hydroxy-1-methylpentyl)carbamate (430 mg) in tetrahydrofuran were added triethylamine (0.235 mL) and methanesulfonyl chloride (0.105 mL) under ice-cooling, and the mixture was stirred at room temperature for 30 hr. Water was added to the reaction mixture, and the mixture was extracted with ethyl acetate. The extract was washed with saturated brine, dried over anhydrous sodium sulfate and concentrated under reduced pressure. The residue was dissolved in tetrahydrofuran (20 mL). Potassium tert-butoxide (152 mg) was added under ice-cooling, and the mixture was stirred at room temperature for 1 hr. Water was added to the reaction mixture, and the mixture was extracted with ethyl acetate. The extract was washed with 0.1N hydrochloric acid, saturated aqueous sodium hydrogencarbonate solution and saturated brine, dried over anhydrous sodium sulfate and concentrated under reduced pressure. The residue was purified by silica gel column chromatography (developing solvent: hexane:ethyl acetate=9:1→2:1) to give the title compound (yield: 260 mg) as a colorless oil.

$^1$H-NMR (CDCl$_3$) δ: 0.01-0.06 (6H, m), 0.80-0.90 (9H, m), 1.05-1.15 (3H, m), 1.30-1.80 (4H, m), 2.70-2.95 (1H, m), 3.60-4.50 (3H, m), 5.05-5.20 (2H, m), 7.25-7.40 (5H, m).

Example 3

2-chloro-3-fluoro-4-[(2S,3S)-3-(1-hydroxy-1-methylethyl)-2-methylpyrrolidin-1-yl]benzonitrile (compound 53)

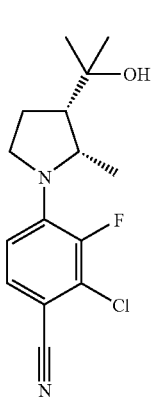

A mixture of (2S,3S)-3-(1-hydroxy-1-methylethyl)-2-methylpyrrolidine 1/2 oxalate (639 mg), 2-chloro-3,4-difluorobenzonitrile (491 mg), lithium carbonate (669 mg) and dimethyl sulfoxide (13 mL) was stirred at 90° C. for 1 hr. The reaction mixture was cooled and partitioned between water and ethyl acetate. The organic layer was washed with water, dried over anhydrous sodium sulfate and concentrated. The obtained residue was purified by silica gel column chromatography (developing solvent: ethyl acetate-hexane). The obtained solid was recrystallized from ethyl acetate to give the title compound as crystals (yield: 538 mg).

$^1$H-NMR (CDCl$_3$) δ: 1.20 (1H, s), 1.20 (3H, d), 1.33 (3H, s), 1.38 (3H, s), 2.00-2.23 (3H, m), 3.40-3.50 (1H, m), 3.60-3.67 (1H, m), 4.35-4.44 (1H, m), 6.43-6.48 (1H, m), 7.23 (1H, dd).

mp: 125-126° C.

Example 4

2-chloro-4-[(2S,3S)-3-(1-hydroxy-1-methylethyl)-2-methylpyrrolidin-1-yl]-5-methylbenzonitrile (compound 54)

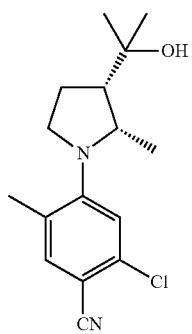 [SMILES: Cc1cc(C#N)c(Cl)cc1N1CC[C@H](C(C)(C)O)[C@@H]1C]

Using 2-chloro-4-fluoro-5-methylbenzonitrile (848 mg), (2S,3S)-3-(1-hydroxy-1-methylethyl)-2-methylpyrrolidine 1/2 oxalate (1.04 g) and lithium carbonate (784 mg, 10.6 mmol), the title compound was obtained as a colorless solid (yield: 590 mg) by an operation similar to that in Example 3.

$^1$H-NMR (CDCl$_3$) δ: 1.02 (3H, d), 1.20 (1H, s), 1.31 (3H, s), 1.37 (3H, s), 2.01-2.18 (2H, m), 2.26-2.35 (1H, m), 2.31 (3H, s), 3.25-3.34 (1H, m), 3.59-3.67 (1H, m), 4.26-4.35 (1H, m), 6.69% (1H, s), 7.25 (1H, s).

IR(KBr): 2973, 2218, 1595, 1503, 1481, 1352 cm$^{-1}$.

Example 5

2-chloro-4-[(2S,3S)-3-hydroxy-2-methylpyrrolidin-1-yl]-5-methylbenzonitrile (compound 55)

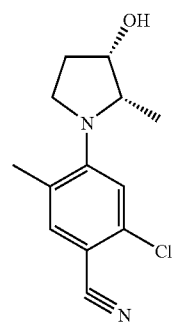 [SMILES: Cc1cc(C#N)c(Cl)cc1N1CC[C@H](O)[C@@H]1C]

To a suspension (418 mL) of (4S,5S)-4-hydroxy-5-methylpyrrolidin-2-one (10.45 g) in dry tetrahydrofuran was added dropwise Red-Al (104.9 g: 363 mmol: 70% toluene solution) under ice-cooling and a nitrogen stream. The mixture was stirred at room temperature for 20 min and further refluxed for 3 hr. The reaction mixture was ice-cooled again and sodium carbonate decahydrate (41.6 g) was added thereto under a nitrogen stream. After the reaction mixture was stirred at room temperature overnight, the insoluble material was filtered off with celite, and washed with tetrahydrofuran. The filtrate and the wash were combined and concentrated under reduced pressure to give (2S,3S)-3-hydroxy-2-methylpyrrolidine. The present compound was diluted with dimethyl sulfoxide without further purification to give 0.9M-dimethyl sulfoxide solution, which was used in the next step.

To a solution (25 mL) of 2-chloro-4-fluoro-5-methylbenzonitrile (848 mg) in dimethyl sulfoxide were added 0.9M-dimethyl sulfoxide solution (5.56 mL) of (2S,3S)-3-hydroxy-2-methylpyrrolidine and lithium carbonate (370 mg), and the mixture was stirred at 100° C. for 1 hr. Water was added and the mixture was extracted with ethyl acetate. The extract was washed with saturated brine, dried over anhydrous sodium sulfate and concentrated under reduced pressure. The residue was purified by silica gel column chromatography (developing solvent: hexane-ethyl acetate) and crystallized from ethyl acetate-hexane to give the title compound as a colorless solid (yield: 374 mg).

$^1$H-NMR (CDCl$_3$) δ: 1.14 (3H, d), 1.69 (1H, d), 1.98-2.08 (2H, m), 2.26 (3H, s), 3.00-3.07 (1H, m), 3.78-3.85 (1H, m), 3.88-3.97 (1H, m), 4.38-4.43 (1H, m), 6.81 (1H, s), 7.33 (1H, s).

IR(KBr): 3428, 2975, 2220, 1595, 1537, 1501, 1478, 1397 cm$^{-1}$.

Example 6

2-chloro-3-ethyl-4-[(2S,3S)-3-hydroxy-2-methylpyrrolidin-1-yl]benzonitrile (compound 56)

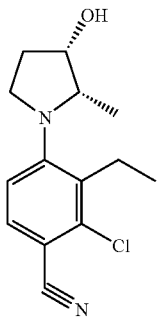 [SMILES: CCc1c(N2CC[C@H](O)[C@@H]2C)ccc(C#N)c1Cl]

Using 2-chloro-4-fluoro-3-ethylbenzonitrile (1.01 g), (2S,3S)-3-hydroxy-2-methylpyrrolidine (8.25 mmol) and lithium carbonate (813 mg), the title compound was obtained as a colorless solid (yield: 147 mg) by an operation similar to that in Example 3.

$^1$H-NMR (CDCl$_3$) δ: 1.09 (3H, d), 1.21 (3H, t), 1.68 (1H, d), 1.97-2.17 (2H, m), 2.73-2.85 (1H, m), 2.89-2.98 (2H, m), 3.64-3.72 (1H, m), 3.81-3.89 (1H, m), 4.32-4.37 (1H, m), 6.88 (1H, d), 7.42 (1H, d).

IR(KBr): 3443, 2975, 2222, 1584, 1468, 1312 cm$^{-1}$.

Example 7

2-chloro-3-ethyl-4-[(2S,3S)-3-(1-hydroxy-1-methylethyl)-2-methylpyrrolidin-1-yl]benzonitrile (compound 57)

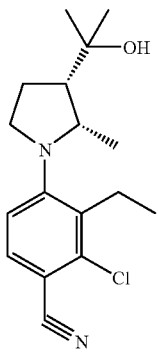 [SMILES: CCc1c(N2CC[C@H](C(C)(C)O)[C@@H]2C)ccc(C#N)c1Cl]

Using 2-chloro-4-fluoro-3-ethylbenzonitrile (1.10 g), (2S,3S)-3-(1-hydroxy-1-methylethyl)-2-methylpyrrolidine 1/2 oxalate (1.24 g) and lithium carbonate (930 mg), the title compound was obtained as a colorless solid (yield: 255 mg) by an operation similar to that in Example 3.

$^1$H-NMR (CDCl$_3$) δ: 1.03 (3H, d), 1.24 (3H, t), 1.31 (3H, s), 1.37 (3H, s), 1.58 (1H, s), 2.04-2.13 (2H, m), 2.31-2.40 (1H, m), 2.81 (2H, q), 3.06-3.14 (1H, m), 3.57-3.65 (1H, m), 4.03-4.12 (1H, m), 6.81 (1H, d), 7.39 (1H, d).

IR(KBr): 3474, 2973, 2220, 1584, 1470 cm$^{-1}$.

Example 8

4-[(2S,3S)-3-(1-hydroxy-1-methylethyl)-2-methylpyrrolidin-1-yl]-2-(trifluoromethyl)benzonitrile (compound 58)

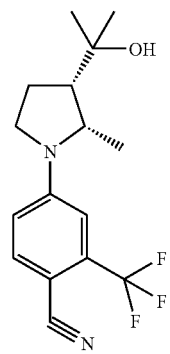 [SMILES: C[C@H]1[C@@H](C(C)(C)O)CCN1c1ccc(C#N)c(C(F)(F)F)c1]

Using 4-fluoro-2-(trifluoromethyl)benzonitrile (946 mg), (2S,3S)-3-(1-hydroxy-1-methylethyl)-2-methylpyrrolidine 1/2 oxalate (1.04 g) and lithium carbonate (784 mg), the title compound was obtained as a colorless solid (yield: 1.28 g) by an operation similar to that in Example 3.

$^1$H-NMR (CDCl$_3$) δ: 1.22 (3H, d), 1.22 (1H, s), 1.34 (3H, s), 1.40 (3H, s), 2.09-2.27 (3H, m), 3.25-3.34 (1H, m), 3.45-3.51 (1H, m), 4.03-4.15 (1H, m), 6.60 (1H, dd), 6.75 (1H, d), 7.55 (1H, d).

IR(KBr): 3466, 2976, 2218, 1613, 1522, 1462, 1400 cm$^{-1}$.

Example 9

4-[(2S,3S)-3-hydroxy-2-methylpyrrolidin-1-yl]-2-(trifluoromethyl)benzonitrile (compound 59)

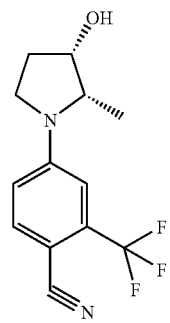 [SMILES: C[C@H]1[C@@H](O)CCN1c1ccc(C#N)c(C(F)(F)F)c1]

Using 4-fluoro-2-(trifluoromethyl)benzonitrile (851 mg), (2S,3S)-3-hydroxy-2-methylpyrrolidine (5 mmol) and lithium carbonate (665 mg), the title compound was obtained as a colorless solid (yield: 630 mg) by an operation similar to that in Example 3.

$^1$H-NMR (CDCl$_3$) δ: 1.20 (3H, d), 1.85 (1H, d), 2.04-2.17 (1H, m), 2.27-2.37 (1H, m), 3.24-3.33 (1H, m), 3.49-3.56 (1H, m), 3.94-4.02 (1H, m), 4.45-4.54 (1H, m), 6.64 (1H, dd), 6.79 (1H, d), 7.56 (1H, d).

IR(KBr): 3422, 2978, 2218, 1615, 1522, 1462, 1397 cm$^{-1}$.

Example 10

2-fluoro-4-[(2S,3S)-3-(1-hydroxy-1-methylethyl)-2-methylpyrrolidin-1-yl]benzonitrile (compound 60)

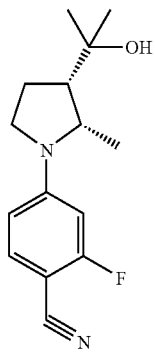 [SMILES: C[C@H]1[C@@H](C(C)(C)O)CCN1c1ccc(C#N)c(F)c1]

Using 2,4-difluorobenzonitrile (696 mg), (2S,3S)-3-(1-hydroxy-1-methylethyl)-2-methylpyrrolidine 1/2 oxalate (1.04 g) and lithium carbonate (784 mg), the title compound was obtained as a colorless solid (yield: 838 mg) by an operation similar to that in Example 3.

$^1$H-NMR (CDCl$_3$) δ: 1.21 (3H, d), 1.23 (1H, s), 1.33 (3H, s), 1.39 (3H, s), 2.06-2.25 (3H, m), 3.20-3.29 (1H, m), 3.39-3.45 (1H, m), 3.97-4.05 (1H, m), 6.20 (1H, dd), 6.28 (1H, dd), 7.33 (1H, t).

IR(KBr): 2975, 2216, 1624, 1547, 1524, 1464, 1400, 1350 cm$^{-1}$.

Example 11

2,6-difluoro-4-[(2S,3S)-3-(1-hydroxy-1-methylethyl)-2-methylpyrrolidin-1-yl]benzonitrile (compound 61)

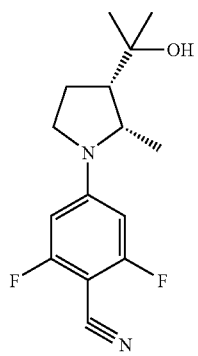 [SMILES: C[C@H]1[C@@H](C(C)(C)O)CCN1c1cc(F)c(C#N)c(F)c1]

Using 2,4,6-trifluorobenzonitrile (786 mg), (2S,3S)-3-(1-hydroxy-1-methylethyl)-2-methylpyrrolidine 1/2 oxalate (1.04 g) and lithium carbonate (784 mg), the title compound was obtained as a colorless solid (yield: 538 mg) by an operation similar to that in Example 3.

$^1$H-NMR (CDCl$_3$) δ: 1.21 (3H, d), 1.24 (1H, s), 1.33 (3H, s), 1.39 (3H, s), 2.08-2.26 (3H, m), 3.20-3.29 (1H, m), 3.38-3.44 (1H, m), 3.94-4.02 (1H, m), 6.05 (2H, d).

IR(KBr): 2976, 2224, 1644, 1549, 1530, 1426, 1354 cm$^{-1}$.

Example 12

2,3,5-trifluoro-4-[(2S,3S)-3-(1-hydroxy-1-methylethyl)-2-methylpyrrolidin-1-yl]benzonitrile (compound 62)

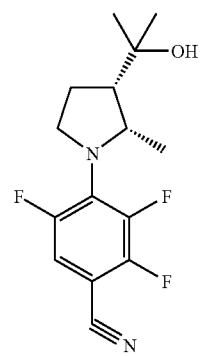 [SMILES: C[C@H]1[C@@H](C(C)(C)O)CCN1c1c(F)cc(C#N)c(F)c1F]

Using 2,3,4,5-tetrafluorobenzonitrile (876 mg), (2S,3S)-3-(1-hydroxy-1-methylethyl)-2-methylpyrrolidine 1/2 oxalate (1.04 g) and lithium carbonate (784 mg), the title compound was obtained as a colorless solid (yield: 922 mg) by an operation similar to that in Example 3.

$^1$H-NMR (CDCl$_3$) δ: 1.18 (3H, d), 1.20 (1H, s), 1.32 (3H, s), 1.37 (3H, s), 1.95-2.20 (3H, m), 3.61-3.73 (1H, m), 4.00-4.09 (1H, m), 4.50-4.57 (1H, m), 6.90-6.97 (1H, m).

IR(KBr): 2976, 2228, 1630, 1510, 1485, 1381 cm$^{-1}$.

Example 13

3,4,6-trifluoro-5-[(2S,3S)-3-(1-hydroxy-1-methylethyl)-2-methylpyrrolidin-1-yl]phthalonitrile (compound 63)

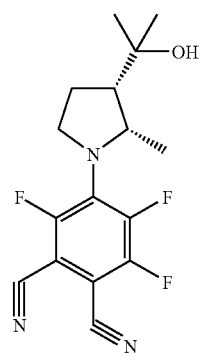 [SMILES: C[C@H]1[C@@H](C(C)(C)O)CCN1c1c(F)c(F)c(C#N)c(C#N)c1F]

Using 3,4,5,6-tetrafluorophthalonitrile (464 mg), (2S,3S)-3-(1-hydroxy-1-methylethyl)-2-methylpyrrolidine 1/2 oxalate (480 mg) and lithium carbonate (362 mg), the title compound was obtained as a pale-yellow solid (yield: 250 mg) by an operation similar to that in Example 3.

$^1$H-NMR (CDCl$_3$) δ: 1.19 (1H, s), 1.22 (3H, d), 1.33 (3H, s), 1.37 (3H, s), 2.00-2.17 (3H, m), 3.70-3.82 (1H, m), 4.03-4.17 (1H, m), 4.54-4.65 (1H, m).

IR(KBr): 2976, 2230, 1605, 1559, 1510, 1480, 1420 cm$^{-1}$.

Example 14

2,3-dichloro-4-[(2S,3S)-3-(1-hydroxy-1-methylethyl)-2-methylpyrrolidin-1-yl]-5-methylbenzonitrile (compound 64)

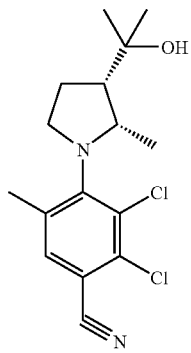 [SMILES: Cc1cc(C#N)c(Cl)c(Cl)c1N1CC[C@H](C(C)(C)O)[C@@H]1C]

Using 2,3-dichloro-4-fluoro-5-methylbenzonitrile (1.02 g), (2S,3S)-3-(1-hydroxy-1-methylethyl)-2-methylpyrrolidine 1/2 oxalate (1.04 g) and lithium carbonate (776 mg), the title compound was obtained as a colorless solid (yield: 68 mg) by an operation similar to that in Example 3.

$^1$H-NMR (CDCl$_3$) δ: 1.04 (3H, d), 1.34 (3H, s), 1.36 (3H, s), 1.99-2.19 (2H, m), 2.30 (3H, s), 2.39-2.47 (1H, m), 2.98-3.06 (1H, m), 3.49-3.55 (1H, m), 3.91-3.99 (1H, m), 7.41 (1H, s).

IR(KBr): 3515, 2971, 2232, 1580, 1435, 1383 cm$^{-1}$.

Example 15

2,3-dichloro-4-[(2S,3S)-3-hydroxy-2-methylpyrrolidin-1-yl]-5-methylbenzonitrile (compound 65)

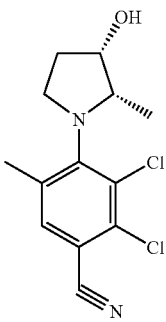 [SMILES: Cc1cc(C#N)c(Cl)c(Cl)c1N1CC[C@H](O)[C@@H]1C]

Using 2,3-dichloro-4-fluoro-5-methylbenzonitrile (1.02 g), 0.9 M-dimethyl sulfoxide solution (5.56 ml) of (2S,3S)-3-hydroxy-2-methylpyrrolidine and lithium carbonate (370 mg), the title compound was obtained as a colorless solid (yield: 53 mg) by an operation similar to that in Example 3.

$^1$H-NMR (CDCl$_3$) δ: 0.90 (3H, d), 1.81 (1H, brs), 2.02-2.10 (1H, m), 2.19-2.29 (1H, m), 2.31 (3H, s), 3.05-3.12 (1H, m), 3.56-3.64 (1H, m), 3.91-4.01 (1H, m), 4.26 (1H, brs), 7.42 (1H, s).

IR(KBr): 3428, 2971, 2930, 2230, 1580, 1460, 1435, 1348 cm$^{-1}$.

Example 16

3,5-difluoro-4-[(2S,3S)-3-(1-hydroxy-1-methylethyl)-2-methylpyrrolidin-1-yl]benzonitrile (compound 66)

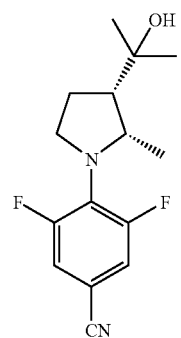

Using 3,4,5-difluorobenzonitrile (353 mg), (2S,3S)-3-(1-hydroxy-1-methylethyl)-2-methylpyrrolidine 1/2 oxalate (479 mg) and lithium carbonate (188 mg), the title compound was obtained as a colorless solid (yield: 28 mg) by an operation similar to that in Example 3.

$^1$H-NMR (CDCl$_3$) δ: 1.14 (3H, d), 1.19 (1H, s), 1.31 (3H, s), 1.37 (3H, s), 1.87-2.27 (3H, m), 3.51-3.70 (1H, m), 3.89-4.13 (1H, m), 4.48 (1H, q), 7.03 (1H, d), 7.06 (1H, d).

IR(KBr): 3524, 2220, 1508, 1366 cm$^{-1}$.

Example 17

4-[(2S,3S)-3-(1-hydroxy-1-methylethyl)-2-methylpyrrolidin-1-yl]-2-methoxybenzonitrile (compound 67)

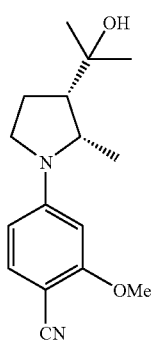 [SMILES: COc1cc(N2CC[C@H](C(C)(C)O)[C@@H]2C)ccc1C#N]

Using 4-fluoro-2-methoxybenzonitrile (352 mg), (2S,3S)-3-(1-hydroxy-1-methylethyl)-2-methylpyrrolidine 1/2 oxalate (470 mg) and lithium carbonate (188 mg), the title compound was obtained as an orange solid (yield: 195 mg) by an operation similar to that in Example 3.

$^1$H-NMR (CDCl$_3$) δ: 1.21 (3H, d), 1.12-1.28 (1H, m), 1.34 (3H, s), 1.40 (3H, s), 2.00-2.30 (3H, m), 3.20-3.38 (1H, m), 3.38-3.57 (1H, m), 3.89 (3H, s), 4.00-4.18 (1H, m), 5.94 (1H, d), 6.11 (1H, dd), 7.32 (1H, dd).

IR(KBr): 3495, 2201, 1605, 1244 cm$^{-1}$.

Example 18

2,5-difluoro-4-[(2S,3S)-3-(1-hydroxy-1-methylethyl)-2-methylpyrrolidin-1-yl]benzonitrile (compound 68)

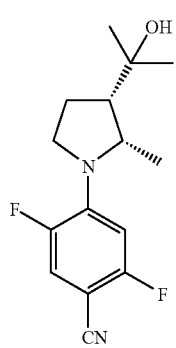

Using 2,4,5-trifluorobenzonitrile (153 mg), (2S,3S)-3-(1-hydroxy-1-methylethyl)-2-methylpyrrolidine 1/2 oxalate (247 mg) and lithium carbonate (97 mg), the title compound was obtained as white crystals (yield: 183 mg) by an operation similar to that in Example 3.

$^1$H-NMR (CDCl$_3$) δ: 1.07-1.26 (4H, m), 1.33 (3H, s), 1.38 (3H, s), 1.95-2.30 (3H, m), 3.28-3.50 (1H, m), 3.50-3.68 (1H, m), 4.25-4.48 (1H, m), 6.26 (1H, dd), 7.09 (1H, dd).

IR(KBr): 3526, 2220, 1636, 1534 cm$^{-1}$.

Example 19

4-[(2S,3S)-3-(1-hydroxy-1-methylethyl)-2-methylpyrrolidin-1-yl]-3-methoxybenzonitrile (compound 69)

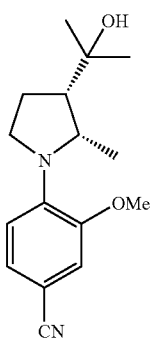 [SMILES: COc1cc(C#N)ccc1N1CC[C@H](C(C)(C)O)[C@@H]1C]

Using 4-fluoro-3-methoxybenzonitrile (232 mg), (2S,3S)-3-(1-hydroxy-1-methylethyl)-2-methylpyrrolidine 1/2 oxalate (390 mg) and lithium carbonate (153 mg), the title compound was obtained as a white solid (yield: 42 mg) by an operation similar to that in Example 3.

$^1$H-NMR (CDCl$_3$) δ: 1.06 (3H, d), 1.21 (1H, br s), 1.31 (3H, s), 1.38 (3H, s), 1.90-2.33 (3H, m), 3.28-3.48 (1H, m), 3.50-3.68 (1H, m), 3.81 (3H, s), 4.71 (1H, q), 6.51 (1H, d), 6.96 (1H, d), 7.16 (1H, dd).

IR(KBr): 3468, 2213, 1514, 1364 cm$^{-1}$.

Example 20

4-[(2S,3S)-3-(1-hydroxy-1-methylethyl)-2-methylpyrrolidin-1-yl]phthalonitrile (compound 70)

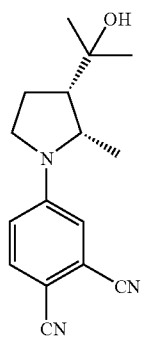 [SMILES: C[C@H]1[C@@H](C(C)(C)O)CCN1c1ccc(C#N)c(C#N)c1]

Using 4-fluorophthalonitrile (500 mg), (2S,3S)-3-(1-hydroxy-1-methylethyl)-2-methylpyrrolidine 1/2 oxalate (870 mg) and lithium carbonate (341 mg), the title compound was obtained as a yellow solid (yield: 42 mg) by an operation similar to that in Example 3.

$^1$H-NMR (CDCl$_3$) δ: 1.10-1.35 (1H, m), 1.22 (3H, d), 1.35 (3H, s), 1.40 (3H, s), 2.03-2.32 (3H, m), 3.20-3.35 (1H, m), 3.35-3.58 (1H, m), 4.00-4.15 (1H, m), 6.66 (1H, dd), 6.77 (1H, d), 7.50 (1H, d).

IR(KBr): 3501, 2215, 1599 cm$^{-1}$.

Example 21

2-bromo-4-[(2S,3S)-3-(1-hydroxy-1-methylethyl)-2-methylpyrrolidin-1-yl]benzonitrile (compound 71)

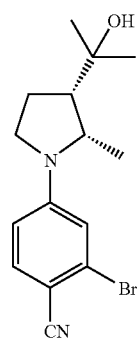 [SMILES: C[C@H]1[C@@H](C(C)(C)O)CCN1c1ccc(C#N)c(Br)c1]

Using 2-bromo-4-fluorobenzonitrile (497 mg), (2S,3S)-3-(1-hydroxy-1-methylethyl)-2-methylpyrrolidine 1/2 oxalate (659 mg) and lithium carbonate (259 mg), the title compound was obtained as a yellow solid (yield: 608 mg) by an operation similar to that in Example 3.

$^1$H-NMR (CDCl$_3$) δ: 1.20 (3H, d), 1.10-1.33 (1H, m), 1.33 (3H, s), 1.39 (3H, s), 2.00-2.28 (3H, m), 3.10-3.35 (1H, m), 3.35-3.50 (1H, m), 3.92-4.13 (1H, m), 6.43 (1H, dd), 6.70 (1H, d), 7.39 (1H, d).

IR(KBr): 3480, 2215, 1599, 1385 cm$^{-1}$.

Example 22

2-chloro-4-[(2S,3S)-3-(1-hydroxy-1-methylethyl)-2-methylpyrrolidin-1-yl]-3-propylbenzonitrile (compound 72)

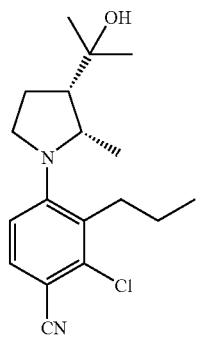 [SMILES: CCCc1c(N2CC[C@H](C(C)(C)O)[C@@H]2C)ccc(C#N)c1Cl]

Using 2-chloro-4-fluoro-3-propylbenzonitrile (538 mg), (2S,3S)-3-(1-hydroxy-1-methylethyl)-2-methylpyrrolidine 1/2 oxalate (615 mg) and lithium carbonate (259 mg), the title compound was obtained as a yellow solid (yield: 69 mg) by an operation similar to that in Example 3.

$^1$H-NMR (CDCl$_3$) δ: 0.90-1.10 (6H, m), 1.20-1.54 (2H, m), 1.32 (3H, s), 1.37 (3H, s), 1.68-1.89 (1H, m), 1.99-2.17 (2H, m), 2.25-2.43 (1H, m), 2.63-2.80 (2H, m), 3.02-3.17 (1H, m), 3.51-3.67 (1H, m), 3.94-4.08 (1H, m), 6.80 (1H, d), 7.38 (1H, d).

IR(KBr): 3480, 2220, 1584, 1470 cm$^{-1}$.

Example 23

2-chloro-4-[(2S,3S)-3-(1-hydroxy-1-methylethyl)-2-methylpyrrolidin-1-yl]isophthalonitrile (compound 73)

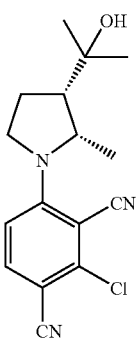 [SMILES: C[C@H]1[C@@H](C(C)(C)O)CCN1c1ccc(C#N)c(Cl)c1C#N]

Using 2-chloro-4-fluoroisophthalonitrile (503 mg), (2S,3S)-3-(1-hydroxy-1-methylethyl)-2-methylpyrrolidine 1/2 oxalate (629 mg) and lithium carbonate (259 mg), the title compound was obtained as a pale-yellow solid (yield: 540 mg) by an operation similar to that in Example 3.

$^1$H-NMR (CDCl$_3$) δ: 1.21 (1H, s), 1.28 (3H, d), 1.34 (3H, s), 1.40 (3H, s), 2.08-2.30 (3H, m), 3.60-3.85 (1H, m), 3.85-4.05 (1H, m), 4.60-4.80 (1H, m), 6.56 (1H, d), 7.43 (1H, d).

IR(KBr): 3501, 2224, 1601, 1499 cm$^{-1}$.

Example 24

2,5-difluoro-4-[(2S,3S)-3-(1-hydroxy-1-methylethyl)-2-methylpyrrolidin-1-yl]-3-methoxybenzonitrile (compound 74)

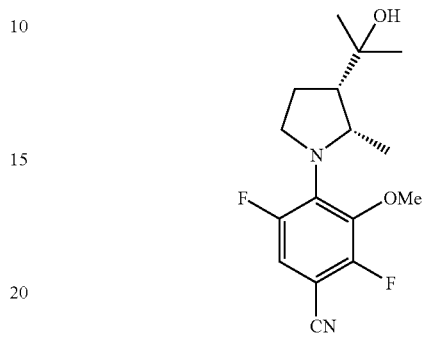

Using 2,4,5-trifluoro-3-methoxybenzonitrile (347 mg), (2S,3S)-3-(1-hydroxy-1-methylethyl)-2-methylpyrrolidine 1/2 oxalate (409 mg) and lithium carbonate (328 mg), the title compound was obtained as a pale-yellow oil (yield: 175 mg) by an operation similar to that in Example 3.

$^1$H-NMR (CDCl$_3$) δ: 1.10 (3H, d), 1.20-1.35 (1H, m), 1.32 (3H, s), 1.37 (3H, s), 1.90-2.30 (3H, m), 3.30-3.55 (1H, m), 3.80 (3H, s), 4.00-4.20 (1H, m), 4.56 (1H, q), 6.93 (1H, dd).

IR(KBr): 3478, 2226, 1617, 1373 cm$^{-1}$.

Example 25

2,3-dichloro-4-[(2S,3S)-3-(1-hydroxy-1-methylethyl)-2-methylpyrrolidin-1-yl]benzonitrile (compound 75)

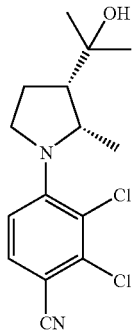 [SMILES: C[C@H]1[C@@H](C(C)(C)O)CCN1c1ccc(C#N)c(Cl)c1Cl]

Using 2,3-dichloro-4-fluorobenzonitrile (334 mg), (2S,3S)-3-(1-hydroxy-1-methylethyl)-2-methylpyrrolidine 1/2 oxalate (397.3 mg) and lithium carbonate (312 mg), the title compound was obtained as white crystals (yield: 427 mg) by an operation similar to that in Example 3.

$^1$H-NMR (CDCl$_3$) δ: 1.08 (3H, d), 1.19 (1H, br s), 1.31 (3H, s), 1.38 (3H, s), 1.95-2.39 (3H, m), 3.33-3.51 (1H, m), 3.69-3.85 (1H, m), 4.88 (1H, q), 6.68 (1H, d), 7.36 (1H, d).

IR(KBr): 3468, 2220, 1586, 1476 cm$^{-1}$.

Example 26

4-[(2S,3S)-3-(1-hydroxy-1-methylethyl)-2-methylpyrrolidin-1-yl]-5-methyl-2-(trifluoromethyl)benzonitrile (compound 76)

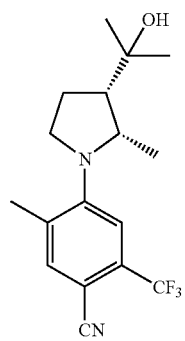 [SMILES: Cc1cc(C#N)c(C(F)(F)F)cc1N1CC[C@H](C(C)(C)O)[C@@H]1C]

Using 4-fluoro-5-methyl-2-(trifluoromethyl)benzonitrile (89 mg), (2S,3S)-3-(1-hydroxy-1-methylethyl)-2-methylpyrrolidine 1/2 oxalate (100 mg) and lithium carbonate (78 mg), the title compound was obtained as a colorless solid (yield: 17 mg) by an operation similar to that in Example 3.

$^1$H-NMR (CDCl$_3$) δ: 1.04 (3H, d), 1.15-1.22 (1H, m), 1.32 (3H, s), 1.38 (3H, s), 1.97-2.22 (2H, m), 2.23-2.49 (1H, m), 2.40 (3H, s), 3.29-3.45 (1H, m), 3.71 (1H, dt), 4.30-4.44 (1H, m), 6.93 (1H, s), 7.41 (1H, s).

IR(KBr): 3445, 2222, 1605, 1132 cm$^{-1}$.

Example 27

2,3-dichloro-4-[(2S,3S)-3-hydroxy-2-methylpyrrolidin-1-yl]benzonitrile (compound 77)

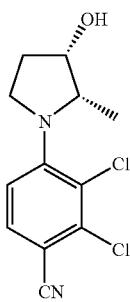 [SMILES: C[C@H]1[C@@H](O)CCN1c1ccc(C#N)c(Cl)c1Cl]

Using 2,3-dichloro-4-fluorobenzonitrile (400.5 mg), 0.9 mol/L solution (2.35 mL) of (2S,3S)-2-methylpyrrolidin-3-ol in dimethyl sulfoxide and lithium carbonate (78 mg), the title compound was obtained as yellow crystals (yield: 417 mg) by an operation similar to that in Example 3.

$^1$H-NMR (CDCl$_3$) δ: 1.15 (3H, d), 1.70 (1H, d), 1.94-2.12 (2H, m), 3.13-3.27 (1H, m), 3.98-4.13 (1H, m), 4.12-4.26 (1H, m), 4.37-4.49 (1H, m), 6.78 (1H, d), 7.41 (1H, d).

IR(KBr): 3493, 2230, 1586, 1470 cm$^{-1}$.

Example 28

4-[(2S,3S)-3-hydroxy-2-methylpyrrolidin-1-yl]-3-(trifluoromethyl)benzonitrile (compound 78)

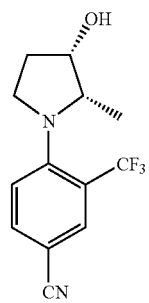 [SMILES: C[C@H]1[C@@H](O)CCN1c1ccc(C#N)cc1C(F)(F)F]

Using 4-fluoro-3-(trifluoromethyl)benzonitrile (398 mg), 0.9 mol/L (2S,3S)-2-methylpyrrolidin-3-ol dimethyl sulfoxide solution (2.35 mL) and lithium carbonate (156 mg), the title compound was obtained as yellow crystals (yield: 135 mg) by an operation similar to that in Example 3.

$^1$H-NMR (CDCl$_3$) δ: 1.18 (3H, d), 1.65-1.81 (1H, m), 1.96-2.12 (2H, m), 3.16-3.32 (1H, m), 3.80-4.02 (2H, m), 4.33-4.46 (1H, m), 7.01 (1H, d), 7.60 (1H, dd), 7.87 (1H, d).

IR(KBr): 3411, 2224, 1613 cm$^{-1}$.

Example 29

2-chloro-5-fluoro-4-[(2S,3S)-3-(1-hydroxy-1-methylethyl)-2-methylpyrrolidin-1-yl]benzonitrile (compound 79)

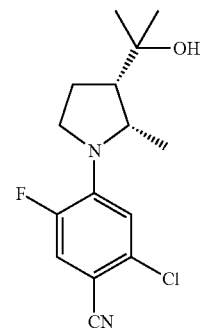 [SMILES: C[C@H]1[C@@H](C(C)(C)O)CCN1c1cc(Cl)c(C#N)cc1F]

Using 2-chloro-4,5-difluorobenzonitrile (240 mg), (2S,3S)-3-(1-hydroxy-1-methylethyl)-2-methylpyrrolidine 1/2 oxalate (390 mg) and lithium carbonate (152 mg), the title compound was obtained as a colorless solid (yield: 200 mg) by an operation similar to that in Example 3.

$^1$H-NMR (CDCl$_3$) δ: 1.19 (3H, d), 1.33 (3H, s), 1.38 (3H, s), 2.00-2.25 (3H, m), 3.35-3.50 (1H, m), 3.56-3.70 (1H, m), 4.30-4.45 (1H, m), 6.55 (1H, d), 7.16 (1H, d).

IR(KBr): 2976, 2218, 1615 cm$^{-1}$.

Example 30

4-[(2S,3S)-3-(1-hydroxy-1-methylethyl)-2-methylpyrrolidin-1-yl]-3-(trifluoromethyl)benzonitrile (compound 80)

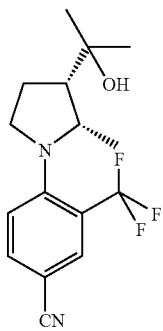 [SMILES: C[C@H]1[C@@H](C(C)(C)O)CCN1c1ccc(C#N)cc1C(F)(F)F]

Using 4-fluoro-3-(trifluoromethyl)benzonitrile (300 mg), (2S,3S)-3-(1-hydroxy-1-methylethyl)-2-methylpyrrolidine 1/2 oxalate (359 mg) and lithium carbonate (140 mg), the title compound was obtained as a colorless solid (yield: 180 mg) by an operation similar to that in Example 3.

$^1$H-NMR (CDCl$_3$) δ: 1.11 (3H, d), 1.21 (1H, s), 1.31 (3H, s), 1.38 (3H, s), 2.00-2.30 (3H, m), 3.30-3.45 (1H, m), 3.65-3.75 (1H, m), 4.35-4.45 (1H, m), 6.86 (1H, d), 7.54 (1H, dd), 7.84 (1H, d).

mp: 98-100° C.

Example 31

2-chloro-3-(hydroxymethyl)-4-[(2S,3S)-3-(1-hydroxy-1-methylethyl)-2-methylpyrrolidin-1-yl]benzonitrile (compound 81)

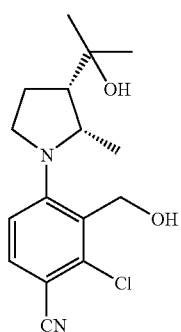 [SMILES: C[C@H]1[C@@H](C(C)(C)O)CCN1c1ccc(C#N)c(Cl)c1CO]

To a solution (2 mL) of 2-chloro-4-fluoro-3-(hydroxymethyl)benzonitrile (150 mg) in dimethyl sulfoxide were added (2S,3S)-3-(1-hydroxy-1-methylethyl)-2-methylpyrrolidine 1/2 oxalate (167 mg) and lithium carbonate (66 mg), and the mixture was stirred at 140° C. for 10 min in a microwave reaction apparatus. Water was added and the mixture was extracted with ethyl acetate. The extract was washed with saturated brine, dried over anhydrous sodium sulfate and concentrated under reduced pressure. The residue was purified by silica gel column chromatography (developing solvent: hexane:ethyl acetate=9:1→1:1) and recrystallized from ethyl acetate-isopropyl ether to give the compound as a pale-yellow solid (yield: 85 mg).

$^1$H-NMR (CDCl$_3$) δ: 1.06 (3H, d), 1.21 (1H, s), 1.31 (3H, s), 1.38 (3H, s), 2.00-2.22 (2H, m), 2.28-2.40 (1H, m), 2.92 (1H, t), 3.20-3.36 (1H, m), 3.62-3.76 (1H, m), 4.24-4.36 (1H, m), 4.48 (2H, d), 6.80 (1H, d), 7.44 (1H, d).

IR(KBr): 2973, 2218, 1590, 1474 cm$^{-1}$.

Example 32

4-[(2S,3S)-3-hydroxy-2-isopropylpyrrolidin-1-yl]-2-(trifluoromethyl)benzonitrile (compound 82)

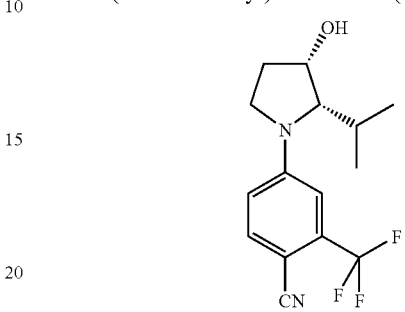

To a solution (10 mL) of benzyl (2S,3S)-3-{[tert-butyl(dimethyl)silyl]oxy}-2-isopropylpyrrolidine-1-carboxylate (440 mg) in methanol was added 10% palladium carbon (50 mg), and the mixture was stirred at room temperature for 18 hr under a hydrogen atmosphere (1 atm). The reaction mixture was filtrated, and the filtrate was concentrated under reduced pressure. The residue was dissolved in dimethyl sulfoxide (3 mL). 4-Fluoro-2-(trifluoromethyl)benzonitrile (265 mg) and lithium carbonate (103 mg) were added to the mixture, and the mixture was stirred at 100° C. for 3 hr. Water was added to the reaction mixture, and the mixture was extracted with ethyl acetate. The extract was washed with saturated brine, dried over anhydrous sodium sulfate and concentrated under reduced pressure. To a solution (10 mL) of the residue in tetrahydrofuran was added 1 mol/L solution (2.5 mL) of tetrabutylammonium fluoride in tetrahydrofuran, and the mixture was stirred at room temperature for 1 hr. Water was added to the reaction mixture, and the mixture was extracted with ethyl acetate. The extract was washed with saturated brine, dried over anhydrous sodium sulfate and concentrated under reduced pressure. The residue was purified by silica gel column chromatography (developing solvent: hexane:ethyl acetate=9:1→2:1) to give the title compound as a colorless oil (yield: 18 mg).

$^1$H-NMR (CDCl$_3$) δ: 0.97 (3H, d), 1.13 (3H, d), 2.10-2.40 (3H, m), 3.20-3.34 (1H, m), 3.50-3.60 (1H, m), 3.74 (1H, t), 4.50-4.60 (1H, m), 6.66 (1H, dd), 6.83 (1H, d), 7.55 (1H, d).

IR(KBr): 2963, 2220, 1613 cm$^{-1}$.

Example 33

4-[(2S,3R)-3-hydroxy-2-isopropylpyrrolidin-1-yl]-2-(trifluoromethyl)benzonitrile (compound 83)

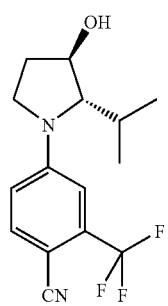 [SMILES: CC(C)[C@H]1[C@H](O)CCN1c1ccc(C#N)c(C(F)(F)F)c1]

Using benzyl (2S,3R)-3-{[tert-butyl(dimethyl)silyl]oxy}-2-isopropylpyrrolidine-1-carboxylate (400 mg), the title compound was obtained as a colorless solid (yield: 135 mg) by an operation similar to that in Example 32.

$^1$H-NMR (CDCl$_3$) δ: 0.90 (3H, d), 1.04 (3H, d), 1.90-2.12 (2H, m), 2.22-2.38 (1H, m), 3.45-3.65 (3H, m), 4.44 (1H, d), 6.68 (1H, dd), 6.85 (1H, d), 7.55 (1H, d).

IR(KBr): 2963, 2220, 1613 cm$^{-1}$.

Example 34

2-chloro-4-(octahydroquinolin-1(2H)-yl)benzonitrile (compound 84)

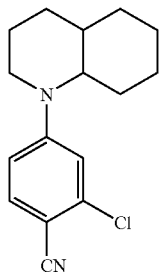 [SMILES: N#Cc1ccc(N2CCCC3CCCCC32)cc1Cl]

A solution (2 mL) of cis-decahydroquinoline (447 mg), 2-chloro-4-fluorobenzonitrile (500 mg) and lithium carbonate (237 mg) in dimethyl sulfoxide was reacted at 140° C. for 10 min in a microwave reaction apparatus. Water was added to the reaction mixture, and the mixture was extracted with ethyl acetate. The extract was washed with saturated brine, dried over anhydrous sodium sulfate and concentrated under reduced pressure. The residue was purified by silica gel column chromatography (developing solvent: hexane:ethyl acetate=9:1→1:1) to give the title compound as a colorless oil (yield: 600 mg).

$^1$H-NMR (CDCl$_3$) δ: 1.20-2.10 (13H, m), 2.92 (1H, dt), 3.50-3.60 (1H, m), 3.80-3.90 (1H, m), 6.69 (1H, dd), 6.81 (1H, d), 7.38 (1H, d).

Example 35

2-chloro-4-[(2S)-3-hydroxy-2-methylpiperidin-1-yl]benzonitrile (compound 85)

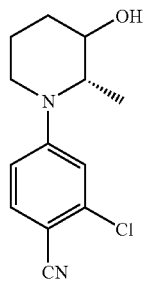 [SMILES: C[C@H]1C(O)CCCN1c1ccc(C#N)c(Cl)c1]

Using benzyl (2S)-3-{[tert-butyl(dimethyl)silyl]oxy}-2-methylpiperidine-1-carboxylate (250 mg), the title compound was obtained as a colorless oil (yield: 25 mg) by an operation similar to that in Example 32.

$^1$H-NMR (CDCl$_3$) δ: 1.10-1.30 (3H, m), 1.20-1.35 (1H, m), 1.55-2.00 (4H, m), 2.85-3.00 (1H, m), 3.44-3.55 (1H, m), 3.85-3.95 (1H, m), 4.15-4.25 (1H, m), 6.60-6.75 (1H, m), 6.84-6.86 (1H, m), 7.40-7.45 (1H, m).

IR(KBr): 3397, 2944, 2220, 1597 cm$^{-1}$.

The structures of the compounds in the Examples are shown in Tables 1 and 2.

TABLE 1

| Example No. | $R^6$ | $R^2$ | $R^3$ | $R^5$ | $R^4$ |
|---|---|---|---|---|---|
| 1 | —C(Me$_2$)OH | Cl | Me | H | H |
| 1(1) | —C(Me$_2$)OH | Cl | H | H | H |
| 1(2) | —C(Me$_2$)OH | H | Me | H | H |
| 1(3) | —C(Me$_2$)OH | H | H | H | H |
| 2 | OH | Cl | Me | H | H |
| 2(1) | OH | Cl | H | H | H |
| 2(2) | OH | H | H | H | H |
| 3 | —C(Me$_2$)OH | Cl | F | H | H |
| 4 | —C(Me$_2$)OH | Cl | H | Me | H |
| 5 | OH | Cl | H | Me | H |
| 6 | OH | Cl | Et | H | H |
| 7 | —C(Me$_2$)OH | Cl | Et | H | H |
| 8 | —C(Me$_2$)OH | CF$_3$ | H | H | H |
| 9 | OH | CF$_3$ | H | H | H |
| 10 | —C(Me$_2$)OH | F | H | H | H |
| 11 | —C(Me$_2$)OH | F | H | H | F |
| 12 | —C(Me$_2$)OH | F | F | F | H |
| 13 | —C(Me$_2$)OH | F | F | F | CN |
| 14 | —C(Me$_2$)OH | Cl | Cl | Me | H |
| 15 | OH | Cl | Cl | Me | H |
| 16 | —C(Me$_2$)OH | H | F | F | H |
| 17 | —C(Me$_2$)OH | OMe | H | H | H |
| 18 | —C(Me$_2$)OH | F | H | F | H |
| 19 | —C(Me$_2$)OH | H | OMe | H | H |
| 20 | —C(Me$_2$)OH | CN | H | H | H |
| 21 | —C(Me$_2$)OH | Br | H | H | H |
| 22 | —C(Me$_2$)OH | Cl | Pr | H | H |
| 23 | —C(Me$_2$)OH | Cl | CN | H | H |
| 24 | —C(Me$_2$)OH | F | OMe | F | H |
| 25 | —C(Me$_2$)OH | Cl | Cl | H | H |
| 26 | —C(Me$_2$)OH | CF$_3$ | H | Me | H |
| 27 | OH | Cl | Cl | H | H |
| 28 | OH | H | CF$_3$ | H | H |
| 29 | —C(Me$_2$)OH | Cl | H | F | H |
| 30 | —C(Me$_2$)OH | H | CF$_3$ | H | H |
| 31 | —C(Me$_2$)OH | Cl | CH$_2$OH | H | H |

TABLE 2

| Example 32 | Example 33 |
|---|---|
| 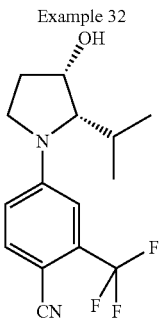 | 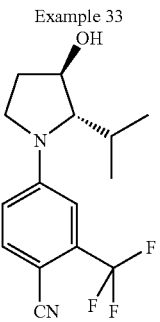 |
| Example 34 | Example 35 |
| 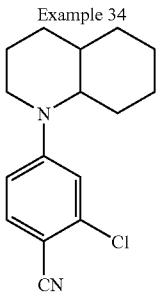 | 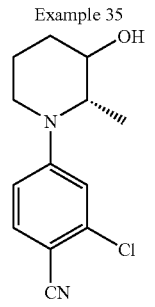 |

Experimental Example 1

AR Binding Inhibitory Test (Wild-Type, LNCaP-Type)

To a solution containing a wild-type androgen receptor (AR) or AR having LNCaP-type mutation were added 3 nM radiolabeled mibolerone and 100 nM compound. After the solution was incubated at 4° C. for 3 hr, B (Bound)/F (Free) separation was performed by the dextran/charcoal method. The label count of B was measured, and the inhibitory rate of the compound was calculated. The results are shown in Table 3.

TABLE 3

| | Inhibitory rate (%) at 100 nM | |
|---|---|---|
| Compound No. | wild-type | LNCaP-type |
| 2 | 99 | 99 |
| 3 | 98 | 99 |

Experimental Example 2

Evaluation of the Compound in Reporter Assay System to be Used Cos7 Cell

Cos-7 (5,000,000 cells) were sown in a flask (150 cm$^2$), and cultured in a culture medium (DMEM medium containing 10% Dextran Charcoal (DCC)-Fetal Bovine Serum (FBS) and 2 mM glutamine) for 24 hr. A vector DNA containing AR gene, and a vector DNA prepared by binging luciferase gene at the downstream of an androgen responsive promoter prepared by ligating two PSA promoter regions in tandem were co-transfected by the liposome method. After culture for 2 hr, the cells were harvested, 10,000 cells were plated on a 96 well plate and cultured for 3 hr, after which 1 µM of 5α-dihydrotestosterone or 100 nM of a compound was added thereto. After culture for 24 hr, luciferase activity was determined. The induction rate by the compound was determined with the luciferase activity induced by addition of 1 µM of 5α-dihydrotestosterone as 100. The results are shown in Table 4.

TABLE 4

| Compound No. | Induction rate (%) at 100 nM wild-type |
|---|---|
| 2 | 71 |
| 3 | 57 |

Experimental Example 3

PSA Production Test in Human Prostate Cancer Cell Line

The human prostate cancer cell line LNCaP-FGC was plated on a 96 well plate at 5,000 cells/100 µL/well. The next day, a test compound (final concentration 0.1-1000 nM), or a vehicle (control) or testosterone (final concentration 0.35-350 nM) was added thereto, and the culture supernatant was recovered 3 days after the drug addition. The concentration of PSA (Prostate Specific Antigen) produced in an androgen-dependent manner in the culture supernatant was measured by ELISA. The PSA production promotion rate by the test compound was calculated with vehicle addition group as 0 and 350 nM testosterone addition group as 100. The results are shown in Table 5.

TABLE 5

| Compound No. | PSA production promotion rate (%) |
|---|---|
| 2 | 103 |
| 3 | 81 |

Experimental Example 4

AR Binding Inhibitory Test (Wild-Type and LNCaP-Type)

To a solution containing a wild-type androgen receptor (AR) or AR having LNCaP-type mutation were added 3 nM radiolabeled mibolerone and 100 nM compound. After the solution was incubated at 4° C. for 3 hr, B (Bound)/F (Free) separation was performed by the dextran/charcoal method. The label count of B was measured, and the inhibitory rate of the compound was calculated. The results are shown in Table 6.

TABLE 6

| | Inhibitory rate (%) at 100 nM | |
|---|---|---|
| Compound No. | wild-type | LNcap-type |
| 53 | 98 | 98 |
| 71 | 99 | 97 |
| 75 | 99 | 99 |
| 80 | 97 | 95 |
| 82 | 98 | 97 |

Experimental Example 5

Evaluation of Compound in Reporter Assay System Using Cos7 Cell

Cos-7 (5,000,000 cells) were sown in a flask (150 cm$^2$), and cultured in a culture medium (DMEM medium containing 10% Dextran Charcoal (DCC)-Fetal Bovine Serum (FBS) and 2 mM glutamine) for 24 hr. A vector DNA containing AR gene, and a vector DNA prepared by binging luciferase gene at the downstream of an MMTV (Mouse Mammary Tumor Virus)-derived androgen responsive promoter were co-transfected by the liposome method. After culture for 2 hr, the cells were harvested, 10,000 cells were plated on a 96 well plate and cultured for 3 hr, after which 1 μM of 5α-dihydrotestosterone or 100 nM of a compound was added. After culture for 24 hr, luciferase activity was determined. The induction rate by the compound was determined with the luciferase activity induced by addition of 1 μM of 5α-dihydrotestosterone as 100. The results are shown in Table 7.

TABLE 7

| compound No. | Induction rate (%) at 100 nM wild-type |
|---|---|
| 53 | 33 |
| 71 | 31 |
| 75 | 60 |
| 80 | 22 |
| 82 | 90 |

Formulation Example 1

Microcapsule Containing Acetic Acid Leuprorelin

Leuprorelin acetate (5.8 g) was dissolved in distilled water (6.7 ml). Thereto was added a dichloromethane solution (138 g) containing polylactic acid (weight average molecular weight: 15000, 51.6 g), which was separately dissolved and filtrated. The mixture was stirred and emulsified in an auto-minimixer for 9 min (rpm: about 6000) and adjusted to 15° C. This was added to a 0.1% aqueous polyvinyl alcohol (PVA) solution (13.5 L) previously dissolved, filtrated and adjusted to the same temperature, to give an emulsion. In this case, homomix line flow (Tokushu Kika Co.) was used and the mixer was rotated at about 7000 rpm to give an emulsion. The W/O/W emulsion was desolvated while gently stirring for about 3 hr (in-water drying method).

The obtained microcapsule was passed through 74 μm sieves to remove crude particles, and separated by filtration or centrifugation. This was washed with distilled water to remove liberated drug and PVA, re-dispersed in a small amount of water, followed by dissolution of D-mannitol (8.7 g), sieving and freeze-drying. The shelf temperature was gradually raised during drying to allow drying finally at 52° C. for 69 hr. This was sieved and pulverized to give a microcapsule powder. This operation gave a microcapsule powder (58 g) containing 15% D-mannitol.

Formulation Example 2

Injection Containing Compound Described in Example 1

| | |
|---|---|
| (1) compound described in Example 1 | 5.0 mg |
| (2) sodium chloride | 20.0 mg |
| (3) distilled water | amount making total amount 2 ml |

The compound (5.0 mg) described in Example 1 and sodium chloride (20.0 mg) are dissolved in distilled water, and water is added to the total amount of 2.0 ml. The solution is filtrated, and aseptically filled in a 2 ml ampoule. The ampoule is sterilized and tightly sealed to give a solution for injection.

Formulation Example 3

Tablet Containing Testosterone

| | |
|---|---|
| (1) testosterone | 50 mg |
| (2) lactose | 34 mg |
| (3) cornstarch | 10.6 mg |
| (4) cornstarch (paste) | 5 mg |
| (5) magnesium stearate | 0.4 mg |
| (6) calcium carboxymethyl cellulose | 20 mg |
| Total | 120 mg |

According to a conventional method, the aforementioned (1)-(6) were mixed and tabulated by a tabletting machine to give a tablet.

Formulation Example 4

The preparation obtained in Formulation Example 1 and the preparation obtained in Formulation Example 2 are combined.

Formulation Example 5

The preparation obtained in Formulation Example 1 and the preparation obtained in Formulation Example 3 are combined.

Formulation Example 6

The preparation obtained in Formulation Example 1, the preparation obtained in Formulation Example 2 and the preparation obtained in Formulation Example 3 are combined.

INDUSTRIAL APPLICABILITY

The compound of the present invention has a superior action as an androgen receptor modulator (particularly agonist), and is useful for the prophylaxis or treatment of hypogonadism, male climacteric disorder, frailty, cachexia, osteoporosis and the like, for which administration of androgen is effective.

This application is based on application No. 2005-223462 filed in Japan, the contents of which are incorporated hereinto by reference.

The invention claimed is:

1. A compound represented by the formula (II)

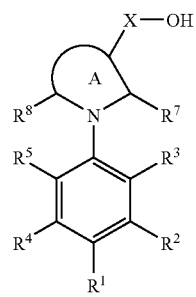

wherein
ring A is a pyrrolidine ring or a piperidine ring,
$R^1$ is a cyano group,
$R^2$ is a hydrogen atom, a cyano group, a halogen atom, a $C_{1-6}$ alkyl group substituted with 1 to 5 halogen atoms, or a $C_{1-6}$ alkoxy group,
$R^3$ is a hydrogen atom, a cyano group, a halogen atom, a $C_{1-6}$ alkyl group substituted with 1 to 5 halogen atoms, a $C_{1-6}$ alkoxy group, a $C_{1-6}$ alkyl group, or a $C_{1-6}$ alkyl group substituted with hydroxy group(s),
$R^4$ is a hydrogen atom, a halogen atom, or a cyano group,
$R^5$ is a hydrogen atom, a halogen atom, or a $C_{1-6}$ alkyl group,
$R^7$ is a $C_{1-6}$ alkyl group,
$R^8$ is a hydrogen atom, and
X is a bond or a linker represented by $CR^9R^{10}$ wherein $R^9$ is a $C_{1-6}$ alkyl group and $R^{10}$ is a $C_{1-6}$ alkyl group.

2. The compound of claim 1, which is selected from
i) 2-chloro-4-[(2S,3S)-3-(1-hydroxy-1-methylethyl)-2-methylpyrrolidin-1-yl]-3-methylbenzonitrile,
ii) 2-chloro-4-[(2S,3S)-3-(1-hydroxy-1-methylethyl)-2-methylpyrrolidin-1-yl]benzonitrile,
iii) 4-[(2S,3S)-3-(1-hydroxy-1-methylethyl)-2-methylpyrrolidin-1-yl]-2-methoxybenzonitrile,
iv) 2-bromo-4-[(2S,3S)-3-(1-hydroxy-1-methylethyl)-2-methylpyrrolidin-1-yl]benzonitrile, and
v) 4-[(2S,3S)-3-hydroxy-2-methylpyrrolidin-1-yl]-3-(trifluoromethyl)benzonitrile.

3. A pharmaceutical agent comprising a compound of claim 1 or a salt thereof.

4. A method for the treatment of hypogonadism, male climacteric disorder, frailty, cachexia or osteoporosis in a mammal, which comprises administering an effective amount of a compound of claim 1 or a salt thereof.

* * * * *